(12) United States Patent
Hu et al.

(10) Patent No.: US 9,157,126 B2
(45) Date of Patent: *Oct. 13, 2015

(54) SALIVARY PROTEIN BIOMARKERS FOR HUMAN ORAL CANCER

(71) Applicant: THE REGENTS OF THE UNIVERSITY OF CALIFORNIA, Oakland, CA (US)

(72) Inventors: Shen Hu, Simi Valley, CA (US); David T. W. Wong, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 14/169,634

(22) Filed: Jan. 31, 2014

(65) Prior Publication Data

US 2014/0206008 A1    Jul. 24, 2014

Related U.S. Application Data

(63) Continuation of application No. 12/739,703, filed as application No. PCT/US2008/081378 on Oct. 27, 2008, now Pat. No. 8,728,744.

(60) Provisional application No. 60/983,115, filed on Oct. 26, 2007, provisional application No. 61/084,343, filed on Jul. 29, 2008.

(51) Int. Cl.
  *G01N 33/574*   (2006.01)
  *C12Q 1/68*     (2006.01)
  *G01N 33/68*    (2006.01)

(52) U.S. Cl.
  CPC ........ *C12Q 1/6886* (2013.01); *G01N 33/57407* (2013.01); *G01N 33/6893* (2013.01); *G01N 2800/18* (2013.01)

(58) Field of Classification Search
  None
  See application file for complete search history.

(56) References Cited

U.S. PATENT DOCUMENTS

2007/0009501 A1  1/2007  Gires et al.
2010/0047830 A1  2/2010  Katz et al.

OTHER PUBLICATIONS

Elshal, M.F. et al., "Multiplex Bead Array Assays: Performance Evaluation and Comparison of Sensitivity to ELISA," *Methods*, Apr. 2006, vol. 38, Nov. 4, pp. 317-323.

IHOP (Information Hyperlinked Over Proteins) [online] "Synonyms of Rho GDP dissociation inhibitor (GDI) beta," retrieved from the internet on Apr. 6, 2009, located at, http://www.ihop-net.org/UniPub/iHOP/gs/86523.html, 6 pages.

International Search Report mailed on Apr. 14, 2009, for International Application No. PCT/US2008/081378, filed on Oct. 27, 2008, 2 pages.

Lo, W-Y. et al., "Identification of over-expressed proteins in oral squamous cell carcinoma (OSCC) patients by clinical proteomic analysis," *Clinica Chimica Acta*, 2007, vol. 376, pp. 101-107.

Mager, D.L. et al., "The salivary microbiota as a diagnostic indicator of oral cancer: A descriptive, non-randomized study of cancer-free and oral squamous cell carcinoma subjects," *Journal of Translational Medicine*, 2005, vol. 3, No. 27, pp. 1-8.

Na, S. et al., "D4-DGI, a Substrate of CPP32, is Proteolyzed during Fas-induced Apoptosis," *The Journal of Biological Chemistry*, May 10, 1996, vol. 271, No. 19, pp. 11209-11213.

Weng et al., "Searching for Potential Oral Cancer Markers on the Basis of Cancer Cell-secreted Proteomes," *Molecular and Cellular Proteomics*, 2005, 4:S167.

Hu et al., "Discovery and Validation of Salivary Protein Markers for Oral Diseases," *Molecular and Cellular Proteomics*, 2006, 5:S312.

Ravindranath et al., "Cell-surface density of complement restriction factors (DC46, CD55, and CD59): oral squamous cell carcinoma versus other solid tumors," *Oral Surgery, Oral Medicine, Oral Pathology, Oral Radiology, and Endodontology*, 2007, 103:231-239.

Yang et al., "Antioxidant enzyme levels in oral squamous cell carcinoma and normal human oral epithelium," *Journal of Oral Pathology & Medicine*, 2002, 31:71-77.

He et al., "Identification of tumor-associated proteins in oral tongue squamous cell carcinoma by proteonomics," *Proteonomics*, 2004, 4:271-278.

Tockman et al., "Considerations in Bringing a Cancer Biomarker to Clinical Application," *Cancer Res.*, 1992, 52:2711s-2718s.

Slamon et al., "Human breast cancer: correlation of relapse and survival with amplification of the HER-2/neu oncogene," *Science*, Jan. 1987, 235:177-182.

Brinkman et al., "Disease mechanism and biomarkers of oral squamous cell carcinoma," *Curr Opin Oncol*, May 2006, 18:228-233.

Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.

*Primary Examiner* — Mark Halvorson
(74) *Attorney, Agent, or Firm* — Riverside Law LLP

(57) ABSTRACT

The present invention relates to the identification of novel oral cancer and periodontal disease biomarkers. Further, the present invention provides novel methods of diagnosing and for providing a prognosis for oral cancer and periodontal disease. The present invention additionally provides novel methods of distinguishing between oral cancer and periodontal disease. Finally, kits are provided that find use in the practice of the methods of the invention.

9 Claims, 59 Drawing Sheets

Fig. 5
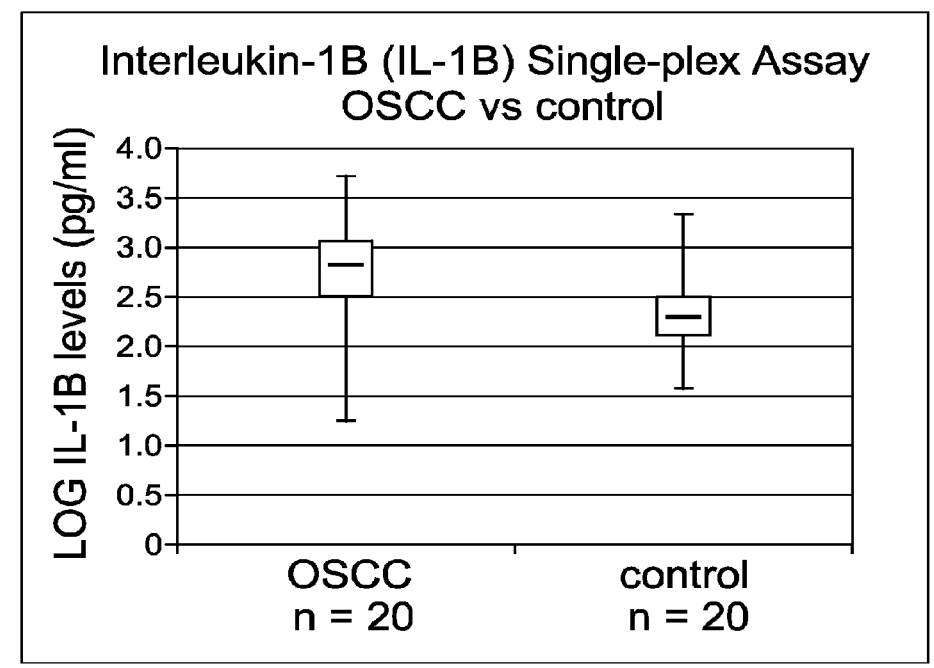
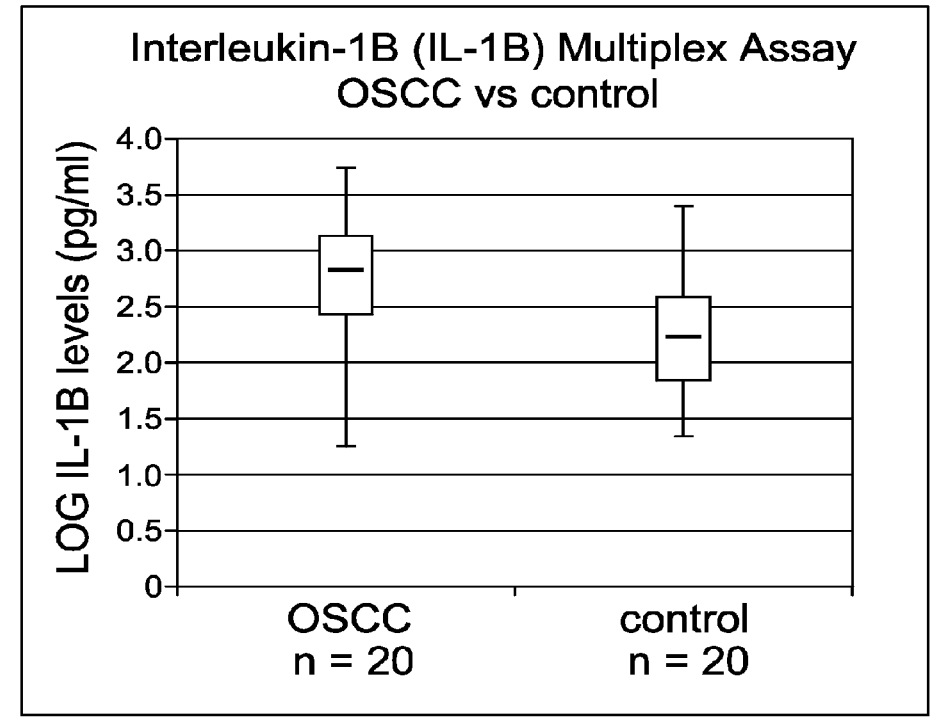

Fig. 6
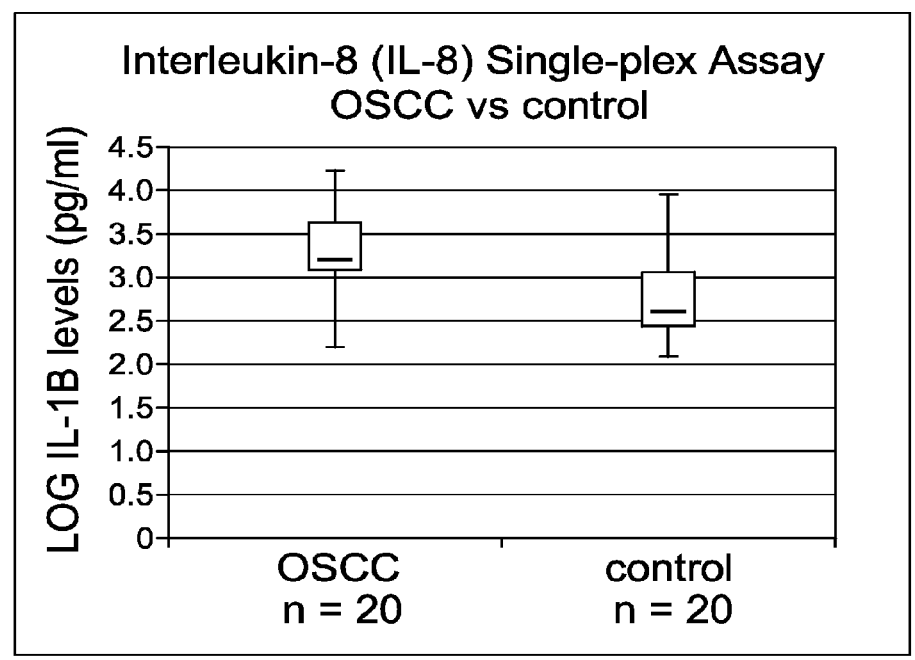
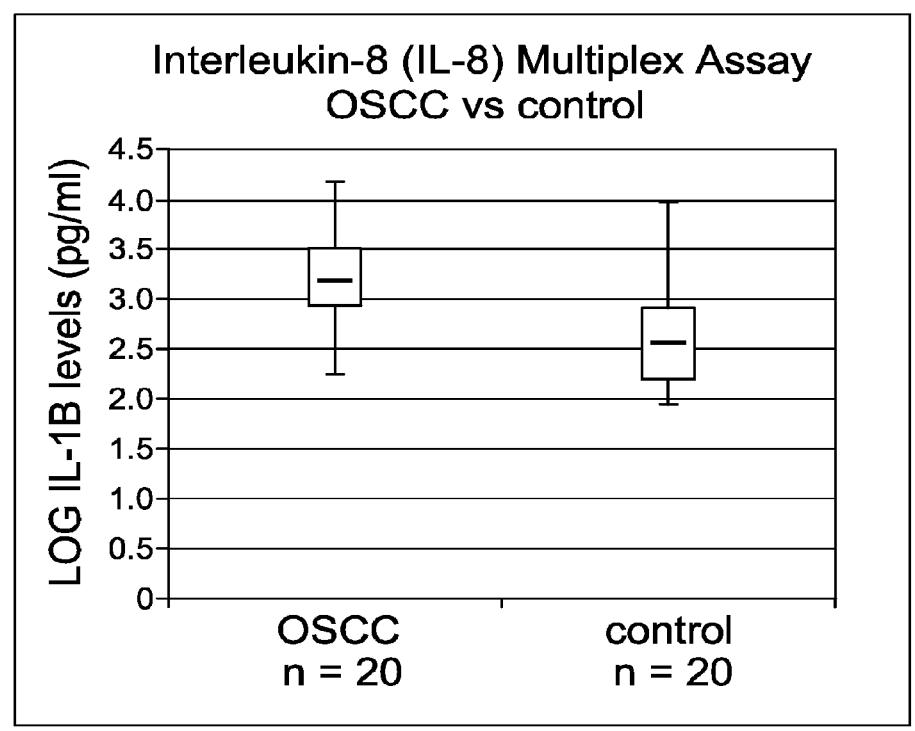

Figure 9A

Table 4
Saliva proteins identified only from OSCC patients by subtractive proteomics

| Accession number | Protein name | Peptide sequence | Peptide score | Protein mass | Protein PI | SEQ ID NO: |
|---|---|---|---|---|---|---|
| IPI00010303 | Squamous cell carcinoma antigen 2 | TNSILFYGR | 46.25 | 44825 | 5.86 | 1 |
| IPI00011302 | CD59 glycoprotein | AGLQVYNK | 47.97 | 14168 | 6.02 | 2 |
| IPI00011692 | Involucrin | HVLQQEGQLEQQER | 51.84 | 68427 | 4.62 | 3 |
| IPI00016342 | Ras-related protein Rab-7 | VIILGDSGVGK | 57.39 | 23475 | 6.4 | 4 |
| IPI00023673 | Mac-2 binding protein | ASHEEVEGLVEK | 27.48 | 65289 | 5.13 | 5 |
|  |  | IDITLSSVK | 46.96 |  |  | 6 |
|  |  | RIDITLSSVK | 40.28 |  |  | 7 |
|  |  | SDLAVPSELALLK | 43.78 |  |  | 8 |
|  |  | SDLAVPSELALLK | 39.92 |  |  | 8 |
|  |  | TLQALEFHTVPFQLLAR | 62.99 |  |  | 9 |
| IPI00025318 | SH3 domain-binding glutamic acid-rich-like protein | DIAANEENR | 53.95 | 12766 | 5.22 | 10 |
|  |  | DIAANEENRK | 26.08 |  |  | 11 |
|  |  | ENNAVYAFLGLTAPPGSK | 58.00 |  |  | 12 |
|  |  | QQDVLGFLEANK | 60.33 |  |  | 13 |
|  |  | QQDVLGFLEANK | 77.61 |  |  | 13 |
|  |  | VYIASSGSTAIK | 66.47 |  |  | 14 |

Figure 9B

| Accession number | Protein name | Peptide sequence | Peptide score | Protein mass | Protein PI | SEQ ID NO: |
|---|---|---|---|---|---|---|
| IPI00026156 | Hematopoietic lineage cell specific protein | TTPIEAASSGAR | 52.40 | 53965 | 4.74 | 15 |
| | | TTPIEAASSGAR | 44.56 | | | 15 |
| IPI00026156 | Histone H1.2 | ASGPPVSELITK | 60.76 | 22938 | 10.8 | 16 |
| | | ASGPPVSELITK | 64.32 | | | 16 |
| IPI00217471 | Epsilon globin | LLVVYPWTQR | 49.07 | 16192 | 8.67 | 17 |
| IPI00218131 | S100 calcium-binding protein A12 | AVIDEIFQGLDANQDEQVDFQEFISLVAIALK | 102.48 | 10569 | 5.83 | 18 |
| | | ELANTIK | 52.51 | | | 19 |
| | | ELANTIK | 44.04 | | | 19 |
| | | GHFDTLSK | 44.75 | | | 20 |
| | | GHFDTLSKGELK | 49.86 | | | 21 |
| IPI00003734 | Putative S100 calcium-binding protein H-NH0456N16.1 | DPGVLDR | 29.40 | 11502 | 8.83 | 22 |
| | | TEFLSFMNTELAAFTK | 85.83 | | | 23 |
| IPI00027463 | Calcyclin | LQDAEIAR | 52.13 | 10173 | 5.33 | 24 |
| | | LQDAEIAR | 64.58 | | | 24 |
| | | LQDAEIAR | 52.16 | | | 24 |
| IPI00028064 | Cathepsin G | NVNPVALPR | 42.51 | 28819 | 11.19 | 25 |
| | | VSSFLPWIR | 41.46 | | | 26 |
| IPI00298853 | Vitamin D-binding protein | VLEPTLK | 46.09 | 52929 | 5.4 | 27 |

Figure 9C

| Accession number | Protein name | Peptide sequence | Peptide score | Protein mass | Protein PI | SEQ ID NO: |
|---|---|---|---|---|---|---|
| IPI00299024 | Brain acid soluble protein 1 | ETPAATEAPSSTPK | 50.99 | 28924 | 5.1 | 28 |
| | | ETPAATEAPSSTPK | 31.11 | | | 28 |
| IPI00411291 | Peroxisome biogenesis factor 1 | GMMKELQTK | 42.12 | 142778 | 5.91 | 29 |
| | | GMMKELQTK | 42.36 | | | 29 |
| | | GMMKELQTK | 35.66 | | | 29 |
| | | GMMKELQTK | 45.88 | | | 29 |
| | | GMMKELQTK | 42.33 | | | 29 |
| | | GMMKELQTK | 33.16 | | | 29 |
| | | GMMKELQTK | 34.29 | | | 29 |
| | | GMMKELQTK | 41.95 | | | 29 |
| | | GMMKELQTK | 46.21 | | | 29 |
| | | GMMKELQTK | 41.78 | | | 29 |
| | | GMMKELQTK | 40.73 | | | 29 |
| | | GMMKELQTK | 42.36 | | | 29 |
| | | GMMKELQTK | 45.74 | | | 29 |
| | | GMMKELQTK | 42.45 | | | 29 |
| | | GMMKELQTK | 46.46 | | | 29 |
| | | GMMKELQTK | 40.70 | | | 29 |
| | | GMMKELQTK | 42.02 | | | 29 |
| | | GMMKELQTK | 26.92 | | | 29 |
| | | GMMKELQTK | 26.24 | | | 29 |
| | | GMMKELQTK | 42.29 | | | 29 |
| | | GMMKELQTK | 41.97 | | | 29 |

Figure 9D

| Accession number | Protein name | Peptide sequence | Peptide score | Protein mass | Protein PI | SEQ ID NO: |
|---|---|---|---|---|---|---|
| IPI00219365 | Moesin | FYPEDVSEELIQDDITQR | 49.41 | 67778 | 6.08 | 30 |
| IPI00465436 | Catalase | DAQIFIQK | 29.94 | 59696 | 7.37 | 31 |
| | | DFPPILFPSFIHHSQK | 33.77 | | | 302 |
| | | FSTVAGESGSADTVR | 102.47 | | | 33 |
| | | FSTVAGESGSADTVRDPR | 25.34 | | | 34 |
| | | GAGAFGYFEVTHDITK | 28.12 | | | 35 |
| | | LNVITVGPR | 48.18 | | | 36 |
| | | NLSVEDAAR | 52.14 | | | 37 |
| | | VNPTVFFDIAVDGEPLGR | 49.90 | | | 38 |
| IPI00549466 | Peptidylprolyl isomerase A-like | VNPTVFFDIAVDGEPLGR | 75.47 | 17987 | 7.68 | 38 |
| IPI00236554 | Splice isoform 2 Of Myeloperoxidase | AVSNEIVR | 63.16 | 73087 | 9.3 | 39 |
| | | DYLPLVLGPTAMR | 47.71 | | | 40 |
| | | IGLDLPALNMQR | 81.27 | | | 41 |
| | | NNIFMSNSYPR | 43.16 | | | 42 |

Figure 9E

| Accession number | Protein name | Peptide sequence | Peptide score | Protein mass | Protein PI | SEQ ID NO: |
|---|---|---|---|---|---|---|
| | | NQINALTSFVDASMVYGGEEPKAR | 53.47 | | | 43 |
| | | QALAQISLPR | 60.96 | | | 44 |
| | | SPTLGASNR | 57.88 | | | 46 |
| | | SRDHGLPGYNAWR | 39.85 | | | 47 |
| | | VFFASWR | 40.94 | | | 48 |
| | | VVLEGGIDPILR | 60.68 | | | 49 |
| IPI00007244 | Splice isoform 1 of Myeloperoxidase | AVSNEIVR | 57.38 | 83815 | 9.19 | 39 |
| | | IANVFTNAFR | 56.93 | | | 50 |
| | | IGLDLPALNMQR | 63.64 | | | 41 |
| | | QNQIAVDEIR | 70.90 | | | 45 |
| | | QNQIAVDEIR | 69.31 | | | 45 |
| | | SPLTGASNR | 45.04 | | | 46 |
| | | VGPLLACIIGTQFR | 29.74 | | | 51 |
| | | VVLEGGIDPILR | 41.95 | | | 49 |
| IPI00007244 | Haptoglobin-related protein | DIAPTLTLYVGK | 38.23 | 43049 | 6.66 | 52 |
| IPI00297058 | Tumor-related protein | ELYSYLR | 53.12 | 53512 | 5.73 | 53 |
| | | ELYSYLR | 35.41 | | | 53 |
| | | LDQGNLHTSVSSAQGQDAAQSEEK | 44.51 | | | 54 |
| | | LDQGNLHTSVSSAQGQDAAQSEEKR | 31.47 | | | 55 |

Figure 9F

| Accession number | Protein name | Peptide sequence | Peptide score | Protein mass | Protein PI | SEQ ID NO: |
|---|---|---|---|---|---|---|
| | | QPTVVGEEWVDDHSR | 40.70 | | | 56 |
| | | SQTSQAVTGGHTQIQAGSHTETVEQDR | 27.80 | | | 57 |
| IPI00298828 | Beta-2-glycoprotein 1 | ATVVYQGER | 36.39 | 38273 | 8.34 | 58 |
| IPI00027350 | Peroxiredoxin 2 | QITVNDLPVGR | 49.72 | 21878 | 5.66 | 59 |
| | | TDEGIAYR | 51.82 | | | 60 |
| IPI00216298 | Thioredoxin | EKLEATINELV | 37.64 | 13665 | 4.99 | 61 |
| | | MIKPFFHSLSEK | 26.29 | | | 62 |
| | | MIKPFFHSLSEK | 33.32 | 63 | | 62 |
| | | TAFQEALDAAGDK | 75.29 | | | 63 |
| | | TAFQEALDAAGDK | 75.07 | | | 63 |
| | | VGEFSGANK | 26.42 | | | 64 |
| | | VGEFSGANK | 45.29 | | | 64 |
| IPI00304925 | Heat shock 70 kDa protein 1 | DAGVIAGLNVLR | 45.90 | 70009 | 5.48 | 65 |
| | | DAGVIAGLNVLR | 37.76 | | | 65 |
| | | LLQDFFNGR | 52.58 | | | 66 |
| | | LVNHFVEEFKR | 45.77 | | | 67 |
| | | LVNHFVEEFKR | 43.39 | | | 67 |

Figure 9G

| Accession number | Protein name | Peptide sequence | Peptide score | Protein mass | Protein PI | SEQ ID NO: |
|---|---|---|---|---|---|---|
| IPI00465248 | Enolase 1 | NALESYAFNMK | 68.00 | | | 68 |
| | | STLEPVEK | 26.26 | | | 69 |
| | | AAVPSGASTGIYEALELR | 110.42 | 47139 | 7.01 | 70 |
| | | GNPTVEVDLFTSK | 83.35 | | | 73 |
| | | GNPTVEVDLFTSK | 65.28 | | | 73 |
| | | IEEELGSK | 39.39 | | | 74 |
| | | LAMQEFMILPVGAANFR | 30.19 | | | 75 |
| | | LAQANGWGVWVSHR | 76.77 | | | 76 |
| | | LNVTEQEK | 35.98 | | | 77 |
| | | TIAPALVSK | 37.99 | | | 78 |
| | | YISPDQLADLYK | 54.73 | | | 79 |
| | | YISPDQLADLYK | 53.69 | | | 79 |
| | | YISPDQLADLYK | 70.98 | | | 79 |
| | | YISPDQLADLYK | 69.38 | | | 79 |
| | | YNQLLR | 35.66 | | | 80 |
| | | YNQLLR | 26.56 | | | 80 |
| | | YNQLLR | 41.11 | | | 80 |
| IPI00216171 | Enolase 2 | GNPTVEVDLYTAK | 66.04 | 47239 | 4.91 | 81 |
| | | GNPTVEVDLYTAK | 48.90 | | | 81 |

Figure 9H

| Accession number | Protein name | Peptide sequence | Peptide score | Protein mass | Protein pI | SEQ ID NO: |
|---|---|---|---|---|---|---|
| IPI00216171 | Enolase 2 | GNPTVEVDLHTAK | 59.73 | 46929 | 7.59 | 82 |
| | | VNQIGSVTESIQACK | 80.09 | | | 83 |
| IPI00216171 | Alpha enolase, lung specific | VNQIGSVTESLQACK | 80.09 | 49446 | 5.78 | 84 |
| | | YISPDQLADLYK | 46.44 | | | 85 |
| | | YISPDQLADLYK | 59.22 | | | 85 |
| | | YISPDQLADLYK | 61.89 | | | 85 |
| | | YISPDQLADLYK | 58.92 | | | 85 |
| IPI00292532 | Antibacterial protein FALL-39 | AIDGINQR | 49.31 | 19289 | 9.48 | 86 |
| | | AIDGINQR | 40.05 | | | 86 |
| | | SSDANLYR | 81.03 | | | 87 |
| | | SSDANLYR | 81.74 | | | 87 |
| IPI00465028 | Triosephosphate isomerase | SNVSDAVAQSTR | 83.07 | 27924 | 6.15 | 88 |
| | | TATPQQAQEVHEK | 58.68 | | | 89 |
| IPI00017526 | S-100P protein | ELPGFLQSGK | 26.97 | 10393 | 4.75 | 90 |
| | | ELPGFLQSGK | 37.50 | | | 90 |

Figure 9I

| Accession number | Protein name | Peptide sequence | Peptide score | Protein mass | Protein PI | SEQ ID NO: |
|---|---|---|---|---|---|---|
| IPI00027409 | Myeloblastin | YSGSEGSTQTLTK | 81.77 | | | 91 |
| | | YSGSEGSTQTLTK | 91.39 | | | 91 |
| | | YSGSEGSTQTLTK | 75.66 | | | 91 |
| | | LFPDFFTR | 37.54 | 27789 | 8.72 | 92 |
| | | LFPDFFTR | 39.61 | | | 92 |
| | | LVNVVLGAHNVR | 43.46 | | | 93 |
| | | LVNVVLGAHNVR | 48.35 | | | 93 |
| | | LVNVVLGAHNVR | 47.89 | | | 93 |
| IPI00013895 | Calgizzarin | CIESLIAVFQK | 31.31 | | | 94 |
| | | DGYNYTLSK | 51.47 | 11733 | 6.56 | 95 |
| | | DGYNYTLSK | 48.83 | | | 95 |
| | | ISSPTETER | 51.71 | | | 96 |
| | | TEFLSFMNTELAAFTK | 47.51 | | | 97 |
| | | TEFLSFMNTELAAFTK | 60.91 | | | 97 |
| IPI00215983 | Carbonic anhydrase I | ADGLAVIGVLMK | 35.28 | 28852 | 6.59 | 98 |
| | | ADGLAVIGVLMK | 51.69 | | | 98 |
| | | VLDALQAIK | 55.76 | | | 99 |
| | | VLDALQAIK | 54.18 | | | 99 |
| | | VLDALQAIK | 54.99 | | | 99 |
| | | VLDALQAIK | 45.03 | | | 99 |

Figure 9J

| Accession number | Protein name | Peptide sequence | Peptide score | Protein mass | Protein PI | SEQ ID NO: |
|---|---|---|---|---|---|---|
| | | YSSLAEAASK | 35.18 | | | 100 |
| | | YSSLAEAASK | 67.70 | | | 100 |
| | | YSSLAEAASK | 52.14 | | | 100 |
| IPI00744692 | Transaldolase | LFVLFGAEILK | 45.56 | 37670 | 6.7 | 101 |
| | | LLGELLQDNAK | 47.68 | | | 102 |
| | | LLGELLQDNAK | 66.36 | | | 102 |
| | | TIVMGASFR | 34.77 | | | 103 |
| IPI00022429 | Alpha-1-acid glycoprotein 1 | EQLGEFYEALDCLR | 73.20 | 24770 | 5.11 | 104 |
| | | TEDTIFLR | 54.19 | | | 105 |
| | | YVGGQEHFAHLLILR | 55.90 | | | 106 |
| IPI00022246 | Azurocidin | CQVAGWGSQR | 47.58 | 24655 | 10.65 | 107 |
| | | HFCGGALIHAR | 49.04 | | | 108 |
| | | QFPFLASIQNQGR | 48.50 | | | 109 |
| | | QFPFLASIQNQGR | 75.75 | | | 109 |
| | | QFPFLASIQNQGR | 39.52 | | | 109 |
| IPI00004815 | Similar to SEC14-like protein 2 | IVILGDNWK | 42.34 | 49394 | 7.49 | 110 |
| IPI00010252 | Splice isoform 1 Of transcription factor 1-gamma | GAIENLLAK | 40.15 | 122444 | 6.23 | 111 |

Figure 9K

| Accession number | Protein name | Peptide sequence | Peptide score | Protein mass | Protein PI | SEQ ID NO: |
|---|---|---|---|---|---|---|
| IPI00022488 | Hemopexin | GGYTLVSGYPK | 57.83 | 51643 | 6.55 | 112 |
| | | NFPSPVDAAFR | 38.81 | | | 113 |
| | | NFPSPVDAAFR | 28.24 | | | 113 |
| | | NFPSPVDAAFR | 55.56 | | | 113 |
| | | NFPSPVDAAFR | 39.66 | | | 113 |
| IPI00023456 | Muscarinic acetylcholine receptor M3 | MSLVKEK | 41.63 | 66086 | 9.33 | 114 |
| IPI00032134 | Cytoplasmic antiproteinase 2 | LVLVNAIYFK | 65.25 | 42758 | 5.43 | 115 |
| IPI00152241 | Similar to Myomegalin | GQLGLGGSR | 41.33 | 24409 | 5.71 | 116 |
| IPI00152881 | Shroom-related protein | SSPATADKR | 50.35 | 216528 | 7.75 | 117 |
| | | SSPATADKR | 35.70 | | | 117 |
| | | SSPATADKR | 30.04 | | | 117 |
| | | SSPATADKR | 31.88 | | | 117 |
| | | SSPATADKR | 48.19 | | | 117 |
| | | SSPATADKR | 38.51 | | | 117 |
| | | SSPATADKR | 38.74 | | | 117 |
| | | SSPATADKR | 40.96 | | | 117 |
| | | SSPATADKR | 44.26 | | | 117 |
| | | SSPATADKR | 48.28 | | | 117 |
| | | SSPATADKR | 33.54 | | | 117 |
| | | SSPATADKR | 61.38 | | | 117 |

Figure 9L

| Accession number | Protein name | Peptide sequence | Peptide score | Protein mass | Protein PI | SEQ ID NO: |
|---|---|---|---|---|---|---|
| IPI00169383 | Phosphoglycerate kinase 1 | SSPATADKR | 36.26 | | | 117 |
| | | SSPATADKR | 48.36 | | | 117 |
| | | SSPATADKR | 32.20 | | | 117 |
| | | LGDVYVNDAFGTAHR | 42.70 | 44588 | 8.3 | 118 |
| IPI00414741 | 11 kDa protein | EVQLVESGGGLVQPGGSLR | 53.51 | 10807 | 8.07 | 119 |
| | | EVQLVESGGGLVQPGGSLR | 72.15 | | | 119 |
| | | EVQLVESGGGLVQPGGSLR | 73.48 | | | 119 |
| | | EVQLVESGGGLVQPGGSLR | 93.21 | | | 119 |
| | | EVQLVESGGGLVQPGGSLR | 57.10 | | | 119 |
| | | EVQLVESGGGLVQPGGSLR | 49.67 | | | 119 |
| | | EVQLVESGGGLVQPGGSLR | 66.95 | | | 119 |
| | | EVQLVESGGGLVQPGGSLR | 56.62 | | | 119 |

Figure 9M

| Accession number | Protein name | Peptide sequence | Peptide score | Protein mass | Protein PI | SEQ ID NO: |
|---|---|---|---|---|---|---|
| | | EVQLVESGGGLVQPGGSLR | 112.54 | | | 119 |
| | | EVQLVESGGGLVQPGGSLR | 64.17 | | | 119 |
| | | EVQLVESGGGLVQPGGSLR | 89.59 | | | 119 |
| | | NSLYLQMNSLR | 54.70 | | | 120 |
| | | NSLYLQMNSLR | 52.66 | | | 120 |

Figure 9N

| Accession number | Protein name | Peptide sequence | Peptide score | Protein mass | Protein pI | SEQ ID NO: |
|---|---|---|---|---|---|---|
| IPI00334432 | 16 kDa protein | NSLYLQMNSLR | 63.06 | | | 120 |
| | | NSLYLQMNSLR | 51.79 | | | 120 |
| | | NSLYLQMNSLR | 62.73 | | | 120 |
| | | NSLYLQMNSLR | 36.85 | | | 120 |
| | | NSLYLQMNSLR | 43.75 | | | 120 |
| | | MFLSFPTTK | 38.34 | 15532 | 8.76 | 121 |
| | | MFLSFPTTK | 34.87 | | | 121 |
| | | MFLSFPTTK | 38.35 | | | 121 |
| | | MFLSFPTTK | 36.75 | | | 121 |
| | | TYFPHFDLSHGSAQVK | 25.01 | | | 122 |
| | | TYFPHFDLSHGSAQVK | 25.27 | | | 122 |
| IPI00479902 | 57 kDa protein | QSVEADINGLRR | 39.43 | 56528 | 5.09 | 123 |
| | | VLDELTLTK | 41.65 | | | 124 |
| IPI00023456 | 143 kDa protein | FGQGSGPIVLDDVR | 83.03 | 143097 | 4.95 | 125 |
| | | VEILYR | 41.18 | | | 126 |

Figure 10A

Table 5

Saliva proteins identified only from healthy subjects by subtractive proteomics

| Accession number | Protein name | Peptide sequence | Peptide score | Protein mass | Protein pI | SEQ ID NO: |
|---|---|---|---|---|---|---|
| IPI00291262 | Clusterin | ASSIIDELFQDR | 70.53 | 52461 | 5.89 | 127 |
| | | ELDESLQVAER | 61.57 | | | 128 |
| | | FMETVAEK | 35.33 | | | 129 |
| | | IDSLLENOR | 45.88 | | | 130 |
| IPI00006705 | Uteroglobin | KLVDTLPQKPR | 45.46 | 9987 | 4.99 | 131 |
| | | LVDTLPQKPR | 49.98 | | | 132 |
| IPI00009329 | Utrophin | QELPPPPPPK | 39.67 | 394248 | 5.21 | 133 |
| | | SKQELPPPPPPK | 21.73 | | | 134 |
| | | SKQELPPPPPPK | 22.68 | | | 134 |
| | | SKQELPPPPPPK | 23.60 | | | 134 |
| IPI00017987 | Connifin A | IPEPCQPK | 53.39 | 9876 | 8.85 | 1354 |
| | | IPEPCQPK | 40.46 | | | 135 |
| | | IPEPCQPK | 32.25 | | | 135 |
| | | QPCQPPPQEPCIPK | 36.35 | | | 136 |
| | | QPCQPPPQEPCIPK | 38.03 | | | 136 |
| | | VPEPCPSTVTPAPAQQK | 46.33 | | | 137 |
| | | VPEPCPSTVTPAPAQQK | 53.59 | | | 137 |

Figure 10B

| Accession number | Protein name | Peptide sequence | Peptide score | Protein mass | Protein PI | SEQ ID NO: |
|---|---|---|---|---|---|---|
| IPI00304903 | Connitin B | QPCQPPPQEPCIPK | 36.35 | 9893 | 8.85 | 136 |
| | | QPCQPPPQEPCIPK | 38.03 | | | 136 |
| | | VPEPCPSIVTPAPAQQK | 36.58 | | | 138 |
| IPI00296777 | SPARC-like protein 1 | LLAGDHPIDLLLR | 43.28 | 75169 | 4.68 | 139 |
| | | TGLEAISNHKETEEK | 20.97 | | | 140 |
| IPI00032292 | Metalloproteinase inhibitor 1 | GFQALGDAADIR | 48.75 | 23156 | 8.46 | 141 |
| | | GFQALGDAADIR | | | | 141 |
| | | HLACLPR | 21.06 | | | 142 |
| IPI00293276 | Macrophage migration inhibitory factor | LLCGLLAER | 52.16 | 15967 | 9.5 | 143 |
| IPI00008580 | Antileukoproteinase 1 | CLDPVDTPNPTR | 21.19 | 14316 | 9.11 | 144 |
| | | CLDPVDTPNPTR | 51.97 | | | 144 |
| | | CLDPVDTPNPTR | 28.86 | | | 144 |
| | | CLDPVDTPNPTR | 33.50 | | | 144 |
| | | CLDPVDTPNPTR | 41.89 | | | 144 |
| | | CLDPVDTPNPTR | 28.06 | | | 144 |
| | | CLDPVDTPNPTR | 35.71 | | | 144 |
| | | CLDPVDTPNPTR | 37.29 | | | 144 |

Figure 10C

| Accession number | Protein name | Peptide sequence | Peptide score | Protein mass | Protein PI | SEQ ID NO: |
|---|---|---|---|---|---|---|
| | | SCVSPVKA | 31.35 | | | 145 |
| | | SCVSPVKA | 35.22 | | | 145 |
| | | SCVSPVKA | 40.79 | | | 145 |
| | | SCVSPVKA | 31.78 | | | 145 |
| | | SCVSPVKA | 22.63 | | | 145 |

Figure 10D

| Accession number | Protein name | Peptide sequence | Peptide score | Protein mass | Protein pI | SEQ ID NO: |
|---|---|---|---|---|---|---|
| IPI00031547 | Desmoglein | TITAEVLAIDEYTGK | 78.05 | 107435 | 4.86 | 146 |
| IPI00030757 | Splice isoform Of ADAMTS-2 | IQELIDEMR | 44.42 | 134636 | 6.76 | 147 |
|  |  | IQELIDEMR | 64.39 |  |  | 147 |
|  |  | IQELIDEMR | 56.59 |  |  | 147 |
| IPI00103516 | Cask-interacting protein 2 | KGPPPPPPK 148 | 47.84 | 126633 | 6.73 | 149 |
| IPI00328293 | Serine/arginine repetitive matrix 1 | RTPTPPPR | 21.38 | 103329 | 11.85 | 150 |
|  |  | TASPPPPPK | 26.64 |  |  | 150 |
|  |  | TASPPPPPK | 35.96 |  |  | 150 |
|  |  | TASPPPPPK | 28.00 |  |  | 150 |
| IPI00021751 | Neurofilament triplet H protein | LLEGEECR | 52.74 | 112411 | 5.99 | 151 |
| IPI00384448 | Actin-related protein 5 | LQELNAVRR | 20.16 | 31378 | 8.39 | 152 |
|  |  | LQELNAVRR | 20.46 |  |  | 152 |
|  |  | LQELNAVRR | 32.74 |  |  | 152 |
|  |  | LQELNAVRR | 25.57 |  |  | 152 |
| IPI00550166 | Similar to Ig gamma-3 chain C-region | EPQVYTLPPSR | 43.70 | 55327 | 8.42 | 154 |

Figure 10E

| Accession number | Protein name | Peptide sequence | Peptide score | Protein mass | Protein pI | SEQ ID NO: |
|---|---|---|---|---|---|---|
| IPI00398052 | Similar to heterogeneous nuclear ribonucleoprotein K | GPPPPLTGR | 36.95 | 42939 | 4.91 | 155 |
| | | GPPPPLTGR | 34.65 | | | 155 |
| | | GPPPPLTGR | 36.91 | | | 155 |
| | | GPPPPLTGR | 39.94 | | | 155 |
| | | GPPPPLTGR | 21.79 | | | 155 |
| | | GPPPPLTGR | 34.91 | | | 155 |
| | | GPPPPLTGR | 30.74 | | | 155 |
| | | GPPPPLTGR | 28.06 | | | 155 |
| | | GPPPPLTGR | 36.95 | | | 155 |
| | | GPPPPLTGR | 24.14 | | | 155 |
| | | GPPPPLTGR | 28.68 | | | 155 |
| | | GPPPPLTGR | 21.03 | | | 155 |
| | | GPPPPLTGR | 27.73 | | | 155 |
| IPI00003542 | Airway trypsin-like protease | LENSVTFTK | 59.68 | 46234 | 8.69 | 156 |
| IPI00013678 | Metaxin 1 isoform 1 | LQVHLR | 26.58 | 51445 | 9.8 | 157 |
| | | SPRSGTSPK | 36.94 | | | 158 |
| IPI00017870 | OTTHUMP00000021786 | FASFIDK | 41.28 | 55117 | 4.85 | 159 |
| | | FASFIDK | 28.54 | | | 159 |
| IPI00219806 | OTTHUMP00000059857 | GTNYLADVFEK | 47.76 | 11464 | 6.28 | 160 |

Figure 10F

| Accession number | Protein name | Peptide sequence | Peptide score | Protein mass | Protein pI | SEQ ID NO: |
|---|---|---|---|---|---|---|
| IPI00514288 | 9 kDa protein | MQIFVK | 25.51 | 8600 | 5.76 | 161 |
| | | TLSNYNIQK | 43.07 | | | 162 |
| IPI00164375 | 42 kDa protein | LASYLDK | 39.49 | 41925 | 4.67 | 163 |
| IPI00164540 | 43 kDa protein | ASLENSLEETKGR | 40.06 | 43122 | 4.83 | 164 |
| | | ASLENSLEETKGR | 41.57 | | | 164 |
| | | DAEFWFFSK | 51.02 | | | 165 |
| | | EVATNSELVQSGK | 100.01 | | | 166 |

Figure 10G

| Accession number | Protein name | Peptide sequence | Peptide score | Protein mass | Protein PI | SEQ ID NO: |
|---|---|---|---|---|---|---|
| IPI00412044 | 86 kDa protein | EVATNSELVQSGK | 100.16 | | | 166 |
| | | LASYLDK | 40.79 | | | 163 |
| | | LASYLDK | 40.91 | | | 163 |
| | | VLDELTLAR | 46.83 | | | 167 |
| | | FGQGSGPIVLDDVR | 49.32 | 85783 | 4.82 | 168 |
| | | FGQGSGPIVLDDVR | 45.31 | | | 168 |
| | | FGQGSGPIVLDDVR | 92.32 | | | 168 |
| | | GRVEVLYR | 36.60 | | | 169 |
| | | QLGCGWATSAPGNAR | 63.84 | | | 170 |
| | | QLGCGWATSAPGNAR | 54.95 | | | 170 |
| | | VEILYR | 75.32 | | | 171 |
| | | VEVLYR | 41.92 | | | 171 |
| IPI00411959 | 172 kDa protein | QLGCGWATSAPGNAR | 36.96 | 171861 | 5 | 170 |
| IPI00418157 | Hypothetical protein DKFZp686O16217 | DASGATFTWTPSSGK | 67.43 | 54090 | 6.88 | 172 |
| | | DASGATFTWTPSSGK | 67.43 | | | 172 |
| | | SGNTFRPEVHLLPPPSEELALNELVTLTCLAR | 47.66 | | | 173 |

Figure 10H

| Accession number | Protein name | Peptide sequence | Peptide score | Protein mass | Protein PI | Protein SEQ ID NO: |
|---|---|---|---|---|---|---|
| | | VPPPPPCCHPR | 40.20 | | | 174 |
| | | VPPPPPCCHPR | 45.19 | | | 174 |
| | | VPPPPPCCHPR | 26.36 | | | 174 |
| | | WLQGSQELPR | 56.29 | | | 175 |
| | | WLQGSQELPR | 53.97 | | | 175 |
| | | WLQGSQELPR | 70.58 | | | 175 |
| | | WLQGSQELPR | 56.29 | | | 175 |
| | | WLQGSQELPR | 45.92 | | | 175 |
| IPI00021263 | Hypothethical protein | DICNDVLSLLEK | 46.54 | 31711 | 4.94 | 176 |
| | | NLLSVAYK | 28.31 | | | 177 |
| IPI00418157 | Hypothetical protein DKFZp686E03231 | FGQGSGPIVLDDVR | 75.66 | 78766 | 5.95 | 168 |

Figure 11A

Table 6

Saliva proteins identified from both OSCC and healthy control subjects but exhibiting differential number of MS/MS spectra Accession IPI00003817
Protein name: Rho GDP-dissociation inhibitor 2
Protein mass: 22974    Protein PI: 5.1

| SEQ ID NO: | Peptides identified in OSCC | Peptide Score | SEQ ID NO: | Peptides identified in CTRL | Peptide Score |
|---|---|---|---|---|---|
| 178 | APEPHVEEDDDDELDSK | 54.15 | 182 | TLLGDGPVVTDPK | 47.65 |
| 179 | APNVVVTR | 40.57 | | | |
| 179 | APNVVVTR | 50.32 | | | |
| 179 | APNVVVTR | 50.15 | | | |
| 179 | APNVVVTR | 50.62 | | | |
| 179 | APNVVVTR | 47.01 | | | |
| 180 | DDESLIK | 51.91 | | | |
| 181 | ELQEMDK | 30.77 | | | |
| 182 | TLLGDGPVVTDPK | 65.52 | | | |
| 182 | TLLGDGPVVTDPK | 50.75 | | | |
| 182 | TLLGDGPVVTDPK | 67.14 | | | |
| 182 | TLLGDGPVVTDPK | 65.65 | | | |
| 182 | TLLGDGPVVTDPK | 50.23 | | | |

Figure 11B

Accession IPI00007047
Protein name: Calgranulin A
Protein mass: 10826    Protein PI: 6.51

| SEQ ID NO: | Peptides identified in OSCC | Peptide Score | SEQ ID NO: | Peptides identified in CTRL | Peptide Score |
|---|---|---|---|---|---|
| 183 | ALNSIIDVYHK | 67.93 | 183 | ALNSIIDVYHK | 58.8 |
| 183 | ALNSIIDVYHK | 42.71 | 183 | ALNSIIDVYHK | 42.94 |
| 183 | ALNSIIDVYHK | 43.09 | 183 | ALNSIIDVYHK | 30.43 |
| 183 | ALNSIIDVYHK | 25.55 | 183 | ALNSIIDVYHK | 31.2 |
| 183 | ALNSIIDVYHK | 67.75 | 183 | ALNSIIDVYHK | 37.58 |
| 183 | ALNSIIDVYHK | 33.93 | 183 | ALNSIIDVYHK | 23.21 |
| 183 | ALNSIIDVYHK | 50.97 | 183 | ALNSIIDVYHK | 30.43 |
| 183 | ALNSIIDVYHK | 53.35 | 184 | ELDINTDGAVNFQEFLILVIK | 46.39 |
| 184 | ELDINTDGAVNFQEFLILVIK | 50.55 | 184 | ELDINTDGAVNFQEFLILVIK | 49.89 |
| 184 | ELDINTDGAVNFQEFLILVIK | 93.41 | 184 | ELDINTDGAVNFQEFLILVIK | 47.46 |
| 184 | ELDINTDGAVNFQEFLILVIK | 25.25 | 184 | ELDINTDGAVNFQEFLILVIK | 34.79 |
| 184 | ELDINTDGAVNFQEFLILVIK | 41.45 | 184 | ELDINTDGAVNFQEFLILVIK | 23.57 |
| 184 | ELDINTDGAVNFQEFLILVIK | 48.67 | 184 | ELDINTDGAVNFQEFLILVIK | 49.36 |
| 184 | ELDINTDGAVNFQEFLILVIK | 40.24 | 184 | ELDINTDGAVNFQEFLILVIK | 52.64 |
| 184 | ELDINTDGAVNFQEFLILVIK | 39.15 | 184 | ELDINTDGAVNFQEFLILVIK | 46.39 |
| 184 | ELDINTDGAVNFQEFLILVIK | 34.77 | 185 | GADVWFK | 21.89 |
| 185 | GADVWFK | 36.82 | 185 | GADVWFK | 24.82 |
| 186 | GNFHAVYR | 29.66 | 185 | GADVWFK | 33.81 |
| 186 | GNFHAVYR | 40.61 | 185 | GADVWFK | 41.88 |
| 186 | GNFHAVYR | 30.94 | 185 | GADVWFK | 21.16 |

Figure 11C

| SEQ ID NO: | | | SEQ ID NO: | |
|---|---|---|---|---|
| 187 | GNFHAVYRDDLK | 33.89 | | |
| 188 | KGADVWFK | 41.49 | | |
| 189 | LLETECPQYIR | 39.39 | 189 | LLETECPQYIR | 66 |
| 189 | LLETECPQYIR | 92.03 | 189 | LLETECPQYIR | 50.9 |
| 189 | LLETECPQYIR | 68.03 | 189 | LLETECPQYIR | 68.36 |
| 189 | LLETECPQYIR | 82.65 | 190 | MLTELEK | 28.6 |
| 190 | MLTELEK | 31.88 | | |
| 190 | MLTELEK | 34.04 | | |
| 190 | MLTELEK | 25.43 | | |
| 190 | MLTELEK | 38.43 | | |
| 190 | MLTELEK | 37.71 | | |
| 190 | MLTELEK | 25.73 | | |

Accession IPI00027452
Protein name: Calgranulin B
Protein mass: 13234      Protein PI: 5.71

| SEQ ID NO: | Peptides identified in OSCC | Peptide Score | Peptide SEQ ID NO: | Peptides identified in CTRL | Peptide Score |
|---|---|---|---|---|---|
| 191 | DLQNFLK | 28.79 | 191 | DLQNFLK | 23.08 |
| 191 | DLQNFLK | 34.64 | 191 | DLQNFLK | 32.03 |
| 191 | DLQNFLK | 32.73 | 191 | DLQNFLK | 32.93 |
| 191 | DLQNFLK | 35.9 | 191 | DLQNFLK | 22.88 |

Figure 11D

| SEQ ID NO: | Peptides identified in OSCC | Peptide Score | SEQ ID NO: | Peptides identified in CTRL | Peptide Score |
|---|---|---|---|---|---|
| 191 | DLQNFLK | 26.6 | 191 | DLQNFLK | 29.37 |
| 191 | DLQNFLK | 37.53 | 191 | DLQNFLK | 29.34 |
| 191 | DLQNFLK | 29.11 | 192 | DLQNFLKK | 34.76 |
| 192 | DLQNFLKK | 25.4 | 193 | KDLQNFLK | 68.22 |
| 193 | KDLQNFLK | 69.67 | 193 | KDLQNFLK | 52.37 |
| 193 | KDLQNFLK | 69.6 | 194 | LGHPDTLNQGEFK | 60.49 |
| 193 | KDLQNFLK | 40.08 | 194 | LGHPDTLNQGEFK | 43.51 |
| 193 | KDLQNFLK | 42.31 | 194 | LGHPDTLNQGEFK | 52.87 |
| 193 | KDLQNFLK | 36.65 | 194 | LGHPDTLNQGEFK | 33 |
| 194 | LGHPDTLNQGEFK | 59.19 | 198 | NIETIINTHFQYSVK | 42.89 |
| 194 | LGHPDTLNQGEFK | 53.11 | 198 | NIETIINTHFQYSVK | 35.03 |
| 194 | LGHPDTLNQGEFK | 46.42 | 198 | NIETIINTHFQYSVK | 33.01 |
| 194 | LGHPDTLNQGEFK | 42.57 | 198 | NIETIINTHFQYSVK | 51.09 |
| 194 | LGHPDTLNQGEFK | 58.6 | 198 | NIETIINTHFQYSVK | 21.31 |
| 194 | LGHPDTLNQGEFK | 51.35 | | | |
| 194 | LGHPDTLNQGEFK | 29.28 | | | |
| 194 | LGHPDTLNQGEFK | 45.99 | | | |
| 194 | LGHPDTLNQGEFK | 35.95 | | | |
| 194 | LGHPDTLNQGEFK | 57.32 | | | |
| 194 | LGHPDTLNQGEFK | 55.76 | | | |
| 194 | LGHPDTLNQGEFK | 51.59 | | | |
| 194 | LGHPDTLNQGEFK | 35.1 | | | |
| 195 | LGHPDTLNQGEFKELVR | 78.47 | | | |
| 195 | LGHPDTLNQGEFKELVR | 49.4 | | | |

Figure 11E

| SEQ ID NO: | Peptides identified in OSCC | Peptide Score | Peptides identified in CTRL | Peptide Score |
|---|---|---|---|---|
| 195 | LGHPDTLNQGEFKELVR | 51.31 | | |
| 196 | LTWASHEK | 28.95 | | |
| 196 | LTWASHEK | 28.72 | | |
| 196 | LTWASHEK | 33.45 | | |
| 196 | LTWASHEK | 30.4 | | |
| 197 | MSQLER | 34.15 | | |
| 197 | MSQLER | 38.07 | | |
| 198 | NIETINTHFQYSVK | 80.32 | | |
| 198 | NIETINTHFQYSVK | 76.28 | | |
| 198 | NIETINTHFQYSVK | 58.7 | | |
| 198 | NIETINTHFQYSVK | 47.6 | | |
| 198 | NIETINTHFQYSVK | 51.18 | | |
| 198 | NIETINTHFQYSVK | 44.47 | | |
| 198 | NIETINTHFQYSVK | 45.82 | | |
| 198 | NIETINTHFQYSVK | 60.58 | | |
| 198 | NIETINTHFQYSVK | 28.25 | | |
| 198 | NIETINTHFQYSVK | 48.45 | | |
| 198 | NIETINTHFQYSVK | 43.64 | | |
| 198 | NIETINTHFQYSVK | 88.69 | | |
| 198 | NIETINTHFQYSVK | 44.73 | | |
| 199 | QLSFEEFIMLMAR | 79.18 | | |
| 199 | QLSFEEFIMLMAR | 35.05 | | |
| 199 | QLSFEEFIMLMAR | 53.24 | | |
| 199 | QLSFEEFIMLMAR | 30.69 | | |

Figure 11F

| SEQ ID NO: | Peptides identified in OSCC | Peptide Score | Peptides identified in CTRL | Peptide Score |
|---|---|---|---|---|
| 199 | QLSFEEFIMLMAR | 58.08 | | |
| 199 | QLSFEEFIMLMAR | 47.54 | | |
| 199 | QLSFEEFIMLMAR | 82.91 | | |
| 199 | QLSFEEFIMLMAR | 47.85 | | |
| 199 | QLSFEEFIMLMAR | 28.78 | | |
| 199 | QLSFEEFIMLMAR | 82.09 | | |

Figure 11G

| SEQ ID NO: | Peptides identified in OSCC | Peptide Score |
|---|---|---|
| 199 | QLSFEEFIMLMAR | 58.08 |
| 199 | QLSFEEFIMLMAR | 74.78 |
| 200 | VIEHIMEDLDTNADK | 105.27 |
| 200 | VIEHIMEDLDTNADK | 74.6 |
| 200 | VIEHIMEDLDTNADK | 75.35 |
| 201 | VIEHIMEDLDTNADKCLSFEEFIMLMAR | 25.45 |
| 201 | VIEHIMEDLDTNADKCLSFEEFIMLMAR | 48 |
| 201 | VIEHIMEDLDTNADKCLSFEEFIMLMAR | 58.65 |

| SEQ ID NO: | Peptides identified in CTRL | Peptide Score |
|---|---|---|

Accession IPI00376155
Protein name: Thymosin-like 4
Protein mass: 5110     Protein PI: 5.02

| SEQ ID NO: | Peptides identified in OSCC | Peptide Score |
|---|---|---|
| 202 | ETIEQEK | 29.58 |
| 203 | NPLPSKETIEQEK | 38.41 |
| 203 | NPLPSKETIEQEK | 60.64 |
| 204 | SDKPDMAEIEK | 55.66 |
| 204 | SDKPDMAEIEK | 29.47 |
| 204 | SDKPDMAEIEK | 31.87 |

| SEQ ID NO: | Peptides identified in CTRL | Peptide Score |
|---|---|---|
| 203 | NPLPSKETIEQEK | 50.05 |
| 204 | SDKPDMAEIEK | 30.75 |
| 205 | SDKPDMAEIEKFDK | 26.6 |

Figure 11H

| SEQ ID NO: | Peptides identified in OSCC | Peptide Score |
|---|---|---|
| 204 | SDKPDMAEIEK | 72.3 |
| 205 | SDKPDMAEIEKFDK | 60.92 |
| 205 | SDKPDMAEIEKFDK | 40.25 |
| 205 | SDKPDMAEIEKFDK | 72.74 |
| 205 | SDKPDMAEIEKFDK | 34.66 |
| 205 | SDKPDMAEIEKFDK | 90.84 |
| 205 | SDKPDMAEIEKFDK | 49.03 |

| SEQ ID NO: | Peptides identified in CTRL | Peptide Score |
|---|---|---|

Accession IPI00216691
Protein name: Profilin I
Protein mass: 19382          Protein PI: 9.51

| SEQ ID NO: | Peptides identified in OSCC | Peptide Score |
|---|---|---|
| 206 | DSLLQDGEFSMDLR | 117.59 |
| 207 | DSPSVWAAVPGK | 61.05 |
| 207 | DSPSVWAAVPGK | 37.25 |
| 208 | EGVHGGLINK | 44.17 |
| 209 | SSFYVNGLTLGGQK | 41.74 |
| 210 | STGGAPTFMVTVTK | 35.74 |
| 210 | STGGAPTFMVTVTK | 49.27 |
| 210 | STGGAPTFMVTVTK | 75.24 |
| 210 | TDKTLVLLMGK | 35.4 |
| 211 | TDKTLVLLMGK | 68.45 |

| SEQ ID NO: | Peptides identified in CTRL | Peptide Score |
|---|---|---|
| 207 | DSPSVWAAVPGK | 35.06 |
| 207 | DSPSVWAAVPGK | 53.89 |

Figure 11I

| SEQ ID NO: | Peptides identified in OSCC | Peptide Score |
|---|---|---|
| 212 | TFVNITPAEVGVLVGK | 34.35 |
| 212 | TFVNITPAEVGVLVGK | 62.94 |
| 213 | TLVLLMGK | 55.7 |
| 213 | TLVLLMGK | 53.38 |

| SEQ ID NO: | Peptides identified in CTRL | Peptide Score |
|---|---|---|

Accession IPI0299729
Protein name: Transcobalamin I
Protein mass: 48164    Protein PI: 4.96

| SEQ ID NO: | Peptides identified in OSCC | Peptide Score |
|---|---|---|
| 214 | GTSAVNVVLSLK | 57.92 |
| 214 | GTSAVNVVLSLK | 54.48 |
| 215 | LKPLLNTMIQSNYNR | 63.8 |
| 215 | LKPLLNTMIQSNYNR | 42.37 |
| 215 | LKPLLNTMIQSNYNR | 74.29 |
| 216 | LVGIQIQTLMQK | 49.05 |
| 217 | NGENLEVR | 68.35 |

| SEQ ID NO: | Peptides identified in CTRL | Peptide Score |
|---|---|---|
| 224 | LSDVSSGELALILALGVCR | 21.07 |
| 225 | TFLDINK | 26.83 |
| 226 | TYWELLSGGEPLSQGAGSYVVR | 36.37 |

Figure 11J

Accession IPI00304557
Protein name: Short palate, lung and nasal epithelium carcinoma associated protein 2
Protein mass: 26996    Protein PI: 5.35

| SEQ ID NO: | Peptides identified in OSCC | Peptide Score | SEQ ID NO: | Peptides identified in CTRL | Peptide Score |
|---|---|---|---|---|---|
| 218 | FVNSVINTLK | 64.89 | 227 | EICPLIR | 20.59 |
| 218 | FVNSVINTLK | 58.85 | 219 | ISNSLILDVK | 29.86 |
| 218 | FVNSVINTLK | 50.41 | 220 | LLPTNTDIFGLK | 48.53 |
| 218 | FVNSVINTLK | 48.15 | 222 | TQLQTLI | 32.56 |
| 219 | ISNSLILDVK | 84.95 | | | |
| 219 | ISNSLILDVK | 75.24 | | | |
| 220 | LLPTNTDIFGLK | 68.55 | | | |
| 221 | STVSSLLQK | 35.71 | | | |
| 221 | STVSSLLQK | 36.02 | | | |
| 222 | TQLQTLI | 39.36 | | | |
| 222 | TQLQTLI | 42.58 | | | |

Accession IPI00305457
Protein name: Alpha-1-antitrypsin
Protein mass: 48208    Protein PI: 5.19

| SEQ ID NO: | Peptides identified in OSCC | Peptide Score | SEQ ID NO: | Peptides identified in CTRL | Peptide Score |
|---|---|---|---|---|---|
| 223 | AVLTIDEK | 62.29 | 228 | LYHSEAFTVNFGDTEEAKK | 38.54 |

Figure 11K

| SEQ ID NO: | Peptides identified in OSCC | Peptide Score |
|---|---|---|
| 223 | AVLTIDEK | 47.28 |
| 229 | DTVFALVNYIFFK | 33.11 |
| 229 | DTVFALVNYIFFK | 73.41 |
| 229 | DTVFALVNYIFFK | 73.67 |
| 230 | ELDRDTVFALVNYIFFK | 44.23 |
| 230 | ELDRDTVFALVNYIFFK | 49.65 |
| 230 | ELDRDTVFALVNYIFFK | 61.51 |
| 231 | FNKPFVFLMIEQNTK | 38.94 |
| 231 | FNKPFVFLMIEQNTK | 55.99 |
| 231 | FNKPFVFLMIEQNTK | 49.64 |
| 231 | FNKPFVFLMIEQNTK | 43.62 |
| 232 | LQHLENELTHDIITK | 61.39 |
| 232 | LQHLENELTHDIITK | 25.17 |
| 232 | LQHLENELTHDIITK | 28.61 |
| 232 | LQHLENELTHDIITK | 74.52 |
| 232 | LQHLENELTHDIITK | 70.31 |
| 232 | LQHLENELTHDIITK | 31.04 |
| 233 | LSITGTYDLK | 70.45 |
| 233 | LSITGTYDLK | 80.35 |
| 233 | LSITGTYDLK | 84.15 |
| 233 | LSITGTYDLK | 59.85 |
| 233 | LSITGTYDLK | 64.19 |
| 233 | LSITGTYDLK | 80.41 |
| 233 | LSITGTYDLK | 62.55 |

| SEQ ID NO: | Peptides identified in CTRL | Peptide Score |
|---|---|---|
| 237 | SPLFMGK | 33.18 |
| 238 | SVLGQLGITK | 23.22 |

Figure 11L

| SEQ ID NO: | Peptides identified in OSCC | Peptide Score | Peptides identified in CTRL | Peptide Score |
|---|---|---|---|---|
| 234 | LSSWVLLMK | 39.4 | | |
| 234 | LSSWVLLMK | 25.38 | | |
| 235 | LVDKFLEDVK | 31.93 | | |
| 228 | LYHSEAFTVNFGDTEEAKK | 40.67 | | |
| 236 | QINDYVEK | 29.05 | | |
| 236 | QINDYVEK | 50.01 | | |
| 236 | QINDYVEK | 31.35 | | |
| 236 | QINDYVEK | 47.08 | | |
| 237 | SPLFMGK | 39.5 | | |
| 237 | SPLFMGK | 34.14 | | |
| 237 | SPLFMGK | 38.8 | | |
| 237 | SPLFMGK | 40.81 | | |
| 237 | SPLFMGK | 34.18 | | |
| 238 | SVLGQLGITK | 42.2 | | |
| 238 | SVLGQLGITK | 48.9 | | |
| 238 | SVLGQLGITK | 76.5 | | |
| 238 | SVLGQLGITK | 53.85 | | |
| 238 | SVLGQLGITK | 44.78 | | |
| 238 | SVLGQLGITK | 25.75 | | |
| 239 | TLNQFDSQLQLTTGNGLFLSEQLK | 77.55 | | |
| 240 | VFSNGADLSGVTEEAPLK | 114.17 | | |
| 240 | VFSNGADLSGVTEEAPLK | 105.99 | | |
| 240 | VFSNGADLSGVTEEAPLK | 50.1 | | |
| 240 | VFSNGADLSGVTEEAPLK | 95.44 | | |

Figure 11M

| SEQ ID NO: | Peptides identified in OSCC | Peptide Score |
|---|---|---|
| 240 | VFSNGADLSGVTEEAPLK | 95.35 |
| 240 | VFSNGADLSGVTEEAPLK | 85.93 |
| 240 | VFSNGADLSGVTEEAPLK | 122.29 |
| 240 | VFSNGADLSGVTEEAPLK | 139.2 |
| 241 | VVNPTQK | 39.08 |

Accession iPI00337654
Protein name: Prothymosin alpha
Protein mass: 8156    Protein PI: 3.72

| SEQ ID NO: | Peptides identified in OSCC | Peptide Score | SEQ ID NO: | Peptides identified in CTRL | Peptide Score |
|---|---|---|---|---|---|
| 242 | SDAAVDTSSEITTK | 77.54 | 242 | SDAAVDTSSEITTK | 69.01 |

Figure 11N

| SEQ ID NO: | Peptides identified in OSCC | Peptide Score | SEQ ID NO: | Peptides identified in CTRL | Peptide Score |
|---|---|---|---|---|---|
| 242 | SDAAVDTSSEITTK | 50.64 | | | |
| 242 | SDAAVDTSSEITTK | 50.74 | | | |

Accession IPI00012011
Protein name: Cofilin 1 (non-muscle)
Protein mass: 18491    Protein PI: 8.22

| SEQ ID NO: | Peptides identified in OSCC | Peptide Score | SEQ ID NO: | Peptides identified in CTRL | Peptide Score |
|---|---|---|---|---|---|
| 243 | ASGVAVSDGVIK | 63.48 | 243 | ASGVAVSDGVIK | 54.47 |
| 243 | ASGVAVSDGVIK | 49.35 | 243 | ASGVAVSDGVIK | 21.91 |
| 243 | ASGVAVSDGVIK | 63.84 | 243 | ASGVAVSDGVIK | 73.75 |
| 243 | ASGVAVSDGVIK | 73.78 | 243 | ASGVAVSDGVIK | 51.4 |
| 243 | ASGVAVSDGVIK | 62.77 | | | |
| 243 | ASGVAVSDGVIK | 65.98 | | | |
| 244 | VFNDMK | 27.49 | | | |

Figure 11O

Accession IPI00218918
Protein name: Annexin I
Protein mass: 38690          Protein PI: 6.57

| SEQ ID NO: | Peptides identified in OSCC | Peptide Score | SEQ ID NO: | Peptides identified in CTRL |
|---|---|---|---|---|
| 245 | AMVSEFLK | 46.7 | 245 | AMVSEFLK |
| 245 | AMVSEFLK | 47.6 | 245 | AMVSEFLK |
| 245 | AMVSEFLK | 51.91 | | |
| 245 | AMVSEFLK | 35.77 | | |
| 245 | AMVSEFLK | 48.58 | | |
| 245 | AMVSEFLK | 47.53 | | |
| 246 | NALLSLAK | 32.24 | | |
| 246 | NALLSLAK | 45.61 | | |

Accession IPI00021841
Protein name: Apolipoprotein A-I
Protein mass: 30759          Protein PI: 5.56

| SEQ ID NO: | Peptides identified in OSCC | Peptide Score | SEQ ID NO: | Peptides identified in CTRL |
|---|---|---|---|---|
| 305 | ATEHLSTISEK | 26.71 | 250 | DYVSQFEGSALGK |
| 248 | DLATVYDVLK | 41.43 | 252 | QGLLPVLESFK |
| 249 | DSGRDYVSQFEGSALGK | 54.23 | 252 | QGLLPVLESFK |
| 250 | DYVSQFEGSALGK | 71.85 | 253 | THLAPYSDELR |
| 250 | DYVSQFEGSALGK | 53.4 | 256 | VSFLSALEEYTK |

Figure 11P

| SEQ ID NO: | Peptides identified in OSCC | Peptide Score |
|---|---|---|
| 250 | DYVSQFEGSALGK | 60.27 |
| 251 | LSPLGEEMR | 51.94 |
| 252 | QGLLPVLESFK | 59.38 |
| 252 | QGLLPVLESFK | 57.24 |
| 252 | QGLLPVLESFK | 54.84 |
| 253 | THLAPYSDELR | 62.57 |
| 254 | VKDLATVYVDVLK | 32.8 |
| 255 | VQPYLDDFQK | 26.04 |
| 256 | VSFLSALEEYTK | 78.88 |
| 256 | VSFLSALEEYTK | 78.88 |

Accession IPI00376154
Protein name: 5 kDa protein
Protein mass: 5037    Protein PI: 6.21

| SEQ ID NO: | Peptides identified in OSCC | Peptide Score | SEQ ID NO: | Peptides identified in CTRL | Peptide Score |
|---|---|---|---|---|---|
| 257 | SDKPDMAEIEK | 29.47 | 257 | SDKPDMAEIEK | 30.75 |
| 257 | SDKPDMAEIEK | 32.01 | 258 | SDKPDMAEIEKFDK | 24.23 |
| 257 | SDKPDMAEIEK | 55.66 | 258 | SDKPDMAEIEKFDK | 26.6 |
| 258 | SDKPDMAEIEKFDK | 90.84 | 258 | SDKPDMAEIEKFDK | 43.5 |
| 258 | SDKPDMAEIEKFDK | 34.66 | 258 | SDKPDMAEIEKFDK | 38.17 |
| 258 | SDKPDMAEIEKFDK | 72.74 | 259 | TETQEKNPLPSK | 38.81 |
| 258 | SDKPDMAEIEKFDK | 49.03 | 259 | TETQEKNPLPSK | |

Figure 11Q

| SEQ ID NO: | Peptides identified in OSCC | Peptide Score |
|---|---|---|
| 258 | SDKPDMAEIEKFDK | 50.7 |
| 258 | SDKPDMAEIEKFDK | 55.79 |
| 258 | SDKPDMAEIEKFDK | 30.91 |
| 258 | SDKPDMAEIEKFDK | 42.23 |
| 258 | SDKPDMAEIEKFDK | 49.2 |
| 259 | TETQEKNPLPSK | 43.4 |

| SEQ ID NO: | Peptides identified in CTRL | Peptide Score |
|---|---|---|

Accession IPI00171411
Protein name: Golgi membrane protein GP73
Protein mass: 49768    Protein PI: 5.04

| SEQ ID NO: | Peptides identified in OSCC | Peptide Score |
|---|---|---|
| 260 | DTINLLDQR | 58.13 |

| SEQ ID NO: | Peptides identified in CTRL | Peptide Score |
|---|---|---|
| 260 | DTINLLDQR | 49.68 |
| 260 | DTINLLDQR | 44.47 |
| 262 | IQSSHNFQLESVNK | 29.39 |
| 263 | LQQDVLQFQK | 31.1 |

Figure 11R

Accession IPI00075248
Protein name: Calmodulin
Protein mass: 17152      Protein PI: 4.05

| SEQ ID NO: | Peptides identified in OSCC | Peptide Score | SEQ ID NO: | Peptides identified in CTRL | Peptide Score |
|---|---|---|---|---|---|
| 261 | ELGTVMR | 48.65 | 264 | ADQLTEEQIAEFK | 52.53 |
|  |  |  | 264 | ADQLTEEQIAEFK | 53.94 |
|  |  |  | 265 | EAFSLFDKDGDGTITTK | 34.66 |
|  |  |  | 265 | EAFSLFDKDGDGTITTK | 44.13 |

Figure 11S

Accession IPI00019036
Protein name: Lysozyme C
Protein mass: 16526          Protein PI: 9.38

| SEQ ID NO: | Peptides identified in OSCC | Peptide Score | SEQ ID NO: | Peptides identified in CTRL | Peptide Score |
|---|---|---|---|---|---|
| 266 | ATNYNAGDR | 51.31 | 267 | AWVAWR | 36.83 |
| 266 | ATNYNAGDR | 33.08 | 267 | AWVAWR | 27.04 |
| 267 | AWVAWR | 33.48 | 267 | AWVAWR | 33.21 |
| 267 | AWVAWR | 27.67 | 267 | AWVAWR | 34.33 |
| 268 | LGMDGYR | 37.54 | 280 | QYVQGCGV | 23.2 |
| 268 | LGMDGYR | 38.99 | 280 | QYVQGCGV | 31.48 |
| 268 | LGMDGYR | 38.39 | 280 | QYVQGCGV | 21.72 |
| 269 | STDYGIFQINSR | 70.4 | 269 | STDYGIFQINSR | 70.38 |
| 270 | WESGYNTR | 26.07 | 269 | STDYGIFQINSR | 66.57 |
| 270 | WESGYNTR | 30.3 | 269 | STDYGIFQINSR | 70.87 |
| 270 | WESGYNTR | 27.12 | 269 | STDYGIFQINSR | 57.08 |
|  |  |  | 269 | STDYGIFQINSR | 69.75 |
|  |  |  | 269 | STDYGIFQINSR | 58.12 |
|  |  |  | 269 | STDYGIFQINSR | 74.91 |
|  |  |  | 269 | STDYGIFQINSR | 68.38 |
|  |  |  | 269 | STDYGIFQINSR | 46.74 |
|  |  |  | 281 | TFGAVNAGHLSQSALLQDNIADAVACAK | 78.06 |
|  |  |  | 281 | TFGAVNAGHLSQSALLQDNIADAVACAK | 107.15 |

Figure 11T

| Peptides identified in OSCC | Peptide Score | SEQ ID NO: | Peptides identified in CTRL | Peptide Score |
|---|---|---|---|---|
| | | 281 | TFGAVNAGHLSQSALLQDNIADAVACAK | 81.57 |
| | | 270 | WESGYNTR | 30.58 |

Accession IPI00004656
Protein name: Beta-2-microglobulin
Protein mass: 13706   Protein PI: 6.06

| SEQ ID NO: | Peptides identified in OSCC | Peptide Score | SEQ ID NO: | Peptides identified in CTRL | Peptide Score |
|---|---|---|---|---|---|
| 271 | VEHSDLSFSK | 29.34 | 282 | IQVYSR | 31.58 |
| 271 | VEHSDLSFSK | 33.63 | 282 | IQVYSR | 32.63 |
| 272 | VNHVTLSQPK | 35.01 | 282 | IQVYSR | 26.76 |
| | | | 271 | VEHSDLSFSK | 38.59 |
| | | | 271 | VEHSDLSFSK | 22.28 |
| | | | 271 | VEHSDLSFSK | 30.53 |
| | | | 272 | VNHVTLSQPK | 33.78 |
| | | | 272 | VNHVTLSQPK | 35.5 |
| | | | 272 | VNHVTLSQPK | 27.57 |
| | | | 272 | VNHVTLSQPK | 25.2 |

Figure 11U

Accession IPI00304806
Protein name: Kallikrein 1
Protein mass: 28871    Protein PI: 4.62

| SEQ ID NO: | Peptides identified in OSCC | Peptide Score |
|---|---|---|
| 273 | LTEPADTITDAVK | 75.23 |
| 273 | LTEPADTITDAVK | 69.91 |

| SEQ ID NO: | Peptides identified in CTRL | Peptide Score |
|---|---|---|
| 283 | ILPNDECEK | 26.48 |
| 283 | ILPNDECEK | 30.39 |
| 283 | ILPNDECEK | 37.46 |
| 283 | ILPNDECEK | 24.12 |
| 273 | LTEPADTITDAVK | 62.09 |
| 273 | LTEPADTITDAVK | 29.87 |
| 273 | LTEPADTITDAVK | 54.14 |
| 284 | QADEDYSHDLMLLR | 22.92 |
| 284 | QADEDYSHDLMLLR | 27.32 |

Accession IPI00004573
Protein name: Polymeric-immunoglobulin receptor
Protein mass: 83262    Protein PI: 6.58

| SEQ ID NO: | Peptides identified in OSCC | Peptide Score |
|---|---|---|
| 274 | AFVNCDENSR | 52.68 |
| 275 | ASVDSGSSEEQGGSSR | 91.29 |
| 275 | ASVDSGSSEEQGGSSR | 98.28 |
| 275 | ASVDSGSSEEQGGSSR | 78.33 |

| SEQ ID NO: | Peptides identified in CTRL | Peptide Score |
|---|---|---|
| 274 | AFVNCDENSR | 40.68 |
| 274 | AFVNCDENSR | 40.68 |
| 275 | ASVDSGSSEEQGGSSR | 84.68 |
| 275 | ASVDSGSSEEQGGSSR | 103.48 |

Figure 11V

| SEQ ID NO: | Peptides identified in OSCC | Peptide Score | Peptide SEQ ID NO: | Peptides identified in CTRL | Peptide Score |
|---|---|---|---|---|---|
| 275 | ASVDSGSSEEQGGSSR | 122.3 | 285 | CGLGINSR | 40.02 |
| 276 | IIEGEPNLK | 34.75 | 285 | CGLGINSR | 40.02 |
| 277 | IILNPQDK | 32.88 | 286 | CPLLVDSEGWVK | 68.59 |
| 278 | QGHFYGETAAVYVAVEER | 42.54 | 286 | CPLLVDSEGWVK | 68.59 |
| 278 | QGHFYGETAAVYVAVEER | 40.76 | 287 | GGCITLISSEGYVSSK | 64.62 |
| 278 | QGHFYGETAAVYVAVEER | 44.56 | 287 | GGCITLISSEGYVSSK | 59.19 |
| 278 | QGHFYGETAAVYVAVEER | 49.29 | 288 | GSVTFHCALGFEVANVAK | 22.65 |
| 278 | QGHFYGETAAVYVAVEER | 43.54 | 288 | GSVTFHCALGFEVANVAK | 22.65 |
| 279 | VLDSGFR | 35.78 | 289 | GVAGSSVAVLQPYNR | 48.45 |
| 279 | VLDSGFR | 34.7 | 289 | GVAGSSVAVLQPYNR | 48.45 |
| 279 | VLDSGFR | 35.6 | 276 | IIEGEPNLK | 26.72 |

Figure 11W

| SEQ ID NO: | Peptides identified in OSCC | Peptide Score | SEQ ID NO: | Peptides identified in CTRL | Peptide Score |
|---|---|---|---|---|---|
| 279 | VLDSGFR | 32.61 | 276 | IIEGEPNLK | 26.72 |
| 279 | VLDSGFR | 34.28 | 277 | ILLNPQDK | 23.41 |
| 291 | VYTVDLGR | 37.48 | 277 | ILLNPQDK | 23.41 |
| 291 | VYTVDLGR | 40.5 | 278 | QGHFYGETAAVYVAVEER | 60.01 |
| 291 | VYTVDLGR | 40.74 | 278 | QGHFYGETAAVYVAVEER | 64.21 |
| 291 | VYTVDLGR | 45.07 | 278 | QGHFYGETAAVYVAVEER | 63.49 |
| 291 | VYTVDLGR | 40.87 | 278 | QGHFYGETAAVYVAVEER | 59.49 |
| 291 | VYTVDLGR | 40.49 | 296 | QSSGENCDVVVNTLGK | 81.36 |
| 291 | VYTVDLGR | 40.95 | 296 | QSSGENCDVVVNTLGK | 78.9 |
| | | | 296 | QSSGENCDVVVNTLGK | 72.27 |
| | | | 296 | QSSGENCDVVVNTLGK | 69.04 |
| | | | 297 | TVTINCPFK | 36.42 |
| | | | 297 | TVTINCPFK | 30.9 |
| | | | 297 | TVTINCPFK | 36.42 |
| | | | 297 | TVTINCPFK | 45.34 |
| | | | 297 | TVTINCPFK | 43.76 |
| | | | 297 | TVTINCPFK | 48.4 |
| | | | 297 | TVTINCPFK | 40.12 |
| | | | 297 | TVTINCPFK | 50.44 |
| | | | 279 | VLDSGFR | 34.23 |
| | | | 279 | VLDSGFR | 35.95 |
| | | | 279 | VLDSGFR | 36.39 |
| | | | 279 | VLDSGFR | 36.56 |
| | | | 279 | VLDSGFR | 21.7 |

Figure 11X

| Peptides identified in OSCC | Peptide Score | SEQ ID NO: | Peptides identified in CTRL | Peptide Score |
|---|---|---|---|---|
| | | 279 | VLDSGFR | 27.33 |
| | | 279 | VLDSGFR | 32.22 |
| | | 279 | VLDSGFR | 32.57 |
| | | 279 | VLDSGFR | 32.8 |
| | | 279 | VLDSGFR | 32.8 |
| | | 279 | VLDSGFR | 30.2 |
| | | 291 | VYTVDLGR | 39.79 |
| | | 291 | VYTVDLGR | 44.31 |
| | | 291 | VYTVDLGR | 40.59 |
| | | 291 | VYTVDLGR | 39.79 |

Accession IPI00414173
Protein name: 50 kDa protein
Protein mass: 50134    Protein PI: 4.81

| SEQ ID NO: | Peptides identified in OSCC | Peptide Score | SEQ ID NO: | Peptides identified in CTRL | Peptide Score |
|---|---|---|---|---|---|
| 292 | EVATNSELVQSGK | 68.57 | 165 | DAEDWFFSK | 33.87 |
| 293 | LASYLDK | 40.78 | 165 | DAEDWFFSK | 47.44 |
| 294 | LASYLDKVR | 63.75 | 165 | DAEDWFFSK | 51.02 |
| 295 | VLDELTLAR | 60.36 | 292 | EVATNSELVQSGK | 100.16 |
| | | | 292 | EVATNSELVQSGK | 100.01 |
| | | | 292 | EVATNSELVQSGK | 100.26 |
| | | | 298 | GSCGIGGGIGGGSSR | 51.6 |

Figure 11Y

| Peptides identified in OSCC | Peptide SEQ ID NO: | Peptides identified in CTRL | Peptide Score |
|---|---|---|---|
| | 299 | ISSVLAGGSCR | 53.65 |
| | 299 | ISSVLAGGSCR | 62.14 |
| | 299 | ISSVLAGGSCR | 61.15 |
| | 293 | LASYLDK | 40.79 |
| | 293 | LASYLDK | 47.95 |
| | 293 | LASYLDK | 40.91 |
| | 295 | VLDELTLAR | 46.83 |
| | 295 | VLDELTLAR | 54.7 |

Accession IPI00412853
Protein name: 78 kDa protein
Protein mass: 76396    Protein PI: 5.75

| SEQ ID NO: | Peptides identified in OSCC | Peptide Score | SEQ ID NO: | Peptides identified in CTRL | Peptide Score |
|---|---|---|---|---|---|
| 125 | FGQGSGPIVLDDVR | 62.6 | 125 | FGQGSGPIVLDDVR | 100.42 |
| | | | 125 | FGQGSGPIVLDDVR | 43.8 |
| | | | 125 | FGQGSGPIVLDDVR | 88.74 |
| | | | 125 | FGQGSGPIVLDDVR | 100.73 |

Figure 11Z

| Peptides identified in OSCC | Peptide SEQ ID NO: | Peptides identified in CTRL | Peptide Score |
|---|---|---|---|
| | 125 | FGQGSGPIVLDDVR | 88.57 |
| | 125 | FGQGSGPIVLDDVR | 144.64 |
| | 125 | FGQGSGPIVLDDVR | 85.65 |
| | 125 | FGQGSGPIVLDDVR | 55.26 |
| | 125 | FGQGSGPIVLDDVR | 43.8 |
| | 125 | FGQGSGPIVLDDVR | 31.28 |
| | 171 | VEVLYR | 35.55 |
| | 171 | VEVLYR | 34.69 |
| | 171 | VEVLYR | 34.48 |
| | 171 | VEVLYR | 37 |
| | 171 | VEVLYR | 31.26 |
| | 171 | VEVLYR | 36.97 |
| | 171 | VEVLYR | 36.72 |
| | 171 | VEVLYR | 41.43 |

Accession IPI00477859
Protein name: 83 kDa protein
Protein mass: 83386    Protein PI: 4.78

| SEQ ID NO: | Peptides identified in OSCC | Peptide Score | SEQ ID NO: | Peptides identified in CTRL | Peptide Score |
|---|---|---|---|---|---|
| 125 | FGQGSGPIVLDDVR | 91.64 | 125 | FGQGSGPIVLDDVR | 98.42 |
| 126 | VEILYR | 29.89 | 125 | FGQGSGPIVLDDVR | 115.36 |
| 126 | VEILYR | 42.06 | 125 | FGQGSGPIVLDDVR | 106.6 |

Figure 11AA

| Peptides identified in OSCC | Peptide SEQ ID NO: | Peptides identified in CTRL | Peptide Score |
|---|---|---|---|
| | 125 | FGQGSGPIVLDDVR | 59.91 |
| | 125 | FGQGSGPIVLDDVR | 72.57 |
| | 125 | FGQGSGPIVLDDVR | 83.4 |
| | 125 | FGQGSGPIVLDDVR | 90.54 |
| | 125 | FGQGSGPIVLDDVR | 87.2 |
| | 125 | FGQGSGPIVLDDVR | 67.69 |
| | 300 | INLGFSNLK | 46.2 |
| | 170 | QLGCGWATSAPGNAR | 33.23 |
| | 170 | QLGCGWATSAPGNAR | 63.43 |
| | 170 | QLGCGWATSAPGNAR | 48.08 |
| | 170 | QLGCGWATSAPGNAR | 55.83 |
| | 126 | VEILYR | 41.14 |
| | 126 | VEILYR | 39.5 |
| | 126 | VEILYR | 31.41 |
| | 126 | VEILYR | 31.96 |
| | 126 | VEILYR | 32.95 |
| | 126 | VEILYR | 31.51 |
| | 126 | VEILYR | 36.06 |
| | 126 | VEILYR | 31.97 |
| | 126 | VEILYR | 36.04 |
| | 126 | VEILYR | 35.81 |
| | 126 | VEILYR | 36.99 |
| | 126 | VEILYR | 36.84 |
| | 126 | VEILYR | 36.97 |

Figure 11BB

Accession IPI00412929
Protein name: 169 kDa protein
Protein mass: 168902	Protein PI: 5.63

| SEQ ID NO: | Peptides identified in OSCC | Peptide Score | SEQ ID NO: | Peptides identified in CTRL | Peptide Score |
|---|---|---|---|---|---|
| 125 | FGQGSGPIVLDDVR | 82.22 | 125 | FGQGSGPIVLDDVR | 105.43 |
| 125 | FGQGSGPIVLDDVR | 83.03 | 125 | FGQGSGPIVLDDVR | 120.05 |
| 126 | VEILYR | 41.18 | 125 | FGQGSGPIVLDDVR | 120.75 |
| 126 | VEILYR | 35.65 | 125 | FGQGSGPIVLDDVR | 120.75 |
|  |  |  | 125 | FGQGSGPIVLDDVR | 60.51 |
|  |  |  | 301 | FPSVYLR | 38.86 |
|  |  |  | 300 | INLGFSNLK | 51.43 |
|  |  |  | 300 | INLGFSNLK | 46.33 |
|  |  |  | 170 | QLGCGWATSAPGNAR | 67.28 |
|  |  |  | 170 | QLGCGWATSAPGNAR | 51.74 |
|  |  |  | 170 | QLGCGWATSAPGNAR | 48.87 |
|  |  |  | 170 | QLGCGWATSAPGNAR | 67.76 |
|  |  |  | 171 | VEILYR | 41.92 |
|  |  |  | 171 | VEILYR | 37 |
|  |  |  | 126 | VEILYR | 24.91 |
|  |  |  | 126 | VEILYR | 36.89 |
|  |  |  | 126 | VEILYR | 36.76 |
|  |  |  | 126 | VEILYR | 38.26 |

Fig. 12
Table 7
Immunoassay validation of salivary proteins differentially expressed in OSCC and healthy control subjects

| Protein | Fold change (mean level) | P | Validation method |
|---|---|---|---|
| M2BP | 1.99 | 0.006 | ELISA |
| Profilin | 1.93 | 0.0003 | Immunoblotting |
| CD59 | 2.45 | 0.00001 | Immunoblotting |
| MRP14 | 2.15 | 0.000002 | Immunoblotting |
| Catalase | 2.07 | 0.0000005 | Immunoblotting |
| Histone H1 | 1.10 | 0.92 | ELISA |
| S100A12 | 1.01 | 0.82 | ELISA |
| Ras-related protein Rab-7 | 1.12 | 0.61 | Immunoblotting |
| Moesin | 1.19 | 0.32 | Immunoblotting |
| Involucrin | 1.67 | 0.11 | ELISA |
| S100P | 1.24 | 0.05 | ELISA |
| Hematopoietic lineage cell-specific protein | 1.43 | 0.002 | Immunoblotting |

Note: M2BP, MRP14, CD59, Profilin, and catalase were validated on a new group of OSCC patients ($n = 48$) and matched control subjects ($n = 48$). The rest of the proteins were validated on 20 OSCC and 20 matched control subjects.

SEQUENCE LISTING

```
<160> NUMBER OF SEQ ID NOS: 305

<210> SEQ ID NO 1
<211> LENGTH: 9
<212> TYPE: PRT
<213> ORGANISM: Artificial Sequence
<220> FEATURE:
<223> OTHER INFORMATION: synthetic squamous cell carcinoma antigen 2
      tryptic digest peptide

<400> SEQUENCE: 1

Thr Asn Ser Ile Leu Phe Tyr Gly Arg
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic CD59 glycoprotein (CD59) tryptic
      digest peptide

<400> SEQUENCE: 2

Ala Gly Leu Gln Val Tyr Asn Lys
1               5

<210> SEQ ID NO 3
<211> LENGTH: 14
<212> TYPE: PRT
<213> ORGANISM: Artificial Sequence
<220> FEATURE:
<223> OTHER INFORMATION: synthetic involucrin (IVL) tryptic digest
      peptide

<400> SEQUENCE: 3

His Leu Val Gln Gln Glu Gly Gln Leu Glu Gln Gln Glu Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic Ras-related protein Rab-7 (RAB7A)
      tryptic digest peptide

<400> SEQUENCE: 4

Val Ile Ile Leu Gly Asp Ser Gly Val Gly Lys
1               5                   10

<210> SEQ ID NO 5
```

<211> LENGTH: 12
<212> TYPE: PRT
<213> ORGANISM: Artificial Sequence
<220> FEATURE:
<223> OTHER INFORMATION: synthetic Mac-2 binding protein (M2BP, Mac-2
      BP, s90K, 90K) tryptic digest peptide

<400> SEQUENCE: 5

Ala Ser His Glu Glu Val Glu Gly Leu Val Glu Lys
1               5                   10

<210> SEQ ID NO 6
<211> LENGTH: 9
<212> TYPE: PRT
<213> ORGANISM: Artificial Sequence
<220> FEATURE:
<223> OTHER INFORMATION: synthetic Mac-2 binding protein (M2BP, Mac-2
      BP, s90K, 90K) tryptic digest peptide

<400> SEQUENCE: 6

Ile Asp Ile Thr Leu Ser Ser Val Lys
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic Mac-2 binding protein (M2BP, Mac-2
      BP, s90K, 90K) tryptic digest peptide

<400> SEQUENCE: 7

Arg Ile Asp Ile Thr Leu Ser Ser Val Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: synthetic Mac-2 binding protein (M2BP, Mac-2
      BP, s90K, 90K) tryptic digest peptide

<400> SEQUENCE: 8

Ser Asp Leu Ala Val Pro Ser Glu Leu Ala Leu Leu Lys
1               5                   10

<210> SEQ ID NO 9
<211> LENGTH: 17
<212> TYPE: PRT
<213> ORGANISM: Artificial Sequence
<220> FEATURE:
<223> OTHER INFORMATION: synthetic Mac-2 binding protein (M2BP, Mac-2
      BP, s90K, 90K) tryptic digest peptide

<400> SEQUENCE: 9

Thr Leu Gln Ala Leu Glu Phe His Thr Val Pro Phe Gln Leu Leu Ala
1               5                   10                  15

Arg

<210> SEQ ID NO 10
<211> LENGTH: 9
<212> TYPE: PRT
<213> ORGANISM: Artificial Sequence
<220> FEATURE:
<223> OTHER INFORMATION: synthetic SH3 domain-binding glutamic acid-
      rich-like protein (SH3BGRL) tryptic digest peptide

```
<400> SEQUENCE: 10

Asp Ile Ala Ala Asn Glu Glu Asn Arg
1               5

<210> SEQ ID NO 11
<211> LENGTH: 10
<212> TYPE: PRT
<213> ORGANISM: Artificial Sequence
<220> FEATURE:
<223> OTHER INFORMATION: synthetic SH3 domain-binding glutamic acid-
      rich-like protein (SH3BGRL) tryptic digest peptide

<400> SEQUENCE: 11

Asp Ile Ala Ala Asn Glu Glu Asn Arg Lys
1               5                   10

<210> SEQ ID NO 12
<211> LENGTH: 18
<212> TYPE: PRT
<213> ORGANISM: Artificial Sequence
<220> FEATURE:
<223> OTHER INFORMATION: synthetic SH3 domain-binding glutamic acid-
      rich-like protein (SH3BGRL) tryptic digest peptide

<400> SEQUENCE: 12

Glu Asn Asn Ala Val Tyr Ala Phe Leu Gly Leu Thr Ala Pro Pro Gly
1               5                   10                  15

Ser Lys

<210> SEQ ID NO 13
<211> LENGTH: 12
<212> TYPE: PRT
<213> ORGANISM: Artificial Sequence
<220> FEATURE:
<223> OTHER INFORMATION: synthetic SH3 domain-binding glutamic acid-
      rich-like protein (SH3BGRL) tryptic digest peptide

<400> SEQUENCE: 13

Gln Gln Asp Val Leu Gly Phe Leu Glu Ala Asn Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: synthetic SH3 domain-binding glutamic acid-
      rich-like protein (SH3BGRL) tryptic digest peptide

<400> SEQUENCE: 14

Val Tyr Ile Ala Ser Ser Ser Gly Ser Thr Ala Ile Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: synthetic hematopoietic lineage cell specific
      protein (HCLS1) tryptic digest peptide

<400> SEQUENCE: 15

Thr Thr Pro Ile Glu Ala Ala Ser Ser Gly Ala Arg
1               5                   10

<210> SEQ ID NO 16
```

```
<211> LENGTH: 12
<212> TYPE: PRT
<213> ORGANISM: Artificial Sequence
<220> FEATURE:
<223> OTHER INFORMATION: synthetic histone H1.2 (HIST1H1C) tryptic
      digest peptide

<400> SEQUENCE: 16

Ala Ser Gly Pro Pro Val Ser Glu Leu Ile Thr Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: synthetic epsilon globin (HBE1) tryptic digest
      peptide

<400> SEQUENCE: 17

Leu Leu Val Val Tyr Pro Trp Thr Gln Arg
1               5                   10

<210> SEQ ID NO 18
<211> LENGTH: 32
<212> TYPE: PRT
<213> ORGANISM: Artificial Sequence
<220> FEATURE:
<223> OTHER INFORMATION: synthetic S100 calcium-binding protein A12
      (S100A12, calgranulin) tryptic digest peptide

<400> SEQUENCE: 18

Ala Val Ile Asp Glu Ile Phe Gln Gly Leu Asp Ala Asn Gln Asp Glu
1               5                   10                  15

Gln Val Asp Phe Gln Glu Phe Ile Ser Leu Val Ala Ile Ala Leu Lys
            20                  25                  30

<210> SEQ ID NO 19
<211> LENGTH: 7
<212> TYPE: PRT
<213> ORGANISM: Artificial Sequence
<220> FEATURE:
<223> OTHER INFORMATION: synthetic S100 calcium-binding protein A12
      (S100A12, calgranulin) tryptic digest peptide

<400> SEQUENCE: 19

Glu Leu Ala Asn Thr Ile Lys
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic S100 calcium-binding protein A12
      (S100A12, calgranulin) tryptic digest peptide

<400> SEQUENCE: 20

Gly His Phe Asp Thr Leu Ser Lys
1               5

<210> SEQ ID NO 21
<211> LENGTH: 12
<212> TYPE: PRT
<213> ORGANISM: Artificial Sequence
<220> FEATURE:
<223> OTHER INFORMATION: synthetic S100 calcium-binding protein A12
      (S100A12, calgranulin) tryptic digest peptide
```

<400> SEQUENCE: 21

Gly His Phe Asp Thr Leu Ser Lys Gly Glu Leu Lys
1               5                   10

<210> SEQ ID NO 22
<211> LENGTH: 7
<212> TYPE: PRT
<213> ORGANISM: Artificial Sequence
<220> FEATURE:
<223> OTHER INFORMATION: synthetic putative S100 calcium-binding protein
      H_NH0456N16.1 tryptic digest peptide

<400> SEQUENCE: 22

Asp Pro Gly Val Leu Asp Arg
1               5

<210> SEQ ID NO 23
<211> LENGTH: 16
<212> TYPE: PRT
<213> ORGANISM: Artificial Sequence
<220> FEATURE:
<223> OTHER INFORMATION: synthetic putative S100 calcium-binding protein
      H_NH0456N16.1 tryptic digest peptide

<400> SEQUENCE: 23

Thr Glu Phe Leu Ser Phe Met Asn Thr Glu Leu Ala Ala Phe Thr Lys
1               5                   10                  15

<210> SEQ ID NO 24
<211> LENGTH: 8
<212> TYPE: PRT
<213> ORGANISM: Artificial Sequence
<220> FEATURE:
<223> OTHER INFORMATION: synthetic calcyclin tryptic digest peptide

<400> SEQUENCE: 24

Leu Gln Asp Ala Glu Ile Ala Arg
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic cathepsin G tryptic digest peptide

<400> SEQUENCE: 25

Asn Val Asn Pro Val Ala Leu Pro Arg
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic cathepsin G tryptic digest peptide

<400> SEQUENCE: 26

Val Ser Ser Phe Leu Pro Trp Ile Arg
1               5

<210> SEQ ID NO 27
<211> LENGTH: 7
<212> TYPE: PRT
<213> ORGANISM: Artificial Sequence
<220> FEATURE:

<223> OTHER INFORMATION: synthetic vitamin D-binding protein (GC)
      tryptic digest peptide

<400> SEQUENCE: 27

Val Leu Glu Pro Thr Leu Lys
1               5

<210> SEQ ID NO 28
<211> LENGTH: 14
<212> TYPE: PRT
<213> ORGANISM: Artificial Sequence
<220> FEATURE:
<223> OTHER INFORMATION: synthetic brain acid soluble protein 1 (BASP1)
      tryptic digest peptide

<400> SEQUENCE: 28

Glu Thr Pro Ala Ala Thr Glu Ala Pro Ser Ser Thr Pro Lys
1               5                   10

<210> SEQ ID NO 29
<211> LENGTH: 9
<212> TYPE: PRT
<213> ORGANISM: Artificial Sequence
<220> FEATURE:
<223> OTHER INFORMATION: synthetic peroxisome biogenesis factor 1 (PEX1)
      tryptic digest peptide

<400> SEQUENCE: 29

Gly Met Met Lys Glu Leu Gln Thr Lys
1               5

<210> SEQ ID NO 30
<211> LENGTH: 17
<212> TYPE: PRT
<213> ORGANISM: Artificial Sequence
<220> FEATURE:
<223> OTHER INFORMATION: synthetic moesin (MSN) tryptic digest peptide

<400> SEQUENCE: 30

Phe Tyr Pro Glu Asp Val Ser Glu Glu Leu Ile Gln Asp Ile Thr Gln
1               5                   10                  15

Arg

<210> SEQ ID NO 31
<211> LENGTH: 8
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 31

Asp Ala Gln Ile Phe Ile Gln Lys
1               5

<210> SEQ ID NO 32
<211> LENGTH: 13
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 32

Asp Pro Ile Leu Phe Pro Ser Phe Ile His Ser Gln Lys
1               5                   10

<210> SEQ ID NO 33

<211> LENGTH: 15
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 33

Phe Ser Thr Val Ala Gly Glu Ser Gly Ser Ala Asp Thr Val Arg
1               5                   10                  15

<210> SEQ ID NO 34
<211> LENGTH: 18
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 34

Phe Ser Thr Val Ala Gly Glu Ser Gly Ser Ala Asp Thr Val Arg Asp
1               5                   10                  15

Pro Arg

<210> SEQ ID NO 35
<211> LENGTH: 16
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 35

Gly Ala Gly Ala Phe Gly Tyr Phe Glu Val Thr His Asp Ile Thr Lys
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 36

Leu Asn Val Ile Thr Val Gly Pro Arg
1               5

<210> SEQ ID NO 37
<211> LENGTH: 9
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 37

Asn Leu Ser Val Glu Asp Ala Ala Arg
1               5

<210> SEQ ID NO 38
<211> LENGTH: 18
<212> TYPE: PRT
<213> ORGANISM: Artificial Sequence
<220> FEATURE:
<223> OTHER INFORMATION: synthetic peptidylprolyl isomerase A-like
      tryptic digest peptide

<400> SEQUENCE: 38

Val Asn Pro Thr Val Phe Phe Asp Ile Ala Val Asp Gly Glu Pro Leu
1               5                   10                  15

Gly Arg

<210> SEQ ID NO 39
<211> LENGTH: 8
<212> TYPE: PRT
<213> ORGANISM: Artificial Sequence
<220> FEATURE:
<223> OTHER INFORMATION: synthetic myeloperoxidase splice isoforms 1 and
      2 tryptic digest peptide

<400> SEQUENCE: 39

Ala Val Ser Asn Glu Ile Val Arg
1               5

<210> SEQ ID NO 40
<211> LENGTH: 13
<212> TYPE: PRT
<213> ORGANISM: Artificial Sequence
<220> FEATURE:
<223> OTHER INFORMATION: synthetic myeloperoxidase splice isoform 2
      tryptic digest peptide

<400> SEQUENCE: 40

Asp Tyr Leu Pro Leu Val Leu Gly Pro Thr Ala Met Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: synthetic myeloperoxidase splice isoforms 1 and
      2 tryptic digest peptide

<400> SEQUENCE: 41

Ile Gly Leu Asp Leu Pro Ala Leu Asn Met Gln Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: synthetic myeloperoxidase splice isoform 2
      tryptic digest peptide

<400> SEQUENCE: 42

Asn Asn Ile Phe Met Ser Asn Ser Tyr Pro Arg
1               5                   10

<210> SEQ ID NO 43
<211> LENGTH: 24
<212> TYPE: PRT
<213> ORGANISM: Artificial Sequence
<220> FEATURE:
<223> OTHER INFORMATION: synthetic myeloperoxidase splice isoform 2
      tryptic digest peptide

<400> SEQUENCE: 43

Asn Gln Ile Asn Ala Leu Thr Ser Phe Val Asp Ala Ser Met Val Tyr
1               5                   10                  15

Gly Ser Glu Glu Pro Leu Ala Arg
            20

<210> SEQ ID NO 44
<211> LENGTH: 10
<212> TYPE: PRT

```
<213> ORGANISM: Artificial Sequence
<220> FEATURE:
<223> OTHER INFORMATION: synthetic myeloperoxidase splice isoform 2
      tryptic digest peptide

<400> SEQUENCE: 44

Gln Ala Leu Ala Gln Ile Ser Leu Pro Arg
1               5                   10

<210> SEQ ID NO 45
<211> LENGTH: 10
<212> TYPE: PRT
<213> ORGANISM: Artificial Sequence
<220> FEATURE:
<223> OTHER INFORMATION: synthetic myeloperoxidase splice isoforms 1 and
      2 tryptic digest peptide

<400> SEQUENCE: 45

Gln Asn Gln Ile Ala Val Asp Glu Ile Arg
1               5                   10

<210> SEQ ID NO 46
<211> LENGTH: 9
<212> TYPE: PRT
<213> ORGANISM: Artificial Sequence
<220> FEATURE:
<223> OTHER INFORMATION: synthetic myeloperoxidase splice isoforms 1 and
      2 tryptic digest peptide

<400> SEQUENCE: 46

Ser Pro Thr Leu Gly Ala Ser Asn Arg
1               5

<210> SEQ ID NO 47
<211> LENGTH: 13
<212> TYPE: PRT
<213> ORGANISM: Artificial Sequence
<220> FEATURE:
<223> OTHER INFORMATION: synthetic myeloperoxidase splice isoform 2
      tryptic digest peptide

<400> SEQUENCE: 47

Ser Arg Asp His Gly Leu Pro Gly Tyr Asn Ala Trp Arg
1               5                   10

<210> SEQ ID NO 48
<211> LENGTH: 7
<212> TYPE: PRT
<213> ORGANISM: Artificial Sequence
<220> FEATURE:
<223> OTHER INFORMATION: synthetic myeloperoxidase splice isoform 2
      tryptic digest peptide

<400> SEQUENCE: 48

Val Phe Phe Ala Ser Trp Arg
1               5

<210> SEQ ID NO 49
<211> LENGTH: 12
<212> TYPE: PRT
<213> ORGANISM: Artificial Sequence
<220> FEATURE:
<223> OTHER INFORMATION: synthetic myeloperoxidase splice isoforms 1 and
      2 tryptic digest peptide

<400> SEQUENCE: 49

Val Val Leu Glu Gly Gly Ile Asp Pro Ile Leu Arg
1               5                   10
```

<210> SEQ ID NO 50
<211> LENGTH: 10
<212> TYPE: PRT
<213> ORGANISM: Artificial Sequence
<220> FEATURE:
<223> OTHER INFORMATION: synthetic myeloperoxidase splice isoform 1
      tryptic digest peptide

<400> SEQUENCE: 50

Ile Ala Asn Val Phe Thr Asn Ala Phe Arg
1               5                   10

<210> SEQ ID NO 51
<211> LENGTH: 14
<212> TYPE: PRT
<213> ORGANISM: Artificial Sequence
<220> FEATURE:
<223> OTHER INFORMATION: synthetic myeloperoxidase splice isoform 1
      tryptic digest peptide

<400> SEQUENCE: 51

Val Gly Pro Leu Leu Ala Cys Ile Ile Gly Thr Gln Phe Arg
1               5                   10

<210> SEQ ID NO 52
<211> LENGTH: 12
<212> TYPE: PRT
<213> ORGANISM: Artificial Sequence
<220> FEATURE:
<223> OTHER INFORMATION: synthetic haptoglobin-related protein tryptic
      digest peptide

<400> SEQUENCE: 52

Asp Ile Ala Pro Thr Leu Thr Leu Tyr Val Gly Lys
1               5                   10

<210> SEQ ID NO 53
<211> LENGTH: 7
<212> TYPE: PRT
<213> ORGANISM: Artificial Sequence
<220> FEATURE:
<223> OTHER INFORMATION: synthetic tumor-related protein tryptic digest
      peptide

<400> SEQUENCE: 53

Glu Leu Tyr Ser Tyr Leu Arg
1               5

<210> SEQ ID NO 54
<211> LENGTH: 24
<212> TYPE: PRT
<213> ORGANISM: Artificial Sequence
<220> FEATURE:
<223> OTHER INFORMATION: synthetic tumor-related protein tryptic digest
      peptide

<400> SEQUENCE: 54

Leu Asp Gln Gly Asn Leu His Thr Ser Val Ser Ser Ala Gln Gly Gln
1               5                   10                  15

Asp Ala Ala Gln Ser Glu Glu Lys
            20

<210> SEQ ID NO 55
<211> LENGTH: 25
<212> TYPE: PRT
<213> ORGANISM: Artificial Sequence -continued

```
<220> FEATURE:
<223> OTHER INFORMATION: synthetic tumor-related protein tryptic digest
      peptide

<400> SEQUENCE: 55

Leu Asp Gln Gly Asn Leu His Thr Ser Val Ser Ser Ala Gln Gly Gln
1               5                   10                  15

Asp Ala Ala Gln Ser Glu Glu Lys Arg
            20                  25

<210> SEQ ID NO 56
<211> LENGTH: 15
<212> TYPE: PRT
<213> ORGANISM: Artificial Sequence
<220> FEATURE:
<223> OTHER INFORMATION: synthetic tumor-related protein tryptic digest
      peptide

<400> SEQUENCE: 56

Gln Pro Thr Val Val Gly Glu Glu Trp Val Asp Asp His Ser Arg
1               5                   10                  15

<210> SEQ ID NO 57
<211> LENGTH: 27
<212> TYPE: PRT
<213> ORGANISM: Artificial Sequence
<220> FEATURE:
<223> OTHER INFORMATION: synthetic tumor-related protein tryptic digest
      peptide

<400> SEQUENCE: 57

Ser Gln Thr Ser Gln Ala Val Thr Gly Gly His Thr Gln Ile Gln Ala
1               5                   10                  15

Gly Ser His Thr Glu Thr Val Glu Gln Asp Arg
            20                  25

<210> SEQ ID NO 58
<211> LENGTH: 9
<212> TYPE: PRT
<213> ORGANISM: Artificial Sequence
<220> FEATURE:
<223> OTHER INFORMATION: synthetic beta-2-glycoprotein 1 tryptic digest
      peptide

<400> SEQUENCE: 58

Ala Thr Val Val Tyr Gln Gly Glu Arg
1               5

<210> SEQ ID NO 59
<211> LENGTH: 11
<212> TYPE: PRT
<213> ORGANISM: Artificial Sequence
<220> FEATURE:
<223> OTHER INFORMATION: synthetic peroxiredoxin 2 tryptic digest
      peptide

<400> SEQUENCE: 59

Gln Ile Thr Val Asn Asp Leu Pro Val Gly Arg
1               5                   10

<210> SEQ ID NO 60
<211> LENGTH: 8
<212> TYPE: PRT
<213> ORGANISM: Artificial Sequence
<220> FEATURE:
<223> OTHER INFORMATION: synthetic peroxiredoxin 2 tryptic digest
      peptide
```

```
<400> SEQUENCE: 60

Thr Asp Glu Gly Ile Ala Tyr Arg
1               5

<210> SEQ ID NO 61
<211> LENGTH: 11
<212> TYPE: PRT
<213> ORGANISM: Artificial Sequence
<220> FEATURE:
<223> OTHER INFORMATION: synthetic thioredoxin tryptic digest peptide

<400> SEQUENCE: 61

Glu Lys Leu Glu Ala Thr Ile Asn Glu Leu Val
1               5                   10

<210> SEQ ID NO 62
<211> LENGTH: 12
<212> TYPE: PRT
<213> ORGANISM: Artificial Sequence
<220> FEATURE:
<223> OTHER INFORMATION: synthetic thioredoxin tryptic digest peptide

<400> SEQUENCE: 62

Met Ile Lys Pro Phe Phe His Ser Leu Ser Glu Lys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: synthetic thioredoxin tryptic digest peptide

<400> SEQUENCE: 63

Thr Ala Phe Gln Glu Ala Leu Asp Ala Ala Gly Asp Lys
1               5                   10

<210> SEQ ID NO 64
<211> LENGTH: 9
<212> TYPE: PRT
<213> ORGANISM: Artificial Sequence
<220> FEATURE:
<223> OTHER INFORMATION: synthetic thioredoxin tryptic digest peptide

<400> SEQUENCE: 64

Val Gly Glu Phe Ser Gly Ala Asn Lys
1               5

<210> SEQ ID NO 65
<211> LENGTH: 12
<212> TYPE: PRT
<213> ORGANISM: Artificial Sequence
<220> FEATURE:
<223> OTHER INFORMATION: synthetic heat shock 70 kDa protein 1 tryptic
      digest peptide

<400> SEQUENCE: 65

Asp Ala Gly Val Ile Ala Gly Leu Asn Val Leu Arg
1               5                   10

<210> SEQ ID NO 66
<211> LENGTH: 9
<212> TYPE: PRT
<213> ORGANISM: Artificial Sequence
<220> FEATURE:
<223> OTHER INFORMATION: synthetic heat shock 70 kDa protein 1 tryptic
``` digest peptide

<400> SEQUENCE: 66

Leu Leu Gln Asp Phe Phe Asn Gly Arg
1               5

<210> SEQ ID NO 67
<211> LENGTH: 11
<212> TYPE: PRT
<213> ORGANISM: Artificial Sequence
<220> FEATURE:
<223> OTHER INFORMATION: synthetic heat shock 70 kDa protein 1 tryptic
      digest peptide

<400> SEQUENCE: 67

Leu Val Asn His Phe Val Glu Glu Phe Lys Arg
1               5                   10

<210> SEQ ID NO 68
<211> LENGTH: 11
<212> TYPE: PRT
<213> ORGANISM: Artificial Sequence
<220> FEATURE:
<223> OTHER INFORMATION: synthetic heat shock 70 kDa protein 1 tryptic
      digest peptide

<400> SEQUENCE: 68

Asn Ala Leu Glu Ser Tyr Ala Phe Asn Met Lys
1               5                   10

<210> SEQ ID NO 69
<211> LENGTH: 8
<212> TYPE: PRT
<213> ORGANISM: Artificial Sequence
<220> FEATURE:
<223> OTHER INFORMATION: synthetic heat shock 70 kDa protein 1 tryptic
      digest peptide

<400> SEQUENCE: 69

Ser Thr Leu Glu Pro Val Glu Lys
1               5

<210> SEQ ID NO 70
<211> LENGTH: 18
<212> TYPE: PRT
<213> ORGANISM: Artificial Sequence
<220> FEATURE:
<223> OTHER INFORMATION: synthetic enolase 1 tryptic digest peptide

<400> SEQUENCE: 70

Ala Ala Val Pro Ser Gly Ala Ser Thr Gly Ile Tyr Glu Ala Leu Glu
1               5                   10                  15

Leu Arg

<210> SEQ ID NO 71
<211> LENGTH: 7
<212> TYPE: PRT
<213> ORGANISM: Artificial Sequence
<220> FEATURE:
<223> OTHER INFORMATION: synthetic enolase 1 tryptic digest peptide

<400> SEQUENCE: 71

Glu Gly Leu Glu Leu Leu Lys
1               5

<210> SEQ ID NO 72

```
<211> LENGTH: 6
<212> TYPE: PRT
<213> ORGANISM: Artificial Sequence
<220> FEATURE:
<223> OTHER INFORMATION: synthetic enolase 1 tryptic digest peptide

<400> SEQUENCE: 72

Glu Ile Phe Asp Ser Arg
1               5

<210> SEQ ID NO 73
<211> LENGTH: 13
<212> TYPE: PRT
<213> ORGANISM: Artificial Sequence
<220> FEATURE:
<223> OTHER INFORMATION: synthetic enolase 1 tryptic digest peptide

<400> SEQUENCE: 73

Gly Asn Pro Thr Val Glu Val Asp Leu Phe Thr Ser Lys
1               5                   10

<210> SEQ ID NO 74
<211> LENGTH: 8
<212> TYPE: PRT
<213> ORGANISM: Artificial Sequence
<220> FEATURE:
<223> OTHER INFORMATION: synthetic enolase 1 tryptic digest peptide

<400> SEQUENCE: 74

Ile Glu Glu Glu Leu Gly Ser Lys
1               5

<210> SEQ ID NO 75
<211> LENGTH: 17
<212> TYPE: PRT
<213> ORGANISM: Artificial Sequence
<220> FEATURE:
<223> OTHER INFORMATION: synthetic enolase 1 tryptic digest peptide

<400> SEQUENCE: 75

Leu Ala Met Gln Glu Phe Met Ile Leu Pro Val Gly Ala Ala Asn Phe
1               5                   10                  15

Arg

<210> SEQ ID NO 76
<211> LENGTH: 14
<212> TYPE: PRT
<213> ORGANISM: Artificial Sequence
<220> FEATURE:
<223> OTHER INFORMATION: synthetic enolase 1 tryptic digest peptide

<400> SEQUENCE: 76

Leu Ala Gln Ala Asn Gly Trp Gly Val Met Val Ser His Arg
1               5                   10

<210> SEQ ID NO 77
<211> LENGTH: 8
<212> TYPE: PRT
<213> ORGANISM: Artificial Sequence
<220> FEATURE:
<223> OTHER INFORMATION: synthetic enolase 1 tryptic digest peptide

<400> SEQUENCE: 77

Leu Asn Val Thr Glu Gln Glu Lys
1               5
```

```
<210> SEQ ID NO 78
<211> LENGTH: 9
<212> TYPE: PRT
<213> ORGANISM: Artificial Sequence
<220> FEATURE:
<223> OTHER INFORMATION: synthetic enolase 1 tryptic digest peptide

<400> SEQUENCE: 78

Thr Ile Ala Pro Ala Leu Val Ser Lys
1               5

<210> SEQ ID NO 79
<211> LENGTH: 12
<212> TYPE: PRT
<213> ORGANISM: Artificial Sequence
<220> FEATURE:
<223> OTHER INFORMATION: synthetic enolase 1 tryptic digest peptide

<400> SEQUENCE: 79

Tyr Ile Ser Pro Asp Gln Leu Ala Asp Leu Tyr Lys
1               5                   10

<210> SEQ ID NO 80
<211> LENGTH: 6
<212> TYPE: PRT
<213> ORGANISM: Artificial Sequence
<220> FEATURE:
<223> OTHER INFORMATION: synthetic enolase 1 tryptic digest peptide

<400> SEQUENCE: 80

Tyr Asn Gln Leu Leu Arg
1               5

<210> SEQ ID NO 81
<211> LENGTH: 13
<212> TYPE: PRT
<213> ORGANISM: Artificial Sequence
<220> FEATURE:
<223> OTHER INFORMATION: synthetic enolase 2 tryptic digest peptide

<400> SEQUENCE: 81

Gly Asn Pro Thr Val Glu Val Asp Leu Tyr Thr Ala Lys
1               5                   10

<210> SEQ ID NO 82
<211> LENGTH: 13
<212> TYPE: PRT
<213> ORGANISM: Artificial Sequence
<220> FEATURE:
<223> OTHER INFORMATION: synthetic enolase 3 tryptic digest peptide

<400> SEQUENCE: 82

Gly Asn Pro Thr Val Glu Val Asp Leu His Thr Ala Lys
1               5                   10

<210> SEQ ID NO 83
<211> LENGTH: 15
<212> TYPE: PRT
<213> ORGANISM: Artificial Sequence
<220> FEATURE:
<223> OTHER INFORMATION: synthetic enolase 3 tryptic digest peptide

<400> SEQUENCE: 83

Val Asn Gln Ile Gly Ser Val Thr Glu Ser Ile Gln Ala Cys Lys
1               5                   10                  15

<210> SEQ ID NO 84
```

```
<211> LENGTH: 15
<212> TYPE: PRT
<213> ORGANISM: Artificial Sequence
<220> FEATURE:
<223> OTHER INFORMATION: synthetic alpha enolase, lung specific tryptic
      digest peptide

<400> SEQUENCE: 84

Val Asn Gln Ile Gly Ser Val Thr Glu Ser Leu Gln Ala Cys Lys
1               5                   10                  15

<210> SEQ ID NO 85
<211> LENGTH: 12
<212> TYPE: PRT
<213> ORGANISM: Artificial Sequence
<220> FEATURE:
<223> OTHER INFORMATION: synthetic alpha enolase, lung specific tryptic
      digest peptide

<400> SEQUENCE: 85

Tyr Ile Ser Pro Asp Gln Leu Ala Asp Leu Tyr Lys
1               5                   10

<210> SEQ ID NO 86
<211> LENGTH: 8
<212> TYPE: PRT
<213> ORGANISM: Artificial Sequence
<220> FEATURE:
<223> OTHER INFORMATION: synthetic antibacterial protein FALL-39 tryptic
      digest peptide

<400> SEQUENCE: 86

Ala Ile Asp Gly Ile Asn Gln Arg
1               5

<210> SEQ ID NO 87
<211> LENGTH: 8
<212> TYPE: PRT
<213> ORGANISM: Artificial Sequence
<220> FEATURE:
<223> OTHER INFORMATION: synthetic antibacterial protein FALL-39 tryptic
      digest peptide

<400> SEQUENCE: 87

Ser Ser Asp Ala Asn Leu Tyr Arg
1               5

<210> SEQ ID NO 88
<211> LENGTH: 12
<212> TYPE: PRT
<213> ORGANISM: Artificial Sequence
<220> FEATURE:
<223> OTHER INFORMATION: synthetic triosephosphate isomerase tryptic
      digest peptide

<400> SEQUENCE: 88

Ser Asn Val Ser Asp Ala Val Ala Gln Ser Thr Arg
1               5                   10

<210> SEQ ID NO 89
<211> LENGTH: 13
<212> TYPE: PRT
<213> ORGANISM: Artificial Sequence
<220> FEATURE:
<223> OTHER INFORMATION: synthetic triosephosphate isomerase tryptic
      digest peptide

<400> SEQUENCE: 89
```

```
Thr Ala Thr Pro Gln Gln Ala Gln Glu Val His Glu Lys
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: synthetic S-100P protein tryptic digest peptide

<400> SEQUENCE: 90

```
Glu Leu Pro Gly Phe Leu Gln Ser Gly Lys
1               5                   10
```

<210> SEQ ID NO 91
<211> LENGTH: 13
<212> TYPE: PRT
<213> ORGANISM: Artificial Sequence
<220> FEATURE:
<223> OTHER INFORMATION: synthetic S-100P protein tryptic digest peptide

<400> SEQUENCE: 91

```
Tyr Ser Gly Ser Glu Gly Ser Thr Gln Thr Leu Thr Lys
1               5                   10
```

<210> SEQ ID NO 92
<211> LENGTH: 8
<212> TYPE: PRT
<213> ORGANISM: Artificial Sequence
<220> FEATURE:
<223> OTHER INFORMATION: synthetic myeloblastin tryptic digest peptide

<400> SEQUENCE: 92

```
Leu Phe Pro Asp Phe Phe Thr Arg
1               5
```

<210> SEQ ID NO 93
<211> LENGTH: 12
<212> TYPE: PRT
<213> ORGANISM: Artificial Sequence
<220> FEATURE:
<223> OTHER INFORMATION: synthetic myeloblastin tryptic digest peptide

<400> SEQUENCE: 93

```
Leu Val Asn Val Val Leu Gly Ala His Asn Val Arg
1               5                   10
```

<210> SEQ ID NO 94
<211> LENGTH: 11
<212> TYPE: PRT
<213> ORGANISM: Artificial Sequence
<220> FEATURE:
<223> OTHER INFORMATION: synthetic calgizzarin tryptic digest peptide

<400> SEQUENCE: 94

```
Cys Ile Glu Ser Leu Ile Ala Val Phe Gln Lys
1               5                   10
```

<210> SEQ ID NO 95
<211> LENGTH: 9
<212> TYPE: PRT
<213> ORGANISM: Artificial Sequence
<220> FEATURE:
<223> OTHER INFORMATION: synthetic calgizzarin tryptic digest peptide

<400> SEQUENCE: 95

```
Asp Gly Tyr Asn Tyr Thr Leu Ser Lys
```

<210> SEQ ID NO 96
<211> LENGTH: 9
<212> TYPE: PRT
<213> ORGANISM: Artificial Sequence
<220> FEATURE:
<223> OTHER INFORMATION: synthetic calgizzarin tryptic digest peptide

<400> SEQUENCE: 96

Ile Ser Ser Pro Thr Glu Thr Glu Arg
1               5

<210> SEQ ID NO 97
<211> LENGTH: 16
<212> TYPE: PRT
<213> ORGANISM: Artificial Sequence
<220> FEATURE:
<223> OTHER INFORMATION: synthetic calgizzarin tryptic digest peptide

<400> SEQUENCE: 97

Thr Glu Phe Leu Ser Phe Met Asn Thr Glu Leu Ala Ala Phe Thr Lys
1               5                   10                  15

<210> SEQ ID NO 98
<211> LENGTH: 12
<212> TYPE: PRT
<213> ORGANISM: Artificial Sequence
<220> FEATURE:
<223> OTHER INFORMATION: synthetic carbonic anhydrase 1 tryptic digest
      peptide

<400> SEQUENCE: 98

Ala Asp Gly Leu Ala Val Ile Gly Val Leu Met Lys
1               5                   10

<210> SEQ ID NO 99
<211> LENGTH: 9
<212> TYPE: PRT
<213> ORGANISM: Artificial Sequence
<220> FEATURE:
<223> OTHER INFORMATION: synthetic carbonic anhydrase 1 tryptic digest
      peptide

<400> SEQUENCE: 99

Val Leu Asp Ala Leu Gln Ala Ile Lys
1               5

<210> SEQ ID NO 100
<211> LENGTH: 10
<212> TYPE: PRT
<213> ORGANISM: Artificial Sequence
<220> FEATURE:
<223> OTHER INFORMATION: synthetic carbonic anhydrase 1 tryptic digest
      peptide

<400> SEQUENCE: 100

Tyr Ser Ser Leu Ala Glu Ala Ala Ser Lys
1               5                   10

<210> SEQ ID NO 101
<211> LENGTH: 11
<212> TYPE: PRT
<213> ORGANISM: Artificial Sequence
<220> FEATURE:
<223> OTHER INFORMATION: synthetic transaldolase tryptic digest peptide

<400> SEQUENCE: 101

```
Leu Phe Val Leu Phe Gly Ala Glu Ile Leu Lys
1               5                   10

<210> SEQ ID NO 102
<211> LENGTH: 11
<212> TYPE: PRT
<213> ORGANISM: Artificial Sequence
<220> FEATURE:
<223> OTHER INFORMATION: synthetic transaldolase tryptic digest peptide

<400> SEQUENCE: 102

Leu Leu Gly Glu Leu Leu Gln Asp Asn Ala Lys
1               5                   10

<210> SEQ ID NO 103
<211> LENGTH: 9
<212> TYPE: PRT
<213> ORGANISM: Artificial Sequence
<220> FEATURE:
<223> OTHER INFORMATION: synthetic transaldolase tryptic digest peptide

<400> SEQUENCE: 103

Thr Ile Val Met Gly Ala Ser Phe Arg
1               5

<210> SEQ ID NO 104
<211> LENGTH: 14
<212> TYPE: PRT
<213> ORGANISM: Artificial Sequence
<220> FEATURE:
<223> OTHER INFORMATION: synthetic alpha-1-acid glycoprotein 1 tryptic
      digest peptide

<400> SEQUENCE: 104

Glu Gln Leu Gly Glu Phe Tyr Glu Ala Leu Asp Cys Leu Arg
1               5                   10

<210> SEQ ID NO 105
<211> LENGTH: 8
<212> TYPE: PRT
<213> ORGANISM: Artificial Sequence
<220> FEATURE:
<223> OTHER INFORMATION: synthetic alpha-1-acid glycoprotein 1 tryptic
      digest peptide

<400> SEQUENCE: 105

Thr Glu Asp Thr Ile Phe Leu Arg
1               5

<210> SEQ ID NO 106
<211> LENGTH: 15
<212> TYPE: PRT
<213> ORGANISM: Artificial Sequence
<220> FEATURE:
<223> OTHER INFORMATION: synthetic alpha-1-acid glycoprotein 1 tryptic
      digest peptide

<400> SEQUENCE: 106

Tyr Val Gly Gly Gln Glu His Phe Ala His Leu Leu Ile Leu Arg
1               5                   10                  15

<210> SEQ ID NO 107
<211> LENGTH: 9
<212> TYPE: PRT
<213> ORGANISM: Artificial Sequence
<220> FEATURE:
<223> OTHER INFORMATION: synthetic azurocidin tryptic digest peptide
```

```
<400> SEQUENCE: 107

Cys Gln Val Ala Gly Trp Gly Ser Gln
1               5

<210> SEQ ID NO 108
<211> LENGTH: 11
<212> TYPE: PRT
<213> ORGANISM: Artificial Sequence
<220> FEATURE:
<223> OTHER INFORMATION: synthetic azurocidin tryptic digest peptide

<400> SEQUENCE: 108

His Phe Cys Gly Gly Ala Leu Ile His Ala Arg
1               5                   10

<210> SEQ ID NO 109
<211> LENGTH: 13
<212> TYPE: PRT
<213> ORGANISM: Artificial Sequence
<220> FEATURE:
<223> OTHER INFORMATION: synthetic azurocidin tryptic digest peptide

<400> SEQUENCE: 109

Gln Phe Pro Phe Leu Ala Ser Ile Gln Asn Gln Gly Arg
1               5                   10

<210> SEQ ID NO 110
<211> LENGTH: 9
<212> TYPE: PRT
<213> ORGANISM: Artificial Sequence
<220> FEATURE:
<223> OTHER INFORMATION: synthetic similar to SEC14-like protein 2
      tryptic digest peptide

<400> SEQUENCE: 110

Ile Val Ile Leu Gly Asp Asn Trp Lys
1               5

<210> SEQ ID NO 111
<211> LENGTH: 9
<212> TYPE: PRT
<213> ORGANISM: Artificial Sequence
<220> FEATURE:
<223> OTHER INFORMATION: synthetic transcription intermediary factor
      1-gamma splice isoform 1 tryptic digest peptide

<400> SEQUENCE: 111

Gly Ala Ile Glu Asn Leu Leu Ala Lys
1               5

<210> SEQ ID NO 112
<211> LENGTH: 11
<212> TYPE: PRT
<213> ORGANISM: Artificial Sequence
<220> FEATURE:
<223> OTHER INFORMATION: synthetic hemopexin tryptic digest peptide

<400> SEQUENCE: 112

Gly Gly Tyr Thr Leu Val Ser Gly Tyr Pro Lys
1               5                   10

<210> SEQ ID NO 113
<211> LENGTH: 11
<212> TYPE: PRT
<213> ORGANISM: Artificial Sequence
<220> FEATURE:
```

<223> OTHER INFORMATION: synthetic hemopexin tryptic digest peptide

<400> SEQUENCE: 113

Asn Phe Pro Ser Pro Val Asp Ala Ala Phe Arg
1               5                   10

<210> SEQ ID NO 114
<211> LENGTH: 7
<212> TYPE: PRT
<213> ORGANISM: Artificial Sequence
<220> FEATURE:
<223> OTHER INFORMATION: synthetic muscarinic acetylcholine receptor M3
      tryptic digest peptide

<400> SEQUENCE: 114

Met Ser Leu Val Lys Glu Lys
1               5

<210> SEQ ID NO 115
<211> LENGTH: 10
<212> TYPE: PRT
<213> ORGANISM: Artificial Sequence
<220> FEATURE:
<223> OTHER INFORMATION: synthetic cytoplasmic antiproteinase 2 tryptic
      digest peptide

<400> SEQUENCE: 115

Leu Val Leu Val Asn Ala Ile Tyr Phe Lys
1               5                   10

<210> SEQ ID NO 116
<211> LENGTH: 9
<212> TYPE: PRT
<213> ORGANISM: Artificial Sequence
<220> FEATURE:
<223> OTHER INFORMATION: synthetic similar to myomegalin tryptic digest
      peptide

<400> SEQUENCE: 116

Gly Gln Leu Gly Leu Gly Gly Ser Arg
1               5

<210> SEQ ID NO 117
<211> LENGTH: 9
<212> TYPE: PRT
<213> ORGANISM: Artificial Sequence
<220> FEATURE:
<223> OTHER INFORMATION: synthetic shroom-related protein tryptic digest
      peptide

<400> SEQUENCE: 117

Ser Ser Pro Ala Thr Ala Asp Lys Arg
1               5

<210> SEQ ID NO 118
<211> LENGTH: 15
<212> TYPE: PRT
<213> ORGANISM: Artificial Sequence
<220> FEATURE:
<223> OTHER INFORMATION: synthetic phosphoglycerate kinase 1 tryptic
      digest peptide

<400> SEQUENCE: 118

Leu Gly Asp Val Tyr Val Asn Asp Ala Phe Gly Thr Ala His Arg
1               5                   10                  15

<210> SEQ ID NO 119

```
<211> LENGTH: 19
<212> TYPE: PRT
<213> ORGANISM: Artificial Sequence
<220> FEATURE:
<223> OTHER INFORMATION: synthetic 11 kDa protein tryptic digest peptide

<400> SEQUENCE: 119

Glu Val Gln Leu Val Glu Ser Gly Gly Gly Leu Val Gln Pro Gly Gly
1               5                   10                  15

Ser Leu Arg

<210> SEQ ID NO 120
<211> LENGTH: 11
<212> TYPE: PRT
<213> ORGANISM: Artificial Sequence
<220> FEATURE:
<223> OTHER INFORMATION: synthetic 11 kDa protein tryptic digest peptide

<400> SEQUENCE: 120

Asn Ser Leu Tyr Leu Gln Met Asn Ser Leu Arg
1               5                   10

<210> SEQ ID NO 121
<211> LENGTH: 9
<212> TYPE: PRT
<213> ORGANISM: Artificial Sequence
<220> FEATURE:
<223> OTHER INFORMATION: synthetic 16 kDa protein (HBA1) tryptic digest
      peptide

<400> SEQUENCE: 121

Met Phe Leu Ser Phe Pro Thr Thr Lys
1               5

<210> SEQ ID NO 122
<211> LENGTH: 16
<212> TYPE: PRT
<213> ORGANISM: Artificial Sequence
<220> FEATURE:
<223> OTHER INFORMATION: synthetic 16 kDa protein (HBA1) tryptic digest
      peptide

<400> SEQUENCE: 122

Thr Tyr Phe Pro His Phe Asp Leu Ser His Gly Ser Ala Gln Val Lys
1               5                   10                  15

<210> SEQ ID NO 123
<211> LENGTH: 12
<212> TYPE: PRT
<213> ORGANISM: Artificial Sequence
<220> FEATURE:
<223> OTHER INFORMATION: synthetic 57 kDa protein (keratin 10) tryptic
      digest peptide

<400> SEQUENCE: 123

Gln Ser Val Glu Ala Asp Ile Asn Gly Leu Arg Arg
1               5                   10

<210> SEQ ID NO 124
<211> LENGTH: 9
<212> TYPE: PRT
<213> ORGANISM: Artificial Sequence
<220> FEATURE:
<223> OTHER INFORMATION: synthetic 57 kDa protein (keratin 10) tryptic
      digest peptide

<400> SEQUENCE: 124
```

```
Val Leu Asp Glu Leu Thr Leu Thr Lys
1               5

<210> SEQ ID NO 125
<211> LENGTH: 14
<212> TYPE: PRT
<213> ORGANISM: Artificial Sequence
<220> FEATURE:
<223> OTHER INFORMATION: synthetic 143 kDa protein, 78 kDa protein, 83
      kDa protein and 169 kDa protein tryptic digest peptide

<400> SEQUENCE: 125

Phe Gly Gln Gly Ser Gly Pro Ile Val Leu Asp Asp Val Arg
1               5                   10

<210> SEQ ID NO 126
<211> LENGTH: 6
<212> TYPE: PRT
<213> ORGANISM: Artificial Sequence
<220> FEATURE:
<223> OTHER INFORMATION: synthetic 143 kDa protein, 83 kDa protein and
      169 kDa protein tryptic digest peptide

<400> SEQUENCE: 126

Val Glu Ile Leu Tyr Arg
1               5

<210> SEQ ID NO 127
<211> LENGTH: 12
<212> TYPE: PRT
<213> ORGANISM: Artificial Sequence
<220> FEATURE:
<223> OTHER INFORMATION: synthetic clusterin tryptic digest peptide

<400> SEQUENCE: 127

Ala Ser Ser Ile Ile Asp Glu Leu Phe Gln Asp Arg
1               5                   10

<210> SEQ ID NO 128
<211> LENGTH: 11
<212> TYPE: PRT
<213> ORGANISM: Artificial Sequence
<220> FEATURE:
<223> OTHER INFORMATION: synthetic clusterin tryptic digest peptide

<400> SEQUENCE: 128

Glu Leu Asp Glu Ser Leu Gln Val Ala Glu Arg
1               5                   10

<210> SEQ ID NO 129
<211> LENGTH: 8
<212> TYPE: PRT
<213> ORGANISM: Artificial Sequence
<220> FEATURE:
<223> OTHER INFORMATION: synthetic clusterin tryptic digest peptide

<400> SEQUENCE: 129

Phe Met Glu Thr Val Ala Glu Lys
1               5

<210> SEQ ID NO 130
<211> LENGTH: 9
<212> TYPE: PRT
<213> ORGANISM: Artificial Sequence
<220> FEATURE:
<223> OTHER INFORMATION: synthetic clusterin tryptic digest peptide

<400> SEQUENCE: 130
```

```
Ile Asp Ser Leu Leu Glu Asn Asp Arg
1               5
```

<210> SEQ ID NO 131
<211> LENGTH: 11
<212> TYPE: PRT
<213> ORGANISM: Artificial Sequence
<220> FEATURE:
<223> OTHER INFORMATION: synthetic uteroglobin tryptic digest peptide

<400> SEQUENCE: 131

```
Lys Leu Val Asp Thr Leu Pro Gln Lys Pro Arg
1               5                   10
```

<210> SEQ ID NO 132
<211> LENGTH: 10
<212> TYPE: PRT
<213> ORGANISM: Artificial Sequence
<220> FEATURE:
<223> OTHER INFORMATION: synthetic uteroglobin tryptic digest peptide

<400> SEQUENCE: 132

```
Leu Val Asp Thr Leu Pro Gln Lys Pro Arg
1               5                   10
```

<210> SEQ ID NO 133
<211> LENGTH: 10
<212> TYPE: PRT
<213> ORGANISM: Artificial Sequence
<220> FEATURE:
<223> OTHER INFORMATION: synthetic utrophin tryptic digest peptide

<400> SEQUENCE: 133

```
Gln Glu Leu Pro Pro Pro Pro Pro Pro Lys
1               5                   10
```

<210> SEQ ID NO 134
<211> LENGTH: 12
<212> TYPE: PRT
<213> ORGANISM: Artificial Sequence
<220> FEATURE:
<223> OTHER INFORMATION: synthetic utrophin tryptic digest peptide

<400> SEQUENCE: 134

```
Ser Lys Gln Glu Leu Pro Pro Pro Pro Pro Pro Lys
1               5                   10
```

<210> SEQ ID NO 135
<211> LENGTH: 8
<212> TYPE: PRT
<213> ORGANISM: Artificial Sequence
<220> FEATURE:
<223> OTHER INFORMATION: synthetic cornifin A tryptic digest peptide

<400> SEQUENCE: 135

```
Ile Pro Glu Pro Cys Gln Pro Lys
1               5
```

<210> SEQ ID NO 136
<211> LENGTH: 14
<212> TYPE: PRT
<213> ORGANISM: Artificial Sequence
<220> FEATURE:
<223> OTHER INFORMATION: synthetic cornifin A and B tryptic digest
      peptide

<400> SEQUENCE: 136

```
Gln Pro Cys Gln Pro Pro Pro Gln Glu Pro Cys Ile Pro Lys
1               5                   10
```

```
<210> SEQ ID NO 137
<211> LENGTH: 17
<212> TYPE: PRT
<213> ORGANISM: Artificial Sequence
<220> FEATURE:
<223> OTHER INFORMATION: synthetic cornifin A tryptic digest peptide

<400> SEQUENCE: 137

Val Pro Glu Pro Cys Pro Ser Thr Val Thr Pro Ala Pro Ala Gln Gln
1               5                   10                  15

Lys
```

```
<210> SEQ ID NO 138
<211> LENGTH: 17
<212> TYPE: PRT
<213> ORGANISM: Artificial Sequence
<220> FEATURE:
<223> OTHER INFORMATION: synthetic cornifin B tryptic digest peptide

<400> SEQUENCE: 138

Val Pro Glu Pro Cys Pro Ser Ile Val Thr Pro Ala Pro Ala Gln Gln
1               5                   10                  15

Lys
```

```
<210> SEQ ID NO 139
<211> LENGTH: 13
<212> TYPE: PRT
<213> ORGANISM: Artificial Sequence
<220> FEATURE:
<223> OTHER INFORMATION: synthetic SPARC-like protein 1 tryptic digest
      peptide

<400> SEQUENCE: 139

Leu Leu Ala Gly Asp His Pro Ile Asp Leu Leu Leu Arg
1               5                   10
```

```
<210> SEQ ID NO 140
<211> LENGTH: 15
<212> TYPE: PRT
<213> ORGANISM: Artificial Sequence
<220> FEATURE:
<223> OTHER INFORMATION: synthetic SPARC-like protein 1 tryptic digest
      peptide

<400> SEQUENCE: 140

Thr Gly Leu Glu Ala Ile Ser Asn His Lys Glu Thr Glu Glu Lys
1               5                   10                  15
```

```
<210> SEQ ID NO 141
<211> LENGTH: 12
<212> TYPE: PRT
<213> ORGANISM: Artificial Sequence
<220> FEATURE:
<223> OTHER INFORMATION: synthetic metalloproteinase inhibitor 1 tryptic
      digest peptide

<400> SEQUENCE: 141

Gly Phe Gln Ala Leu Gly Asp Ala Ala Asp Ile Arg
1               5                   10
```

```
<210> SEQ ID NO 142
<211> LENGTH: 7
```

```
<212> TYPE: PRT
<213> ORGANISM: Artificial Sequence
<220> FEATURE:
<223> OTHER INFORMATION: synthetic metalloproteinase inhibitor 1 tryptic
      digest peptide

<400> SEQUENCE: 142

His Leu Ala Cys Leu Pro Arg
1               5

<210> SEQ ID NO 143
<211> LENGTH: 9
<212> TYPE: PRT
<213> ORGANISM: Artificial Sequence
<220> FEATURE:
<223> OTHER INFORMATION: synthetic macrophage migration inhibitory
      factor tryptic digest peptide

<400> SEQUENCE: 143

Leu Leu Cys Gly Leu Leu Ala Glu Arg
1               5

<210> SEQ ID NO 144
<211> LENGTH: 12
<212> TYPE: PRT
<213> ORGANISM: Artificial Sequence
<220> FEATURE:
<223> OTHER INFORMATION: synthetic antileukoproteinase 1 tryptic digest
      peptide

<400> SEQUENCE: 144

Cys Leu Asp Pro Val Asp Thr Pro Asn Pro Thr Arg
1               5                   10

<210> SEQ ID NO 145
<211> LENGTH: 8
<212> TYPE: PRT
<213> ORGANISM: Artificial Sequence
<220> FEATURE:
<223> OTHER INFORMATION: synthetic antileukoproteinase 1 tryptic digest
      peptide

<400> SEQUENCE: 145

Ser Cys Val Ser Pro Val Lys Ala
1               5

<210> SEQ ID NO 146
<211> LENGTH: 15
<212> TYPE: PRT
<213> ORGANISM: Artificial Sequence
<220> FEATURE:
<223> OTHER INFORMATION: synthetic desmoglein 3 tryptic digest peptide

<400> SEQUENCE: 146

Thr Ile Thr Ala Glu Val Leu Ala Ile Asp Glu Tyr Thr Gly Lys
1               5                   10                  15

<210> SEQ ID NO 147
<211> LENGTH: 9
<212> TYPE: PRT
<213> ORGANISM: Artificial Sequence
<220> FEATURE:
<223> OTHER INFORMATION: synthetic ADAMTS-2 splice isoform 1 tryptic
      digest peptide

<400> SEQUENCE: 147

Ile Gln Glu Leu Ile Asp Glu Met Arg
1               5
```

```
<210> SEQ ID NO 148
<211> LENGTH: 9
<212> TYPE: PRT
<213> ORGANISM: Artificial Sequence
<220> FEATURE:
<223> OTHER INFORMATION: synthetic cask-interacting protein 2 tryptic
      digest peptide

<400> SEQUENCE: 148

Lys Gly Pro Pro Pro Pro Pro Pro Lys
1               5

<210> SEQ ID NO 149
<211> LENGTH: 8
<212> TYPE: PRT
<213> ORGANISM: Artificial Sequence
<220> FEATURE:
<223> OTHER INFORMATION: synthetic serine/arginine repetitive matrix 1
      tryptic digest peptide

<400> SEQUENCE: 149

Arg Thr Pro Thr Pro Pro Pro Arg
1               5

<210> SEQ ID NO 150
<211> LENGTH: 9
<212> TYPE: PRT
<213> ORGANISM: Artificial Sequence
<220> FEATURE:
<223> OTHER INFORMATION: synthetic serine/arginine repetitive matrix 1
      tryptic digest peptide

<400> SEQUENCE: 150

Thr Ala Ser Pro Pro Pro Pro Pro Lys
1               5

<210> SEQ ID NO 151
<211> LENGTH: 8
<212> TYPE: PRT
<213> ORGANISM: Artificial Sequence
<220> FEATURE:
<223> OTHER INFORMATION: synthetic neurofilament triplet H protein
      tryptic digest peptide

<400> SEQUENCE: 151

Leu Leu Glu Gly Glu Glu Cys Arg
1               5

<210> SEQ ID NO 152
<211> LENGTH: 9
<212> TYPE: PRT
<213> ORGANISM: Artificial Sequence
<220> FEATURE:
<223> OTHER INFORMATION: synthetic actin-related protein 5 tryptic
      digest peptide

<400> SEQUENCE: 152

Leu Gln Glu Leu Asn Ala Val Arg Arg
1               5

<210> SEQ ID NO 153
<211> LENGTH: 9
<212> TYPE: PRT
<213> ORGANISM: Artificial Sequence
<220> FEATURE:
<223> OTHER INFORMATION: synthetic actin-related protein 5 tryptic
      digest peptide
```

<400> SEQUENCE: 153

Leu Gln Glu Leu Asn Ala Tyr Arg Arg
1               5

<210> SEQ ID NO 154
<211> LENGTH: 11
<212> TYPE: PRT
<213> ORGANISM: Artificial Sequence
<220> FEATURE:
<223> OTHER INFORMATION: synthetic similar to Ig gamma-3 chain C region
      tryptic digest peptide

<400> SEQUENCE: 154

Glu Pro Gln Val Tyr Thr Leu Pro Pro Ser Arg
1               5                   10

<210> SEQ ID NO 155
<211> LENGTH: 9
<212> TYPE: PRT
<213> ORGANISM: Artificial Sequence
<220> FEATURE:
<223> OTHER INFORMATION: synthetic similar to heterogeneous nuclear
      ribonucleoprotein K tryptic digest peptide

<400> SEQUENCE: 155

Gly Pro Pro Pro Pro Leu Thr Gly Arg
1               5

<210> SEQ ID NO 156
<211> LENGTH: 9
<212> TYPE: PRT
<213> ORGANISM: Artificial Sequence
<220> FEATURE:
<223> OTHER INFORMATION: synthetic airway trypsin-like protease tryptic
      digest peptide

<400> SEQUENCE: 156

Leu Glu Asn Ser Val Thr Phe Thr Lys
1               5

<210> SEQ ID NO 157
<211> LENGTH: 6
<212> TYPE: PRT
<213> ORGANISM: Artificial Sequence
<220> FEATURE:
<223> OTHER INFORMATION: synthetic metaxin 1 isoform 1 tryptic digest
      peptide

<400> SEQUENCE: 157

Leu Gln Val His Leu Arg
1               5

<210> SEQ ID NO 158
<211> LENGTH: 9
<212> TYPE: PRT
<213> ORGANISM: Artificial Sequence
<220> FEATURE:
<223> OTHER INFORMATION: synthetic metaxin 1 isoform 1 tryptic digest
      peptide

<400> SEQUENCE: 158

Ser Pro Arg Ser Gly Thr Ser Pro Lys
1               5

<210> SEQ ID NO 159
<211> LENGTH: 7

```
<212> TYPE: PRT
<213> ORGANISM: Artificial Sequence
<220> FEATURE:
<223> OTHER INFORMATION: synthetic OTTHUMP00000021786 tryptic digest
      peptide

<400> SEQUENCE: 159

Phe Ala Ser Phe Ile Asp Lys
1               5

<210> SEQ ID NO 160
<211> LENGTH: 11
<212> TYPE: PRT
<213> ORGANISM: Artificial Sequence
<220> FEATURE:
<223> OTHER INFORMATION: synthetic OTTHUMP00000059857 tryptic digest
      peptide

<400> SEQUENCE: 160

Gly Thr Asn Tyr Leu Ala Asp Val Phe Glu Lys
1               5                   10

<210> SEQ ID NO 161
<211> LENGTH: 6
<212> TYPE: PRT
<213> ORGANISM: Artificial Sequence
<220> FEATURE:
<223> OTHER INFORMATION: synthetic 9 kDa protein tryptic digest peptide

<400> SEQUENCE: 161

Met Gln Ile Phe Val Lys
1               5

<210> SEQ ID NO 162
<211> LENGTH: 9
<212> TYPE: PRT
<213> ORGANISM: Artificial Sequence
<220> FEATURE:
<223> OTHER INFORMATION: synthetic 9 kDa protein tryptic digest peptide

<400> SEQUENCE: 162

Thr Leu Ser Asn Tyr Asn Ile Gln Lys
1               5

<210> SEQ ID NO 163
<211> LENGTH: 7
<212> TYPE: PRT
<213> ORGANISM: Artificial Sequence
<220> FEATURE:
<223> OTHER INFORMATION: synthetic 42 kDa protein and 43 kDa protein
      tryptic digest peptide

<400> SEQUENCE: 163

Leu Ala Ser Tyr Leu Asp Lys
1               5

<210> SEQ ID NO 164
<211> LENGTH: 13
<212> TYPE: PRT
<213> ORGANISM: Artificial Sequence
<220> FEATURE:
<223> OTHER INFORMATION: synthetic 43 kDa protein tryptic digest peptide

<400> SEQUENCE: 164

Ala Ser Leu Glu Asn Ser Leu Glu Glu Thr Lys Gly Arg
1               5                   10
```

-continued

```
<210> SEQ ID NO 165
<211> LENGTH: 9
<212> TYPE: PRT
<213> ORGANISM: Artificial Sequence
<220> FEATURE:
<223> OTHER INFORMATION: synthetic 43 kDa protein and 50 kDa protein
      tryptic digest peptide

<400> SEQUENCE: 165

Asp Ala Glu Asp Trp Phe Phe Ser Lys
1               5

<210> SEQ ID NO 166
<211> LENGTH: 13
<212> TYPE: PRT
<213> ORGANISM: Artificial Sequence
<220> FEATURE:
<223> OTHER INFORMATION: synthetic 43 kDa protein tryptic digest peptide

<400> SEQUENCE: 166

Glu Val Ala Thr Asn Ser Glu Leu Val Gln Ser Gly Lys
1               5                   10

<210> SEQ ID NO 167
<211> LENGTH: 9
<212> TYPE: PRT
<213> ORGANISM: Artificial Sequence
<220> FEATURE:
<223> OTHER INFORMATION: synthetic 43 kDa protein tryptic digest peptide

<400> SEQUENCE: 167

Val Leu Asp Glu Leu Thr Leu Ala Arg
1               5

<210> SEQ ID NO 168
<211> LENGTH: 14
<212> TYPE: PRT
<213> ORGANISM: Artificial Sequence
<220> FEATURE:
<223> OTHER INFORMATION: synthetic 86 kDa protein and hypothetical
      protein DKFZp686E03231 tryptic digest peptide

<400> SEQUENCE: 168

Phe Gly Gln Gly Ser Gly Pro Ile Val Leu Asp Asp Val Arg
1               5                   10

<210> SEQ ID NO 169
<211> LENGTH: 8
<212> TYPE: PRT
<213> ORGANISM: Artificial Sequence
<220> FEATURE:
<223> OTHER INFORMATION: synthetic 86 kDa protein tryptic digest peptide

<400> SEQUENCE: 169

Gly Arg Val Glu Val Leu Tyr Arg
1               5

<210> SEQ ID NO 170
<211> LENGTH: 15
<212> TYPE: PRT
<213> ORGANISM: Artificial Sequence
<220> FEATURE:
<223> OTHER INFORMATION: synthetic 86 kDa protein and 172 kDa protein
      tryptic digest peptide

<400> SEQUENCE: 170

Gln Leu Gly Cys Gly Trp Ala Thr Ser Ala Pro Gly Asn Ala Arg
1               5                   10                  15
```

<210> SEQ ID NO 171
<211> LENGTH: 6
<212> TYPE: PRT
<213> ORGANISM: Artificial Sequence
<220> FEATURE:
<223> OTHER INFORMATION: synthetic 86 kDa protein tryptic digest peptide

<400> SEQUENCE: 171

Val Glu Val Leu Tyr Arg
1               5

<210> SEQ ID NO 172
<211> LENGTH: 15
<212> TYPE: PRT
<213> ORGANISM: Artificial Sequence
<220> FEATURE:
<223> OTHER INFORMATION: synthetic hypothetical protein DKFZp686O16217
      tryptic digest peptide

<400> SEQUENCE: 172

Asp Ala Ser Gly Ala Thr Phe Thr Trp Thr Pro Ser Ser Gly Lys
1               5                   10                  15

<210> SEQ ID NO 173
<211> LENGTH: 32
<212> TYPE: PRT
<213> ORGANISM: Artificial Sequence
<220> FEATURE:
<223> OTHER INFORMATION: synthetic hypothetical protein DKFZp686O16217
      tryptic digest peptide

<400> SEQUENCE: 173

Ser Gly Asn Thr Phe Arg Pro Glu Val His Leu Leu Pro Pro Ser
1               5                   10                  15

Glu Glu Leu Ala Leu Asn Glu Leu Val Thr Leu Thr Cys Leu Ala Arg
            20                  25                  30

<210> SEQ ID NO 174
<211> LENGTH: 11
<212> TYPE: PRT
<213> ORGANISM: Artificial Sequence
<220> FEATURE:
<223> OTHER INFORMATION: synthetic hypothetical protein DKFZp686O16217
      tryptic digest peptide

<400> SEQUENCE: 174

Val Pro Pro Pro Pro Cys Cys His Pro Arg
1               5                   10

<210> SEQ ID NO 175
<211> LENGTH: 10
<212> TYPE: PRT
<213> ORGANISM: Artificial Sequence
<220> FEATURE:
<223> OTHER INFORMATION: synthetic hypothetical protein DKFZp686O16217
      tryptic digest peptide

<400> SEQUENCE: 175

Trp Leu Gln Gly Ser Gln Glu Leu Pro Arg
1               5                   10

<210> SEQ ID NO 176
<211> LENGTH: 12
<212> TYPE: PRT
<213> ORGANISM: Artificial Sequence
<220> FEATURE:

<223> OTHER INFORMATION: synthetic hypothetical protein tryptic digest
      peptide

<400> SEQUENCE: 176

Asp Ile Cys Asn Asp Val Leu Ser Leu Leu Glu Lys
1               5                   10

<210> SEQ ID NO 177
<211> LENGTH: 8
<212> TYPE: PRT
<213> ORGANISM: Artificial Sequence
<220> FEATURE:
<223> OTHER INFORMATION: synthetic hypothetical protein tryptic digest
      peptide

<400> SEQUENCE: 177

Asn Leu Leu Ser Val Ala Tyr Lys
1               5

<210> SEQ ID NO 178
<211> LENGTH: 17
<212> TYPE: PRT
<213> ORGANISM: Artificial Sequence
<220> FEATURE:
<223> OTHER INFORMATION: synthetic Rho GDP-dissociation inhibitor 2
      (ARHGDIB) tryptic digest peptide

<400> SEQUENCE: 178

Ala Pro Glu Pro His Val Glu Glu Asp Asp Asp Glu Leu Asp Ser
1               5                   10                  15

Lys

<210> SEQ ID NO 179
<211> LENGTH: 8
<212> TYPE: PRT
<213> ORGANISM: Artificial Sequence
<220> FEATURE:
<223> OTHER INFORMATION: synthetic Rho GDP-dissociation inhibitor 2
      (ARHGDIB) tryptic digest peptide

<400> SEQUENCE: 179

Ala Pro Asn Val Val Val Thr Arg
1               5

<210> SEQ ID NO 180
<211> LENGTH: 7
<212> TYPE: PRT
<213> ORGANISM: Artificial Sequence
<220> FEATURE:
<223> OTHER INFORMATION: synthetic Rho GDP-dissociation inhibitor 2
      (ARHGDIB) tryptic digest peptide

<400> SEQUENCE: 180

Asp Asp Glu Ser Leu Ile Lys
1               5

<210> SEQ ID NO 181
<211> LENGTH: 7
<212> TYPE: PRT
<213> ORGANISM: Artificial Sequence
<220> FEATURE:
<223> OTHER INFORMATION: synthetic Rho GDP-dissociation inhibitor 2
      (ARHGDIB) tryptic digest peptide

<400> SEQUENCE: 181

Glu Leu Gln Glu Met Asp Lys
1               5

<210> SEQ ID NO 182
<211> LENGTH: 13
<212> TYPE: PRT
<213> ORGANISM: Artificial Sequence
<220> FEATURE:
<223> OTHER INFORMATION: synthetic Rho GDP-dissociation inhibitor 2
      (ARHGDIB) tryptic digest peptide

<400> SEQUENCE: 182

Thr Leu Leu Gly Asp Gly Pro Val Val Thr Asp Pro Lys
1               5                   10

<210> SEQ ID NO 183
<211> LENGTH: 11
<212> TYPE: PRT
<213> ORGANISM: Artificial Sequence
<220> FEATURE:
<223> OTHER INFORMATION: synthetic calgranulin A tryptic digest peptide

<400> SEQUENCE: 183

Ala Leu Asn Ser Ile Ile Asp Val Tyr His Lys
1               5                   10

<210> SEQ ID NO 184
<211> LENGTH: 21
<212> TYPE: PRT
<213> ORGANISM: Artificial Sequence
<220> FEATURE:
<223> OTHER INFORMATION: synthetic calgranulin A tryptic digest peptide

<400> SEQUENCE: 184

Glu Leu Asp Ile Asn Thr Asp Gly Ala Val Asn Phe Gln Glu Phe Leu
1               5                   10                  15

Ile Leu Val Ile Lys
            20

<210> SEQ ID NO 185
<211> LENGTH: 7
<212> TYPE: PRT
<213> ORGANISM: Artificial Sequence
<220> FEATURE:
<223> OTHER INFORMATION: synthetic calgranulin A tryptic digest peptide

<400> SEQUENCE: 185

Gly Ala Asp Val Trp Phe Lys
1               5

<210> SEQ ID NO 186
<211> LENGTH: 8
<212> TYPE: PRT
<213> ORGANISM: Artificial Sequence
<220> FEATURE:
<223> OTHER INFORMATION: synthetic calgranulin A tryptic digest peptide

<400> SEQUENCE: 186

Gly Asn Phe His Ala Val Tyr Arg
1               5

<210> SEQ ID NO 187
<211> LENGTH: 12
<212> TYPE: PRT
<213> ORGANISM: Artificial Sequence
<220> FEATURE:
<223> OTHER INFORMATION: synthetic calgranulin A tryptic digest peptide

<400> SEQUENCE: 187

```
Gly Asn Phe His Ala Val Tyr Arg Asp Asp Leu Lys
1               5                   10
```

<210> SEQ ID NO 188
<211> LENGTH: 8
<212> TYPE: PRT
<213> ORGANISM: Artificial Sequence
<220> FEATURE:
<223> OTHER INFORMATION: synthetic calgranulin A tryptic digest peptide

<400> SEQUENCE: 188

```
Lys Gly Ala Asp Val Trp Phe Lys
1               5
```

<210> SEQ ID NO 189
<211> LENGTH: 11
<212> TYPE: PRT
<213> ORGANISM: Artificial Sequence
<220> FEATURE:
<223> OTHER INFORMATION: synthetic calgranulin A tryptic digest peptide

<400> SEQUENCE: 189

```
Leu Leu Glu Thr Glu Cys Pro Gln Tyr Ile Arg
1               5                   10
```

<210> SEQ ID NO 190
<211> LENGTH: 7
<212> TYPE: PRT
<213> ORGANISM: Artificial Sequence
<220> FEATURE:
<223> OTHER INFORMATION: synthetic calgranulin A tryptic digest peptide

<400> SEQUENCE: 190

```
Met Leu Thr Glu Leu Glu Lys
1               5
```

<210> SEQ ID NO 191
<211> LENGTH: 7
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 191

```
Asp Leu Gln Asn Phe Leu Lys
1               5
```

<210> SEQ ID NO 192
<211> LENGTH: 8
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 192

```
Asp Leu Gln Asn Phe Leu Lys Lys
1               5
```

<210> SEQ ID NO 193
<211> LENGTH: 8
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 193

Lys Asp Leu Gln Asn Phe Leu Lys
1               5

<210> SEQ ID NO 194
<211> LENGTH: 13
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 194

Leu Gly His Pro Asp Thr Leu Asn Gln Gly Glu Phe Lys
1               5                   10

<210> SEQ ID NO 195
<211> LENGTH: 17
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 195

Leu Gly His Pro Asp Thr Leu Asn Gln Gly Glu Phe Lys Glu Leu Val
1               5                   10                  15

Arg

<210> SEQ ID NO 196
<211> LENGTH: 8
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 196

Leu Thr Trp Ala Ser His Glu Lys
1               5

<210> SEQ ID NO 197
<211> LENGTH: 6
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 197

Met Ser Gln Leu Glu Arg
1               5

<210> SEQ ID NO 198
<211> LENGTH: 14
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 198

Asn Ile Glu Thr Ile Asn Thr His Phe Gln Tyr Ser Val Lys
1               5                   10

```
<210> SEQ ID NO 199
<211> LENGTH: 13
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 199

Gln Leu Ser Phe Glu Glu Phe Ile Met Leu Met Ala Arg
1               5                   10

<210> SEQ ID NO 200
<211> LENGTH: 15
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 200

Val Ile Glu His Ile Met Glu Asp Leu Asp Thr Asn Ala Asp Lys
1               5                   10                  15

<210> SEQ ID NO 201
<211> LENGTH: 28
<212> TYPE: PRT
<213> ORGANISM: Artificial Sequence
<220> FEATURE:
<223> OTHER INFORMATION: synthetic calgranulin B (MRP14) tryptic digest
      peptide

<400> SEQUENCE: 201

Val Ile Glu His Ile Met Glu Asp Leu Asp Thr Asn Ala Asp Lys Gln
1               5                   10                  15

Leu Ser Phe Glu Glu Phe Ile Met Leu Met Ala Arg
            20                  25

<210> SEQ ID NO 202
<211> LENGTH: 7
<212> TYPE: PRT
<213> ORGANISM: Artificial Sequence
<220> FEATURE:
<223> OTHER INFORMATION: synthetic thymosin-like 4 tryptic digest
      peptide

<400> SEQUENCE: 202

Glu Thr Ile Glu Gln Glu Lys
1               5

<210> SEQ ID NO 203
<211> LENGTH: 13
<212> TYPE: PRT
<213> ORGANISM: Artificial Sequence
<220> FEATURE:
<223> OTHER INFORMATION: synthetic thymosin-like 4 tryptic digest
      peptide

<400> SEQUENCE: 203

Asn Pro Leu Pro Ser Lys Glu Thr Ile Glu Gln Glu Lys
1               5                   10

<210> SEQ ID NO 204
<211> LENGTH: 11
<212> TYPE: PRT
<213> ORGANISM: Artificial Sequence
<220> FEATURE:
<223> OTHER INFORMATION: synthetic thymosin-like 4 tryptic digest
```

```
                    peptide

<400> SEQUENCE: 204

Ser Asp Lys Pro Asp Met Ala Glu Ile Glu Lys
1               5                   10

<210> SEQ ID NO 205
<211> LENGTH: 14
<212> TYPE: PRT
<213> ORGANISM: Artificial Sequence
<220> FEATURE:
<223> OTHER INFORMATION: synthetic thymosin-like 4 tryptic digest
      peptide

<400> SEQUENCE: 205

Ser Asp Lys Pro Asp Met Ala Glu Ile Glu Lys Phe Asp Lys
1               5                   10

<210> SEQ ID NO 206
<211> LENGTH: 14
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 206

Asp Ser Leu Leu Gln Asp Gly Glu Phe Ser Met Asp Leu Arg
1               5                   10

<210> SEQ ID NO 207
<211> LENGTH: 12
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 207

Asp Ser Pro Ser Val Trp Ala Ala Val Pro Gly Lys
1               5                   10

<210> SEQ ID NO 208
<211> LENGTH: 10
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 208

Glu Gly Val His Gly Gly Leu Ile Asn Lys
1               5                   10

<210> SEQ ID NO 209
<211> LENGTH: 14
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 209

Ser Ser Phe Tyr Val Asn Gly Leu Thr Leu Gly Gly Gln Lys
1               5                   10

<210> SEQ ID NO 210
```

```
<211> LENGTH: 14
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 210

Ser Thr Gly Gly Ala Pro Thr Phe Met Val Thr Val Thr Lys
1               5                   10

<210> SEQ ID NO 211
<211> LENGTH: 11
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 211

Thr Asp Lys Thr Leu Val Leu Leu Met Gly Lys
1               5                   10

<210> SEQ ID NO 212
<211> LENGTH: 16
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 212

Thr Phe Val Asn Ile Thr Pro Ala Glu Val Gly Val Leu Val Gly Lys
1               5                   10                  15

<210> SEQ ID NO 213
<211> LENGTH: 8
<212> TYPE: PRT
<213> ORGANISM: Artificial Sequence
<220> FEATURE:
<223> OTHER INFORMATION: synthetic profilin 1 (PFN1) tryptic digest
      peptide

<400> SEQUENCE: 213

Thr Leu Val Leu Leu Met Gly Lys
1               5

<210> SEQ ID NO 214
<211> LENGTH: 12
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 214

Gly Thr Ser Ala Val Asn Val Val Leu Ser Leu Lys
1               5                   10

<210> SEQ ID NO 215
<211> LENGTH: 15
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 215
```

Leu Lys Pro Leu Leu Asn Thr Met Ile Gln Ser Asn Tyr Asn Arg
1               5                   10                  15

<210> SEQ ID NO 216
<211> LENGTH: 12
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 216

Leu Val Gly Ile Gln Ile Gln Thr Leu Met Gln Lys
1               5                   10

<210> SEQ ID NO 217
<211> LENGTH: 8
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 217

Asn Gly Glu Asn Leu Glu Val Arg
1               5

<210> SEQ ID NO 218
<211> LENGTH: 10
<212> TYPE: PRT
<213> ORGANISM: Artificial Sequence
<220> FEATURE:
<223> OTHER INFORMATION: synthetic short palate, lung and nasal
      epithelium carcinoma associated protein 2 tryptic digest peptide

<400> SEQUENCE: 218

Phe Val Asn Ser Val Ile Asn Thr Leu Lys
1               5                   10

<210> SEQ ID NO 219
<211> LENGTH: 10
<212> TYPE: PRT
<213> ORGANISM: Artificial Sequence
<220> FEATURE:
<223> OTHER INFORMATION: synthetic short palate, lung and nasal
      epithelium carcinoma associated protein 2 tryptic digest peptide

<400> SEQUENCE: 219

Ile Ser Asn Ser Leu Ile Leu Asp Val Lys
1               5                   10

<210> SEQ ID NO 220
<211> LENGTH: 12
<212> TYPE: PRT
<213> ORGANISM: Artificial Sequence
<220> FEATURE:
<223> OTHER INFORMATION: synthetic short palate, lung and nasal
      epithelium carcinoma associated protein 2 tryptic digest peptide

<400> SEQUENCE: 220

Leu Leu Pro Thr Asn Thr Asp Ile Phe Gly Leu Lys
1               5                   10

<210> SEQ ID NO 221
<211> LENGTH: 9
<212> TYPE: PRT
<213> ORGANISM: Artificial Sequence
<220> FEATURE:

```
<223> OTHER INFORMATION: synthetic short palate, lung and nasal
      epithelium carcinoma associated protein 2 tryptic digest peptide

<400> SEQUENCE: 221

Ser Thr Val Ser Ser Leu Leu Gln Lys
1               5

<210> SEQ ID NO 222
<211> LENGTH: 7
<212> TYPE: PRT
<213> ORGANISM: Artificial Sequence
<220> FEATURE:
<223> OTHER INFORMATION: synthetic short palate, lung and nasal
      epithelium carcinoma associated protein 2 tryptic digest peptide

<400> SEQUENCE: 222

Thr Gln Leu Gln Thr Leu Ile
1               5

<210> SEQ ID NO 223
<211> LENGTH: 8
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 223

Ala Val Leu Thr Ile Asp Glu Lys
1               5

<210> SEQ ID NO 224
<211> LENGTH: 19
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 224

Leu Ser Asp Val Ser Ser Gly Glu Leu Ala Leu Ile Leu Ala Leu Gly
1               5                   10                  15

Val Cys Arg

<210> SEQ ID NO 225
<211> LENGTH: 7
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 225

Thr Phe Leu Asp Ile Asn Lys
1               5

<210> SEQ ID NO 226
<211> LENGTH: 22
<212> TYPE: PRT
<213> ORGANISM: Artificial Sequence
<220> FEATURE:
<223> OTHER INFORMATION: synthetic transcobalamin 1 tryptic digest
      peptide

<400> SEQUENCE: 226

Thr Tyr Trp Glu Leu Leu Ser Gly Gly Glu Pro Leu Ser Gln Gly Ala
1               5                   10                  15
```

```
Gly Ser Tyr Val Val Arg
            20

<210> SEQ ID NO 227
<211> LENGTH: 7
<212> TYPE: PRT
<213> ORGANISM: Artificial Sequence
<220> FEATURE:
<223> OTHER INFORMATION: synthetic short palate, lung and nasal
      epithelium carcinoma associated protein 2 tryptic digest peptide

<400> SEQUENCE: 227

Glu Ile Cys Pro Leu Ile Arg
1               5

<210> SEQ ID NO 228
<211> LENGTH: 19
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 228

Leu Tyr His Ser Glu Ala Phe Thr Val Asn Phe Gly Asp Thr Glu Glu
1               5                   10                  15

Ala Lys Lys

<210> SEQ ID NO 229
<211> LENGTH: 13
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 229

Asp Thr Val Phe Ala Leu Val Asn Tyr Ile Phe Phe Lys
1               5                   10

<210> SEQ ID NO 230
<211> LENGTH: 17
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 230

Glu Leu Asp Arg Asp Thr Val Phe Ala Leu Val Asn Tyr Ile Phe Phe
1               5                   10                  15

Lys

<210> SEQ ID NO 231
<211> LENGTH: 15
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 231

Phe Asn Lys Pro Phe Val Phe Leu Met Ile Glu Gln Asn Thr Lys
1               5                   10                  15
```

```
<210> SEQ ID NO 232
<211> LENGTH: 15
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 232

Leu Gln His Leu Glu Asn Glu Leu Thr His Asp Ile Ile Thr Lys
1               5                   10                  15

<210> SEQ ID NO 233
<211> LENGTH: 10
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 233

Leu Ser Ile Thr Gly Thr Tyr Asp Leu Lys
1               5                   10

<210> SEQ ID NO 234
<211> LENGTH: 9
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 234

Leu Ser Ser Trp Val Leu Leu Met Lys
1               5

<210> SEQ ID NO 235
<211> LENGTH: 10
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 235

Leu Val Asp Lys Phe Leu Glu Asp Val Lys
1               5                   10

<210> SEQ ID NO 236
<211> LENGTH: 8
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 236

Gln Ile Asn Asp Tyr Val Glu Lys
1               5

<210> SEQ ID NO 237
<211> LENGTH: 7
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 237
```

```
Ser Pro Leu Phe Met Gly Lys
1               5
```

<210> SEQ ID NO 238
<211> LENGTH: 10
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 238

```
Ser Val Leu Gly Gln Leu Gly Ile Thr Lys
1               5                   10
```

<210> SEQ ID NO 239
<211> LENGTH: 24
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 239

```
Thr Leu Asn Gln Phe Asp Ser Gln Leu Gln Leu Thr Thr Gly Asn Gly
1               5                   10                  15

Leu Phe Leu Ser Glu Gly Leu Lys
            20
```

<210> SEQ ID NO 240
<211> LENGTH: 18
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 240

```
Val Phe Ser Asn Gly Ala Asp Leu Ser Gly Val Thr Glu Glu Ala Pro
1               5                   10                  15

Leu Lys
```

<210> SEQ ID NO 241
<211> LENGTH: 7
<212> TYPE: PRT
<213> ORGANISM: Artificial Sequence
<220> FEATURE:
<223> OTHER INFORMATION: synthetic alpha-1-antitrypsin tryptic digest
      peptide

<400> SEQUENCE: 241

```
Val Val Asn Pro Thr Gln Lys
1               5
```

<210> SEQ ID NO 242
<211> LENGTH: 14
<212> TYPE: PRT
<213> ORGANISM: Artificial Sequence
<220> FEATURE:
<223> OTHER INFORMATION: synthetic prothymosin alpha tryptic digest
      peptide

<400> SEQUENCE: 242

```
Ser Asp Ala Ala Val Asp Thr Ser Ser Glu Ile Thr Thr Lys
1               5                   10
```

<210> SEQ ID NO 243
<211> LENGTH: 12
<212> TYPE: PRT
<213> ORGANISM: Artificial Sequence
<220> FEATURE:
<223> OTHER INFORMATION: synthetic cofilin 1 (non-muscle) tryptic digest
      peptide

<400> SEQUENCE: 243

Ala Ser Gly Val Ala Val Ser Asp Gly Val Ile Lys
1               5                   10

<210> SEQ ID NO 244
<211> LENGTH: 6
<212> TYPE: PRT
<213> ORGANISM: Artificial Sequence
<220> FEATURE:
<223> OTHER INFORMATION: synthetic cofilin 1 (non-muscle) tryptic digest
      peptide

<400> SEQUENCE: 244

Val Phe Asn Asp Met Lys
1               5

<210> SEQ ID NO 245
<211> LENGTH: 8
<212> TYPE: PRT
<213> ORGANISM: Artificial Sequence
<220> FEATURE:
<223> OTHER INFORMATION: synthetic annexin 1 tryptic digest peptide

<400> SEQUENCE: 245

Ala Met Val Ser Glu Phe Leu Lys
1               5

<210> SEQ ID NO 246
<211> LENGTH: 8
<212> TYPE: PRT
<213> ORGANISM: Artificial Sequence
<220> FEATURE:
<223> OTHER INFORMATION: synthetic annexin 1 tryptic digest peptide

<400> SEQUENCE: 246

Asn Ala Leu Leu Ser Leu Ala Lys
1               5

<210> SEQ ID NO 247
<211> LENGTH: 11
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 247

Ala Thr Glu His Leu Ser Thr Leu Ser Glu Lys
1               5                   10

<210> SEQ ID NO 248
<211> LENGTH: 11
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 248

Asp Leu Ala Thr Val Tyr Val Asp Val Leu Lys
1               5                   10

<210> SEQ ID NO 249
<211> LENGTH: 17
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 249

Asp Ser Gly Arg Asp Tyr Val Ser Gln Phe Glu Gly Ser Ala Leu Gly
1               5                   10                  15

Lys

<210> SEQ ID NO 250
<211> LENGTH: 13
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 250

Asp Tyr Val Ser Gln Phe Glu Gly Ser Ala Leu Gly Lys
1               5                   10

<210> SEQ ID NO 251
<211> LENGTH: 9
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 251

Leu Ser Pro Leu Gly Glu Glu Met Arg
1               5

<210> SEQ ID NO 252
<211> LENGTH: 11
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 252

Gln Gly Leu Leu Pro Val Leu Glu Ser Phe Lys
1               5                   10

<210> SEQ ID NO 253
<211> LENGTH: 11
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 253

Thr His Leu Ala Pro Tyr Ser Asp Glu Leu Arg
1               5                   10

<210> SEQ ID NO 254
<211> LENGTH: 13
<212> TYPE: PRT

```
<213> ORGANISM: Artificial Sequence
<220> FEATURE:
<223> OTHER INFORMATION: synthetic apolipoprotein A-1 tryptic digest
      peptide

<400> SEQUENCE: 254

Val Lys Asp Leu Ala Thr Val Tyr Val Asp Val Leu Lys
1               5                   10

<210> SEQ ID NO 255
<211> LENGTH: 10
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 255

Val Gln Pro Tyr Leu Asp Asp Phe Gln Lys
1               5                   10

<210> SEQ ID NO 256
<211> LENGTH: 12
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 256

Val Ser Phe Leu Ser Ala Leu Glu Glu Tyr Thr Lys
1               5                   10

<210> SEQ ID NO 257
<211> LENGTH: 11
<212> TYPE: PRT
<213> ORGANISM: Artificial Sequence
<220> FEATURE:
<223> OTHER INFORMATION: synthetic 5 kDa protein (TMSL2) tryptic digest
      peptide

<400> SEQUENCE: 257

Ser Asp Lys Pro Asp Met Ala Glu Ile Glu Lys
1               5                   10

<210> SEQ ID NO 258
<211> LENGTH: 14
<212> TYPE: PRT
<213> ORGANISM: Artificial Sequence
<220> FEATURE:
<223> OTHER INFORMATION: synthetic 5 kDa protein (TMSL2) tryptic digest
      peptide

<400> SEQUENCE: 258

Ser Asp Lys Pro Asp Met Ala Glu Ile Glu Lys Phe Asp Lys
1               5                   10

<210> SEQ ID NO 259
<211> LENGTH: 12
<212> TYPE: PRT
<213> ORGANISM: Artificial Sequence
<220> FEATURE:
<223> OTHER INFORMATION: synthetic 5 kDa protein (TMSL2) tryptic digest
      peptide

<400> SEQUENCE: 259

Thr Glu Thr Gln Glu Lys Asn Pro Leu Pro Ser Lys
1               5                   10
```

<210> SEQ ID NO 260
<211> LENGTH: 9
<212> TYPE: PRT
<213> ORGANISM: Artificial Sequence
<220> FEATURE:
<223> OTHER INFORMATION: synthetic Golgi membrane protein GP73 tryptic
      digest peptide

<400> SEQUENCE: 260

Asp Thr Ile Asn Leu Leu Asp Gln Arg
1               5

<210> SEQ ID NO 261
<211> LENGTH: 7
<212> TYPE: PRT
<213> ORGANISM: Artificial Sequence
<220> FEATURE:
<223> OTHER INFORMATION: synthetic calmodulin tryptic digest peptide

<400> SEQUENCE: 261

Glu Leu Gly Thr Val Met Arg
1               5

<210> SEQ ID NO 262
<211> LENGTH: 14
<212> TYPE: PRT
<213> ORGANISM: Artificial Sequence
<220> FEATURE:
<223> OTHER INFORMATION: synthetic Golgi membrane protein GP73 tryptic
      digest peptide

<400> SEQUENCE: 262

Ile Gln Ser Ser His Asn Phe Gln Leu Glu Ser Val Asn Lys
1               5                   10

<210> SEQ ID NO 263
<211> LENGTH: 10
<212> TYPE: PRT
<213> ORGANISM: Artificial Sequence
<220> FEATURE:
<223> OTHER INFORMATION: synthetic Golgi membrane protein GP73 tryptic
      digest peptide

<400> SEQUENCE: 263

Leu Gln Gln Asp Val Leu Gln Phe Gln Lys
1               5                   10

<210> SEQ ID NO 264
<211> LENGTH: 13
<212> TYPE: PRT
<213> ORGANISM: Artificial Sequence
<220> FEATURE:
<223> OTHER INFORMATION: synthetic calmodulin tryptic digest peptide

<400> SEQUENCE: 264

Ala Asp Gln Leu Thr Glu Glu Gln Ile Ala Glu Phe Lys
1               5                   10

<210> SEQ ID NO 265
<211> LENGTH: 17
<212> TYPE: PRT
<213> ORGANISM: Artificial Sequence
<220> FEATURE:
<223> OTHER INFORMATION: synthetic calmodulin tryptic digest peptide

<400> SEQUENCE: 265

Glu Ala Phe Ser Leu Phe Asp Lys Asp Gly Asp Gly Thr Ile Thr Thr
1               5                   10                  15
Lys

<210> SEQ ID NO 266
<211> LENGTH: 9
<212> TYPE: PRT
<213> ORGANISM: Artificial Sequence
<220> FEATURE:
<223> OTHER INFORMATION: synthetic lysozyme C tryptic digest peptide

<400> SEQUENCE: 266

Ala Thr Asn Tyr Asn Ala Gly Asp Arg
1               5

<210> SEQ ID NO 267
<211> LENGTH: 6
<212> TYPE: PRT
<213> ORGANISM: Artificial Sequence
<220> FEATURE:
<223> OTHER INFORMATION: synthetic lysozyme C tryptic digest peptide

<400> SEQUENCE: 267

Ala Trp Val Ala Trp Arg
1               5

<210> SEQ ID NO 268
<211> LENGTH: 7
<212> TYPE: PRT
<213> ORGANISM: Artificial Sequence
<220> FEATURE:
<223> OTHER INFORMATION: synthetic lysozyme C tryptic digest peptide

<400> SEQUENCE: 268

Leu Gly Met Asp Gly Tyr Arg
1               5

<210> SEQ ID NO 269
<211> LENGTH: 12
<212> TYPE: PRT
<213> ORGANISM: Artificial Sequence
<220> FEATURE:
<223> OTHER INFORMATION: synthetic lysozyme C tryptic digest peptide

<400> SEQUENCE: 269

Ser Thr Asp Tyr Gly Ile Phe Gln Ile Asn Ser Arg
1               5                   10

<210> SEQ ID NO 270
<211> LENGTH: 8
<212> TYPE: PRT
<213> ORGANISM: Artificial Sequence
<220> FEATURE:
<223> OTHER INFORMATION: synthetic lysozyme C tryptic digest peptide

<400> SEQUENCE: 270

Trp Glu Ser Gly Tyr Asn Thr Arg
1               5

<210> SEQ ID NO 271
<211> LENGTH: 10
<212> TYPE: PRT
<213> ORGANISM: Artificial Sequence
<220> FEATURE:
<223> OTHER INFORMATION: synthetic beta-2-microglobulin tryptic digest
      peptide

```
<400> SEQUENCE: 271

Val Glu His Ser Asp Leu Ser Phe Ser Lys
1               5                   10

<210> SEQ ID NO 272
<211> LENGTH: 10
<212> TYPE: PRT
<213> ORGANISM: Artificial Sequence
<220> FEATURE:
<223> OTHER INFORMATION: synthetic beta-2-microglobulin tryptic digest
      peptide

<400> SEQUENCE: 272

Val Asn His Val Thr Leu Ser Gln Pro Lys
1               5                   10

<210> SEQ ID NO 273
<211> LENGTH: 13
<212> TYPE: PRT
<213> ORGANISM: Artificial Sequence
<220> FEATURE:
<223> OTHER INFORMATION: synthetic kallikrein 1 tryptic digest peptide

<400> SEQUENCE: 273

Leu Thr Glu Pro Ala Asp Thr Ile Thr Asp Ala Val Lys
1               5                   10

<210> SEQ ID NO 274
<211> LENGTH: 10
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 274

Ala Phe Val Asn Cys Asp Glu Asn Ser Arg
1               5                   10

<210> SEQ ID NO 275
<211> LENGTH: 16
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 275

Ala Ser Val Asp Ser Gly Ser Ser Glu Glu Gln Gly Gly Ser Ser Arg
1               5                   10                  15

<210> SEQ ID NO 276
<211> LENGTH: 9
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 276

Ile Ile Glu Gly Glu Pro Asn Leu Lys
1               5

<210> SEQ ID NO 277
<211> LENGTH: 8
<212> TYPE: PRT
<213> ORGANISM: Artificial Sequence
```

```
<220> FEATURE:
<223> OTHER INFORMATION: synthetic polymeric-immunoglobulin receptor
      tryptic digest peptide

<400> SEQUENCE: 277

Ile Ile Leu Asn Pro Gln Asp Lys
1               5

<210> SEQ ID NO 278
<211> LENGTH: 18
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 278

Gln Gly His Phe Tyr Gly Glu Thr Ala Ala Val Tyr Val Ala Val Glu
1               5                   10                  15

Glu Arg

<210> SEQ ID NO 279
<211> LENGTH: 7
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 279

Val Leu Asp Ser Gly Phe Arg
1               5

<210> SEQ ID NO 280
<211> LENGTH: 8
<212> TYPE: PRT
<213> ORGANISM: Artificial Sequence
<220> FEATURE:
<223> OTHER INFORMATION: synthetic lysozyme C tryptic digest peptide

<400> SEQUENCE: 280

Gln Tyr Val Gln Gly Cys Gly Val
1               5

<210> SEQ ID NO 281
<211> LENGTH: 28
<212> TYPE: PRT
<213> ORGANISM: Artificial Sequence
<220> FEATURE:
<223> OTHER INFORMATION: synthetic lysozyme C tryptic digest peptide

<400> SEQUENCE: 281

Thr Pro Gly Ala Val Asn Ala Cys His Leu Ser Cys Ser Ala Leu Leu
1               5                   10                  15

Gln Asp Asn Ile Ala Asp Ala Val Ala Cys Ala Lys
            20                  25

<210> SEQ ID NO 282
<211> LENGTH: 6
<212> TYPE: PRT
<213> ORGANISM: Artificial Sequence
<220> FEATURE:
<223> OTHER INFORMATION: synthetic beta-2-microglobulin tryptic digest
      peptide

<400> SEQUENCE: 282
```

```
Ile Gln Val Tyr Ser Arg
1               5

<210> SEQ ID NO 283
<211> LENGTH: 9
<212> TYPE: PRT
<213> ORGANISM: Artificial Sequence
<220> FEATURE:
<223> OTHER INFORMATION: synthetic kallikrein 1 tryptic digest peptide

<400> SEQUENCE: 283

Ile Leu Pro Asn Asp Glu Cys Glu Lys
1               5

<210> SEQ ID NO 284
<211> LENGTH: 14
<212> TYPE: PRT
<213> ORGANISM: Artificial Sequence
<220> FEATURE:
<223> OTHER INFORMATION: synthetic kallikrein 1 tryptic digest peptide

<400> SEQUENCE: 284

Gln Ala Asp Glu Asp Tyr Ser His Asp Leu Met Leu Leu Arg
1               5                   10

<210> SEQ ID NO 285
<211> LENGTH: 8
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 285

Cys Gly Leu Gly Ile Asn Ser Arg
1               5

<210> SEQ ID NO 286
<211> LENGTH: 12
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 286

Cys Pro Leu Leu Val Asp Ser Glu Gly Trp Val Lys
1               5                   10

<210> SEQ ID NO 287
<211> LENGTH: 16
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 287

Gly Gly Cys Ile Thr Leu Ile Ser Ser Glu Gly Tyr Val Ser Ser Lys
1               5                   10                  15

<210> SEQ ID NO 288
<211> LENGTH: 18
<212> TYPE: PRT
<213> ORGANISM: Artificial Sequence
<220> FEATURE:
<223> OTHER INFORMATION: synthetic polymeric-immunoglobulin receptor
      tryptic digest peptide
```

```
<400> SEQUENCE: 288

Gly Ser Val Thr Phe His Cys Ala Leu Gly Pro Glu Val Ala Asn Val
1               5                   10                  15

Ala Lys

<210> SEQ ID NO 289
<211> LENGTH: 15
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 289

Gly Val Ala Gly Ser Ser Val Ala Val Leu Cys Pro Tyr Asn Arg
1               5                   10                  15

<210> SEQ ID NO 290
<211> LENGTH: 9
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 290

Ile Ile Glu Gly Glu Pro Asn Leu Lys
1               5

<210> SEQ ID NO 291
<211> LENGTH: 8
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 291

Val Tyr Thr Val Asp Leu Gly Arg
1               5

<210> SEQ ID NO 292
<211> LENGTH: 13
<212> TYPE: PRT
<213> ORGANISM: Artificial Sequence
<220> FEATURE:
<223> OTHER INFORMATION: synthetic 50 kDa protein tryptic digest peptide

<400> SEQUENCE: 292

Glu Val Ala Thr Asn Ser Glu Leu Val Gln Ser Gly Lys
1               5                   10

<210> SEQ ID NO 293
<211> LENGTH: 7
<212> TYPE: PRT
<213> ORGANISM: Artificial Sequence
<220> FEATURE:
<223> OTHER INFORMATION: synthetic 50 kDa protein tryptic digest peptide

<400> SEQUENCE: 293

Leu Ala Ser Tyr Leu Asp Lys
1               5

<210> SEQ ID NO 294
<211> LENGTH: 9
<212> TYPE: PRT
```

<213> ORGANISM: Artificial Sequence
<220> FEATURE:
<223> OTHER INFORMATION: synthetic 50 kDa protein tryptic digest peptide

<400> SEQUENCE: 294

Leu Ala Ser Tyr Leu Asp Lys Val Arg
1               5

<210> SEQ ID NO 295
<211> LENGTH: 9
<212> TYPE: PRT
<213> ORGANISM: Artificial Sequence
<220> FEATURE:
<223> OTHER INFORMATION: synthetic 50 kDa protein tryptic digest peptide

<400> SEQUENCE: 295

Val Leu Asp Glu Leu Thr Leu Ala Arg
1               5

<210> SEQ ID NO 296
<211> LENGTH: 16
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 296

Gln Ser Ser Gly Glu Asn Cys Asp Val Val Val Asn Thr Leu Gly Lys
1               5                   10                  15

<210> SEQ ID NO 297
<211> LENGTH: 9
<212> TYPE: PRT
<213> ORGANISM: Artificial Sequence
<220> FEATURE:
<223> OTHER INFORMATION: synthetic polymeric-immunoglobulin receptor
      tryptic digest peptide

<400> SEQUENCE: 297

Thr Val Thr Ile Asn Cys Pro Phe Lys
1               5

<210> SEQ ID NO 298
<211> LENGTH: 15
<212> TYPE: PRT
<213> ORGANISM: Artificial Sequence
<220> FEATURE:
<223> OTHER INFORMATION: synthetic 50 kDa protein tryptic digest peptide

<400> SEQUENCE: 298

Gly Ser Cys Gly Ile Gly Gly Gly Ile Gly Gly Gly Ser Ser Arg
1               5                   10                  15

<210> SEQ ID NO 299
<211> LENGTH: 11
<212> TYPE: PRT
<213> ORGANISM: Artificial Sequence
<220> FEATURE:
<223> OTHER INFORMATION: synthetic 50 kDa protein tryptic digest peptide

<400> SEQUENCE: 299

Ile Ser Ser Val Leu Ala Gly Gly Ser Cys Arg
1               5                   10

<210> SEQ ID NO 300
<211> LENGTH: 9

-continued

```
<212> TYPE: PRT
<213> ORGANISM: Artificial Sequence
<220> FEATURE:
<223> OTHER INFORMATION: synthetic 83 kDa protein and 169 kDa protein
      tryptic digest peptide

<400> SEQUENCE: 300

Ile Asn Leu Gly Phe Ser Asn Leu Lys
1               5

<210> SEQ ID NO 301
<211> LENGTH: 7
<212> TYPE: PRT
<213> ORGANISM: Artificial Sequence
<220> FEATURE:
<223> OTHER INFORMATION: synthetic 169 kDa protein tryptic digest
      peptide

<400> SEQUENCE: 301

Phe Pro Ser Val Tyr Leu Arg
1               5

<210> SEQ ID NO 302
<211> LENGTH: 16
<212> TYPE: PRT
<213> ORGANISM: Artificial Sequence
<220> FEATURE:
<223> OTHER INFORMATION: synthetic catalase (CAT) tryptic digest peptide

<400> SEQUENCE: 302

Asp Phe Pro Pro Ile Leu Phe Pro Ser Phe Ile His His Ser Gln Lys
1               5                  10                  15

<210> SEQ ID NO 303
<211> LENGTH: 14
<212> TYPE: PRT
<213> ORGANISM: Artificial Sequence
<220> FEATURE:
<223> OTHER INFORMATION: synthetic hypothetical protein tryptic digest
      peptide

<400> SEQUENCE: 303

Phe Gly Gln Gly Ser Gly Pro Ile Val Leu Asp Asp Val Arg
1               5                  10

<210> SEQ ID NO 304
<211> LENGTH: 11
<212> TYPE: PRT
<213> ORGANISM: Artificial Sequence
<220> FEATURE:
<223> OTHER INFORMATION: synthetic Rho GDP-dissociation inhibitor 2
      (ARHGDIB) tryptic digest peptide

<400> SEQUENCE: 304

Thr Leu Leu Gly Asp Gly Pro Trp Thr Asp Pro
1               5                  10

<210> SEQ ID NO 305
<211> LENGTH: 10
<212> TYPE: PRT
<213> ORGANISM: Artificial Sequence
<220> FEATURE:
<223> OTHER INFORMATION: synthetic apolipoprotein A-1 tryptic digest
      peptide

<400> SEQUENCE: 305

Ala Thr Glu His Leu Ser Thr Ser Glu Lys
1               5                  10
```

US 9,157,126 B2

SALIVARY PROTEIN BIOMARKERS FOR HUMAN ORAL CANCER

CROSS-REFERENCES TO RELATED APPLICATIONS

This Application is a continuation of U.S. patent application Ser. No. 12/739,703, filed Aug. 24, 2010, now allowed, which is the U.S. National Phase Application filed under 35 U.S.C. §371 claiming benefit to International Patent Application No. PCT/US08/081,378 filed on Oct. 27, 2008, which is entitled to priority under 35 U.S.C. §119(e) to U.S. Provisional Patent Application No. 60/983,115 filed Oct. 26, 2007 and U.S. Provisional Patent Application No. 61/084,343 filed Jul. 29, 2008, all of which applications are incorporated herein by reference in their entireties.

STATEMENT AS TO RIGHTS TO INVENTIONS MADE UNDER FEDERALLY SPONSORED RESEARCH OR DEVELOPMENT

This invention was made with Government support under Grant No. DE 015970 awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Oral cancer, predominantly oral squamous cell carcinoma (OSCC), is a high impact disease in the oral cavity, affecting more than 34,000 people in the United States each year (American Cancer Society, 2007). Oral cancer is one of the cancers with the worst prognosis, with a 5-year survival rate of 40-50% (Greenlee, R. T. et al., *CA Cancer J Clin*, 50:7-33 (2000); Parkin, D. M. et al., *CA Cancer J Clin*, 55:74-108 (2005)). OSCC tumors arise through a series of molecular mutations that lead to uncontrolled cellular growth from hyperplasia to dysplasia to carcinoma in situ followed by invasive carcinoma. Major risk factors for OSCC include tobacco and alcohol consumption along with environmental and genetics factors (Brinkman, B. M. N. and Wong, D. T., *Curr Opin Oncol*, 18:228-233 (2006); Figuerido, M. L. et al., *Drug Discov Today: Dis Mechan*, 1:273-281 (2004); Hu, S. et al., *Arthritis Rheum.*, 56:3588-600 (2007); Turhani, D. et al., *Electrophor*, 27:1417-1423 (2006)). OSCC is usually detected at late stages when the cancer has advanced and therefore results in poor prognosis and survival. Every individual has a unique prognosis due to the aggressiveness of their tumors therefore they do not behave similarly under the TNM staging system, which classifies tumors by size, lymph node metastasis and distant metastasis. Presently, surgery and radiotherapy are the primary treatments, but due to OSCC's location in the head and neck; this usually results in postoperative defects and functional impairments in patients (Thomson, P. J. and Wylie, J., *Int J Oral Maxillofac Surg*, 31:145-153 (2002)). Therefore, early disease detection is imperative because it can result in a more effective treatment with superior results.

Squamous cell carcinoma (SCC) of the oral cavity and oropharynx is the 6th most common cancer, with approximately 350,000 new cases worldwide annually. The overall 5-year survival rates for oral squamous cell carcinoma (OSCC) have remained low at approximately 30-40% for the past decades. Delayed detection is one of the main reasons for the high morbidity rate of oral cancer, suggesting an imperative need for developing biomarkers to improve early detection of oral cancers. Proteomic analysis of body fluids (e.g., saliva and serum) over the course of oral cancer progression holds promise to identify early detection biomarkers for human oral cancer.

Biomarkers are measurable biological and physiological parameters that can serve as indices for health-related assessments. Protein biomarkers are particularly powerful because they are amenable to simple blood or saliva tests and, once successfully developed, can benefit the cancer patients as simple clinical tools. In terms of identifying protein markers for cancer detection, a body fluid approach (e.g., saliva or blood) appears to be very attractive because it is easy to collect and process these body fluids as compared to tissue biopsies.

Saliva has gained notable attention as a diagnostic fluid because of its simple collection and processing, minimal invasiveness and low costs. Many researchers have studied salivary proteins as potential diagnostic markers for various diseases such as breast cancer, ovarian cancer, Sjögrens syndrome, hepatocellular carcinoma, leukoplakia and oral cancer (Ryu, O. H. et al., *Rheumatol*, 45:1077-1086 (2006); Streckfus, D. et al., *Cancer Invest*, 18:101-109 (2000); Rhodus, N. L. et al., *Cancer Detect Prev*, 29:42-45 (2005); Brailo, V. et al., *Oral Oncol*, 42(4):370-373 (2006); Yio, X. et al., *Ann Clin Biochem*, 29:519-522 (1992); Gorelik, E. et al., *Cancer Epidemiol Biomarkers Prev*, 14:981-987 (2005); Hu, S. et al., *Arthritis Rheum.*, 56:3588-600 (2007)). These potential disease markers, if successfully developed, can lead to simple clinical tools for early detection and the monitoring of disease prognosis and treatment in saliva, a non-invasive body fluid (Kingsmore, S. F., *Nat Rev Drug Discov*, 5:310-321 (2006)).

Currently there are no reliable saliva biomarkers in the clinic for OSCC, however, some recent studies have suggested signature proteins in saliva from OSCC patients can be used for the disease detection. For instance, salivary proteins such as TNF-alpha, interleukin-1 (IL-1), IL-6, IL-8, CD44, fibronectin, defensin-1, cytokeratin 19 fragment (CYFRA 21-1), tissue polypeptide antigen, and cancer antigen CA125, were found overexpressed in OSCC patients (Mizukawa, N. et al., *Oral Dis*, 5(2):139-142 (1999); Franzmann, E. J. et al., *Cancer Epidemiol Biomarkers Prev*, 14(3):735-739 (2005); Rhodus, L. et al., *Cancer Detect Prev*, 29(1):42-45 (2005); Lyons, A. J. and Cui, N., *J Oral Path Med*, 29(6):267-270 (2000); Nagler, R. et al., *Clin Cancer Res*, 12(13):3979-3984 (2006); St. John, M. I. et al., *Arch Otolaryngol Head Neck Surg*, 130:929-935 (2004); Rhodus, N. L. et al., *Cancer Detect Prev*, 29(1):42-5 (2005); Brailo, V. et al., *Oral Oncol*, 42:370-373 (2006)). These proteins, if successfully validated in a large patient cohort, could be potentially useful for OSCC detection.

Analysis of the proteomic content in human saliva is important because it will not only contribute to understanding of oral health and disease pathogenesis but also form a foundation for the discovery of saliva protein biomarkers for human disease detection. Mass spectrometry (MS)-based proteomics has been successfully applied to identification of proteins and their PTMs in human whole and ductal saliva (Wilmarth, P. A. et al., *J. Proteome Res.*, 3(5):1017-1023 (2004); Hu, S. et al., *Proteomics*, 5(6):1714-1728 (2005); Xie, H. et al., *Mol. Cell. Proteomics*, 4(11):1826-1830 (2005); Yates, J. R. et al., *Anal. Chem.*, 78(2):493-500 (2006); Guo, T. et al., *J. Proteome Res.*, 5(6):1469-1478 (2006); Hu, S. et al., *Ann. N.Y. Acad. Sci*, 1098:323-329 (2007)). Many of these studies were performed using shotgun proteomics, which is based on multidimensional separation, tandem MS (MS/MS) and database searching algorithms. Shotgun proteome analysis is very efficient in cataloguing and profiling of proteins, whereas 2-D gel electrophoresis coupled with MS (2-DE/MS) allows mapping out the proteome at protein level and visualization of protein modifications and isoforms (Hirtz, C. et al., *Proteomics*, 5(17):4597-4607 (2005); Walz, A. et al., *Proteomics*, 6(5):1631-1639 (2006)).

Profiling of salivary glycoproteins and proteins in distinct families has been demonstrated lately. The selective enrichment of glycoproteins followed by liquid chromatography-tandem MS (LC-MS/MS) profiling may appear to be a promising approach for finding biomarker and therapeutic targets in cancers (Ramachandran, P. et al., *J. Proteome Res.*, 5(6): 1493-1503 (2006)). Analysis and characterization of cystatins, histatins, proline-rich proteins and their fragments in saliva provides further insight in assessment of their functions in the oral cavity (Inzitari, R. et al., *Proteomics*, 6(23):6370-6379 (2006); Inzitari, R. et al., *Proteomics*, 5(3):805-815 (2005); Messana, I. et al., *J. Proteome Res.*, 3(4):792-800 (2004); Castagnola, M. et al., *J. Biol. Chem.*, 279(40):41436-41443 (2004); Lupi, A. et al., *Proteomics*, 3(4):461-467 (2003)). In addition, a salivary proteome database (http://www.hspp.ucla.edu) has been established to centralize the acquired proteomic data and annotate the identified saliva proteins. These databases are fully accessible to the public for query of the identified proteins, which are linked to public protein databases. With the data deposited and centralized, the processes of integrating large-scale datasets from a variety of laboratories and conducting comparative analysis of saliva proteome to other body fluid proteomes can now begin.

Early diagnosis of oral cancers is imperative, as successful treatment of these cancers often depends on early detection. Considering that approximately 10% of the general population have oral mucosal abnormalities, and that precancerous and early cancerous lesions rarely demonstrate distinct clinical characteristics, there is a growing realization that some premalignant and early cancerous lesions are not readily detectable by visual inspection. Therefore, the integration of early detection and screening based on protein biomarkers, in conjunction with a conventional oral examination, is extremely important. This clearly requires comparative proteome analysis of oral pre-cancer and cancer samples in order to achieve protein markers for truly early detection of OSCC.

The present invention fulfills a need in the art for both salivary oral cancer protein biomarkers and practical methods of detecting these saliva-based biomarkers. The present invention provides saliva-based diagnostic biomarkers of oral squamous cell carcinoma (OSCC) and periodontal disease. The present invention also provides methods of diagnosing and distinguishing both periodontal disease and OSCC.

BRIEF SUMMARY OF THE INVENTION

In a first embodiment, the present invention provides novel salivary oral squamous cell carcinoma (OSCC) biomarkers that are useful in the diagnosis or prognosis of an oral disease, such as oral cancer or periodontal disease. In one embodiment, these biomarkers include IL-6, IL-8, TNF-α, IL-1β, and those found in one of Tables 1, 4, 5, or 6.

In a second embodiment, the present invention provides methods of determining the expression level of salivary biomarkers. In certain embodiments, the methods comprise the detection of disease biomarkers in saliva. In particular embodiments, the disease biomarkers are differentially expressed in the saliva of patients suffering from an oral disease, a cancer, a genetic disease, or a systemic disease. In specific embodiments, the biomarkers comprise proteins or mRNAs that are differentially expressed in the saliva of patients suffering from OSCC, an oral cancer, or periodontal disease.

In a third embodiment, the methods of the present invention comprise the use of multiplex assays for the detection of biomarkers in saliva. In certain embodiments, the multiplex assays are bead-based assays, such as xMAP or xTAG Luminex assays. In a particular embodiment, the method comprises the detection of at least one OSCC biomarker selected from IL-6, IL-8, TNF-α, IL-1β, and those found in Table 1.

In a forth embodiment, the present invention provides novel methods of diagnosis or for providing a prognosis for an oral disease, such as oral cancer or periodontal disease. In certain embodiments, the methods of the invention comprise the detection of an OSCC biomarker. In particular embodiments, these biomarkers include IL-6, IL-8, TNF-α, IL-1β, and those found in Table 1. In a specific embodiment, the methods comprise the use of a multiplex bead-based assay.

In a fifth embodiment, the present invention provides a method of differentiating between oral cancer and periodontal disease. In certain embodiments, these methods comprise determining the level of one or more oral cancer biomarkers. In particular embodiments, these methods comprise comparing an oral cancer expression profile from an individual to at least a first reference oral cancer expression profile.

In a sixth embodiment, the present invention provides kits useful in the detection of salivary biomarkers. In some embodiments, the kits provided by the invention will find use in the diagnosis or for providing a prognosis for an oral disease, such as oral cancer or periodontal disease. In certain embodiments, the kits of the invention may comprise an OSCC biomarker. In other embodiments, the kits of the invention may comprise a detection reagent that specifically binds to a salivay biomarker. In a specific embodiment, the kits of the invention may comprise a reagent that specifically binds to an OSCC biomarker selected from IL-6, IL-8, TNF-α, IL-1β, and those found in Tables 1, 4, 5, and 6.

BRIEF DESCRIPTION OF THE DRAWINGS

FIG. 5. Comparison of single-plex (A) and multiplex (B) assays for the measurement of IL-1β in the saliva of OSSC versus control subjects. For the single-plex assay (A), the average levels of IL-1β are 945.2 pg/ml in OSCCs (n=20) and 314.2 pg/ml in controls (n=20). For the multiplex assay (B), the average levels of IL-1β are 1013.5 pg/ml in OSCCs (n=20) and 376.3 pg/ml in controls (n=20).

FIG. 6. Comparison of single-plex (A) and multiplex (B) assays for the measurement of IL-8 in the saliva of OSSC versus control subjects. For the single-plex assay (A), the average levels for OSCCs (n=20) and controls (n=20) are 3313.2 and 1061.7 pg/ml, respectively. For the multiplex assay (B), the average levels for OSCCs (n=20) and controls (n=20) are 2834.9 and 947.3 pg/ml, respectively.

FIG. 9, comprising FIGS. 9A-9N, (Table 4) provides oral cancer biomarkers that are overexpressed in the saliva of individuals suffering from oral cancer as compared to individuals not suffering from oral cancer.

FIG. 10, comprising FIGS. 10A-10H, (Table 5) provides oral cancer biomarkers that are overexpressed in the saliva of individuals not suffering from oral cancer as compared to individuals suffering from oral cancer.

FIG. 11, comprising FIGS. 11A-11BB, (Table 6) provides oral cancer biomarkers that are differentially expressed in the saliva of individuals suffering from oral cancer as compared to individuals not suffering from oral cancer.

FIG. 12. Table 7 provides validation for several salivary oral cancer biomarkers.

DETAILED DESCRIPTION OF THE INVENTION

Figure 1:
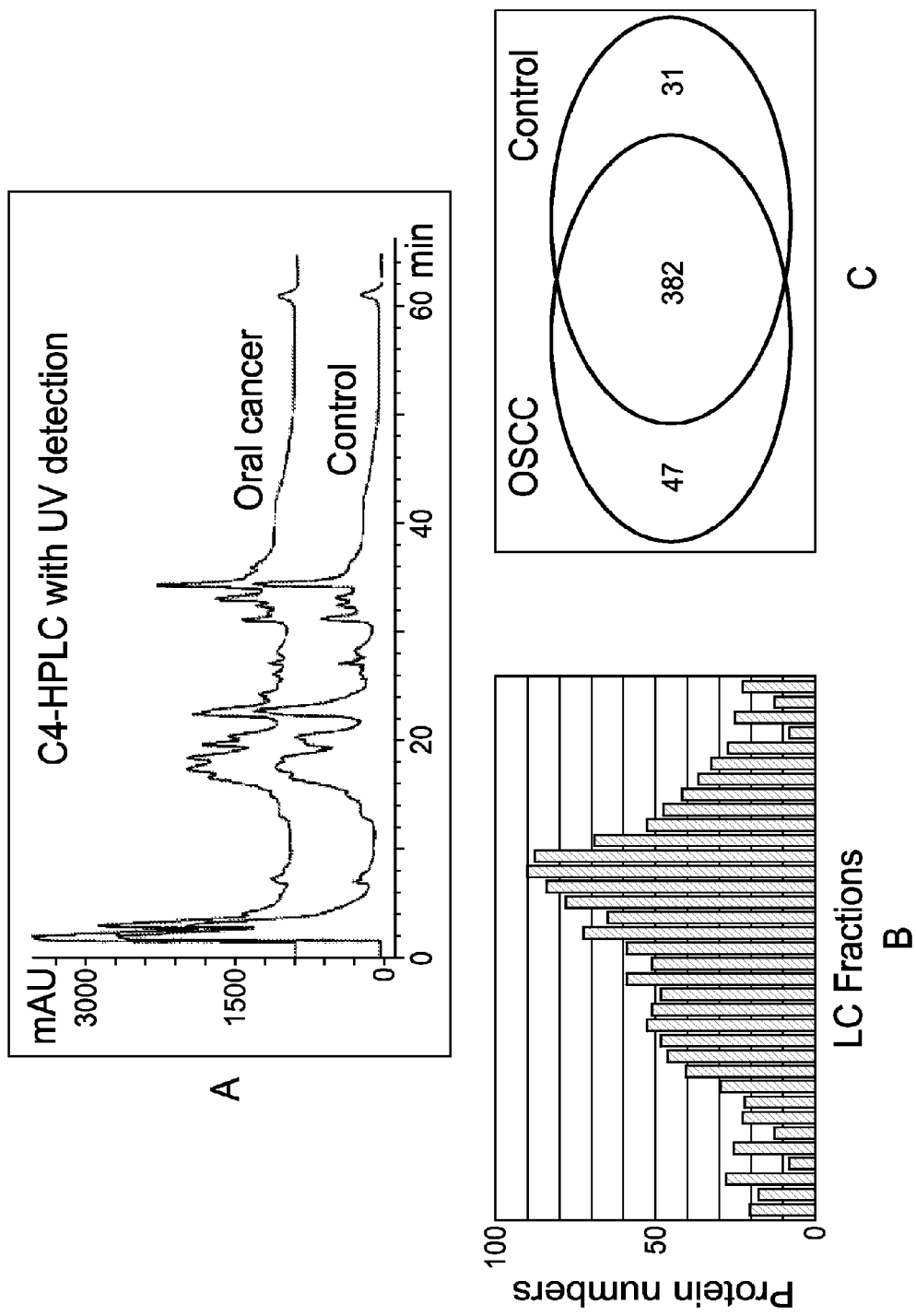
FIG. 1. Shotgun proteome analysis of the pooled oral fluid samples from 16 OSCC or 16 matched control subjects. C4 RP-LC separation of intact proteins in pooled saliva from 16 OSCCs or 16 matched control subjects is shown in FIG. 1A. The number of proteins identified in pooled saliva sample from 16 OSCC subjects is shown in FIG. 1B. In total, 429 proteins were identified from the pooled cancer sample whereas 413 proteins were identified from the pooled control sample (FIG. 1C).

The present invention relates to the identification of novel salivary oral squamous cell carcinoma (OSCC) biomarkers and novel methods of using such for diagnosing or providing a prognosis for an oral disease, such as oral cancer or periodontal disease. The present invention also provides kits useful in the practice of the methods of the invention. In certain embodiments, these kits comprise detection reagents that specifically bind the biomarkers of the present invention As demonstrated herein, saliva proteomics is a promising approach to the discovery of markers for the diagnosis and prognosis of human cancers, especially oral cancer. Saliva is a very attractive diagnostic fluid because its collection is non-invasive. For patients, the non-invasive collection procedures for saliva dramatically reduces anxiety and discomfort and simplifies procurement of repeated samples for monitoring over time. Patient-based saliva proteome analysis is a promising approach to biomarker discovery because of simple sample collection and processing.

Until now, improving the coverage for salivary proteome analysis was challenging. The present invention demonstrates that subtractive proteomics based on direct shotgun profiling is a practical method for the discovery of novel proteomic biomarkers. Through extensive validation using immunoassays, the present invention provides novel saliva protein biomarkers that are useful for improved diagnosis and prognosis of oral cancer or periodontal disease, with both high sensitivity and specificity.

With the development of new quantitative proteomics tools, including those provided by the present invention, it is anticipated that future applications of salivary proteomics, including discovery of disease biomarkers for early diagnosis, prognosis, and monitoring the relapse of cancer, identification of biomarkers for assessment of drug efficacy and toxicity, classification of disease subgroups, and prediction of treatment responses of individual patients, will be improved. These applications may eventually lead to simple clinical assays for early detection of OSCC, which will help improve the management of oral cancer patients.

The present invention provides patient-based oral cancer proteomics studies that have led to the discovery of candidate salivary and scrum biomarkers for OSCC detection. In example 1, the invention provides a proteomic study of salivary protein biomarkers, which utilizes subtractive proteomic approaches based on C4 HPLC prefractionation and LC-QqTOF MS. These methods have identified oral cancer biomarkers that are differentially expressed in whole saliva samples from 16 OSCC patients, as compared to salivary samples from 16 matched control subjects. Many of the identified putative biomarkers of OSCC are regulatory proteins or glycoproteins, including Myc binding protein 2, angiomotin like 2, Ras-related protein Rab-7, Mac-2-binding protein (M2BP), Rho GDP-dissociation idubitor 2, CD59 glycoprotein precursor, involucrin, KRAB box family protein, hematopoietic lineage cell specific protein, peroxisome biogenesis factor 1, nuclear mitotic apparatus protein 1, swiprosin-2, PHD finger protein 3, histone H1.2, histone H1.3 and calgranulin A.

In one embodiment, the present invention provides novel OSCC salivary biomarkers that have been identified through patient-based proteomic studies of salivary proteins differentially expressed in patients suffering from oral cancer. In one embodiment, oral cancer biomarkers were found at higher levels in the saliva of oral cancer patients as compared to the levels in matched healthy subjects, for example, those found in Table 4. Further validation by immunoassays indicated that a panel of discovered biomarkers, including M2BP, calgranulin B, CD59, profiling, and catalase, are significantly overexpressed in oral cancer patients. These five protein biomarkers collectively provide a sensitivity of 91.7% and a specificity of 87.0% for OSCC diagnosis. The present invention demonstrates that patient-based saliva proteome analysis is a promising approach to cancer biomarker discovery. The novel biomarkers provided by the present invention may help improve the clinical diagnosis and prognosis of OSCC. In another embodiment, the present invention provides biomarkers that underexpressed in the saliva of individuals suffering from oral cancer as compared to the saliva of individuals not suffering from oral cancer, such as those biomarkers found in Table 5. In yet another embodiment, the present invention provides oral cancer biomarkers that are differentially expressed in the saliva of individuals suffering from oral cancer as compared to the saliva of individuals not suffering from oral cancer, such as those found in Table 6.

The invention further provides ELISA-based validation for the differential expression of M2BP (n=32 for each group, p=0.000006) and calgranulin A (n=20 for each group), with the use of secondary OSCC and control subject cohorts.

In another embodiment, the invention provides scrum oral cancer biomarkers, which were identified from 10 oral cancer and 10 control subjects using 2-D gel electrophoresis. The proteins at significantly differential levels were identified using in-gel digestion followed by LC-QqTOF MS analysis of the resulting peptides. The discovered candidate biomarkers include calgranulin A, serum amyloid A-4 protein and related isoforms, haptoglobin-related protein, focolin 2, alpha-1-antitrypsin, complement C3 (fragment), splice isoform 1 of complement factor H-related protein 2 (up-regulated) and transthyretin, tetranectin, telomerase regulation-associated protein, alpha-1-acid glycoprotein 1 and 2, Apolipoprotein E, RalA binding protein 1 (down-regulated). Further validation of calgranulin A by ELISA (n=20 for each group, p=0.039) and tetranectin by immunoblotting (n=35 for each group) was also demonstrated. The present invention demonstrates that patient-based saliva and serum proteome analysis is a very promising approach to discovery of biomarkers for cancer diagnosis and prognosis. These promising candidate biomarkers may be used to improve the clinical detection of OSCC.

In one embodiment, the present invention provides novel salivary oral squamous cell carcinoma (OSCC) biomarkers that are useful in the diagnosis or prognosis of an oral disease, such as oral cancer or periodontal disease. In certain embodiments, these biomarkers comprise proteins that are differentially expressed in an individual suffering from an oral disease, such as oral cancer or periodontal disease, as compared to an individual not suffering from an oral disease. The salivary biomarkers of the present invention may identified through the use of subtractive mass spectrometry, wherein the protein levels found in a salivary sample from an individual suffering from an oral disease are compared to the protein levels found in a salivary sample from an individual not suffering from an oral disease. In a specific embodiment, these biomarkers comprise IL-6, IL-8, TNF-α, IL-1β, and those found in Tables 1, 4, 5, and 6.

In another embodiment, the present invention provides methods of determining the expression level of salivary biomarkers. In certain embodiments, the methods comprise the detection of disease biomarkers in saliva. In particular embodiments, the disease biomarkers are differentially expressed in the saliva of individuals suffering from an oral disease, a cancer, a genetic disease, or a systemic disease, as compared to the saliva of an individual not suffering from said disease state. In one embodiment, the invention provides methods of detecting a biomarker that is differentially expressed in the saliva of a patient suffering from OSCC, an oral cancer, or periodontal disease.

In one embodiment, the present invention provides methods of detecting biomarkers expressed in saliva. In certain embodiments, these biomarkers include without limitation, genes found in the SECT (Hu et al, Clin Chem 54(5):824-32 (2008)), cytokines, IL-1β (M15330), IL-8 (NM_000584), IL-1α (M15329), IL-2 (NM_000586), IL-3 (NM_000588), IL-4 (BC070123), IL-5 (NM_000879), IL-6 (NM_000600), IL-10 (NM_000572), NF-κB dependent cytokines, a GM-CSF, VEGF (NM_001025366), Rho GDP-dissociation inhibitor 2 (ARHGDIB; NM_001175), Nuclear mitotic apparatus protein 1 (NUMA1; NM_006185), CD59 glycoprotein (NM_000611), Myc binding protein 2 (MYCBP2; NM_015057), Involucrin (IVL; NM_005547), KRAB box family protein (ZNF577; NM_032679), Ras-related protein Rab-7 (RAB7A; NM_004637), Pyruvate dehydrogenase complex E2 subunit (DLAT; NM_001931), Neuroblast differentiation associated protein AHNAK (NM_001620), Development and differentiation enhancing factor 2 (ASAP2; NM_001135191), Splice isoform of citron Rho-interacting kinase (CIT; NM_007174), Mac-2 binding protein (LGALS3BP; M2BP; NM_005567), SH3 domain-binding glutamic acid-rich-like protein (SH3BGRL; NM_003022), Glial fibrillary acidic protein (GFAP; NM_002055), Hematopoietic lineage cell specific protein (HCLS1; NM_005335), SERPINB8 (NM_001031848), Angiomotin like 2 (AMOTL2; NM_016201), HEJ1 (AF395440), Swiprosin-2 (EFHD2; NM_024329), PHD finger protein 3 (PHF3; NM_015153), Leucine-rich repeat kinase 2 (LRRK2; NM_198578), Histone H1.2 (HIST1H1C; NM_005319), Catalase (CAT; NM_001752), IPI00178083 29 kDa protein (TPM3; NM_153649), Histone H1.3 (HIST1H1D; NM_005320), Epsilon globin (HBE1; NM_005330), MRDS1 protein (OFCC1; NM_153003), Calgranulin (S100A12; NM_005621), Acyl-CoA-binding protein (DBT; NM_020548), Moesin (MSN; NM_002444), MRP14 (calganulin B) (S100A9; NM_002965), Thymosin beta-4 (TMSB4X; NM_021109), Similar to POTE2A protein (LOC653269; XM_928585), Vitamin D-binding protein (GC; NM_000583), Brain acid soluble protein 1 (BASP1; NM_006317), IPI00334.432 16 kDa protein (HBA1; NM_000558), IPI00334610 41 kDa protein (ACTB; NM_001101), Prothymosin alpha (L21695), IPI00376164 5 kDa protein (TMSL2; NM_182793), Thymosin-like 4 (CAI13489), Amyloid beta (APBB1IP; NM_019043), Profilin (PFN1; NM_005022), Peroxisome biogenesis factor (PEX1; NM_000466), IPI00412365 43 kDa protein ( ), Vimentin (VIM; NM_003380), TRIM9 (TRIM67; NM_001004342), and IPI00479902 57 kDa protein (keratin 10; NP_000412). Other suitable biomarkers include genes differentially expressed in the saliva of patients suffering from an oral disease, such as periodontal disease, a cancer, such as OSCC, a genetic disease, a systemic disease, or the like.

In certain embodiment, the methods of the present invention comprise the use of multiplex assays for the detection of biomarkers in saliva. In particular embodiments, the multiplex assays are bead-based assays. Multiplex bead-based formats well suited for use in the present invention include without limitation, xMAP and xTAG (Luminex), LiquiChip (Qiagen), QuantiGene Plex (Panomics), Beadlyte (Millipore), and the like. In certain embodiments, the method comprises the detection of at least one OSCC biomarker selected from IL-6, IL-8, TNF-α, IL-1β, and those found in Tables 1, 4, 5, and 6.

In certain embodiments, the present invention provides methods of detecting at least two biomarkers in a single assay. In other embodiments, the methods comprise detecting at least about 3, 4, 5, 6, 7, 8, 9, 10, 15, 20, 25, 30, 40, 50, 75, 100, 200, 300, 400, 500 or more biomarkers in a single assay. In yet other embodiments, the biomarkers comprise a disease transcriptome, or a subset of a disease transcriptome suitable for diagnosis or prognosis of said disease. Diseases transcriptomes well suited for use in the present invention include without limitation, oral disease transcriptomes, cancer transcriptomes, genetic disease transcriptomes, systemic disease transcriptomes, an OSCC transcriptome, a periodontal disease transcriptome, and the like.

In another embodiment, the present invention provides novel methods of diagnosing or for providing a prognosis for a disease. In certain embodiments, the methods of the invention comprise the detection of an OSCC biomarker for the diagnosis or prognosis of an oral disease, such as oral cancer or periodontal disease. In particular embodiments, these biomarkers include IL-6, IL-8, TNF-α, IL-1β, and those found in Tables 1, 4, 5, and 6. In a specific embodiment, the methods comprise the use of a multiplex bead-based assay.

The methods of the present invention are particularly well suited for diagnosing and providing a prognosis for oral diseases, cancers, systemic diseases, and genetically predisposed diseases. "Oral Disease" refers to diseases of the mouth, gums, throat, neck, lips, etc., including without limitation, oral cancers, aggressive, chronic, or necrotizing periodontal disease, gingivitis, gum disease, mouth, throat, or tongue ulcers, angular cheilitis, oral lichen planus, and the like.

Many "genetically predisposed diseases" or "genetic diseases" are known in the art. These diseases include those caused by a genetic mutation, insertion, deletion, chromosomal abnormality, and the like The diseases may be autosomal, sex chromosome linked, or epigenetic and include any disease which has a genetic component or for which a genetic component may provide a risk of developing. Examples of genetic diseases or genetically predisposed diseases embraced by the present invention include, without limitation, Acid Maltase Deficiency, Cystic Fibrosis, Fanconi Anemia, Hemochromatosis, Hemophilia, Hypophosphatasia, Klinefelter Syndrome, Leukodystrophy, Marfan Syndrome, Neurofibromatosis, Prader-Willi Syndrome, Sickle Cell Disease, Tuberous Sclerosis, Turner's Syndrome, von Hippel-Lindau Disease, Type I and Type II Diabetes, Cancer, Heart Disease, Crohn's Disease, Periodontal disease, Cancer, and the like.

As used herein, a "systemic disease" is a disease that affects a plurality of organs and tissues, or affects the body as a whole. Many systemic diseases are known in the art and include, without limitation, Systemic vasculitis e.g., SLE, PAN, Sarcoidosis, Diabetes, Hypertension, Metabolic syndrome, AIDS, and the like. One of skill in the art will know of other diseases that are well suited for the methods of the present invention.

In a particular embodiment, the present invention provides a method of diagnosing or providing a prognosis for a disease in an individual, the method comprising the steps of: (a) contacting a salivary biological sample from an individual with a reagent that specifically binds to a biomarker; and (b) determining whether or not said biomarkers is differentially expressed in the sample, thereby diagnosing or providing a prognosis for said disease. In particular embodiments, the disease is a cancer, an oral cancer, an oral disease, a genetic disease, or a systemic disease. In a specific embodiment, the disease is oral cancer or periodontal disease. In one embodiment, an oral biomarkers is a proteins or nucleic acids that is differentially expressed in the saliva of a patient suffering from oral cancer or periodontal disease. In a particular embodiment, a biomarkers may be IL-8, IL-1β, or a biomarker found in any one of Tables 1, 4, 5, or 6. In yet other embodiments, the biomarkers comprise at least one of IL-1α, IL-2, IL-3, IL-4, IL-5, IL-6, IL-10, NF-κB dependent cytokines, GM-CSF, VEGF, a biomarker found in any one of Tables 1, 4, 5, or 6, a gene found in the SECT, or a gene differentially expressed in the saliva of patients suffering from oral cancer or periodontal disease. In one particular embodiment, the biomarkers comprise an oral cancer transcriptome or subset thereof.

In a particular embodiment, the invention provides a method of diagnosing or providing a prognosis for oral cancer in an individual, the method comprising the steps of: (a) contacting a biological sample from an individual with a reagent that specifically binds an oral cancer biomarker selected from those found in Table 1; and (b) determining whether or not said biomarker is differentially expressed in the sample, thereby diagnosing or providing a prognosis for oral cancer. In certain embodiments, the method may comprise the detection of more than one oral cancer biomarker, for example, at least 2, 3, 4, 5, 6, 7, 8, 9, 10, 15, 20, 25, 30, 40, 50, 75, 100 or more oral cancer biomarkers of the invention. In a particular embodiment of the invention, at least one of said biomarkers is selected from the group consisting of M2BP, calgranulin B, CD59, profilin, and catalase. In another particular embodiment, the methods of the invention comprise the detection of M2BP, calgranulin B, CD59, profilin, and catalase. In related embodiments, the methods of the invention may further comprise the detection of a cytokine, or at least one of the group consisting of IL-6, IL-8, TNF-α, IL-1β. In a specific embodiment, the oral cancer is oral squamous cell carcinoma (OSCC).

In certain embodiments, the methods of the present invention will comprise determining whether or not one or more biomarkers are differentially expressed by the steps of (a) determining the level of said one or more biomarkers in a sample from the individual; and (b) comparing said level to at least a first reference level from an individual not suffering from oral cancer.

The biomarkers of the invention may be detected using a number of known techniques in the art, including without limitation, an antibody based assay, ELISA, western blotting, mass spectrometry, microarray, protein microarray, flow cytometry, immunofluorescence, PCR, immunohistochemistry, and a multiplex detection assay. In specific embodiments of the invention, the level of an oral cancer biomarker may be detected using ELISA or a multiplex detection assay, such as a bead-based multiplex detection assay, for example, a Luminex® xMAP detection assay.

Luminex MultiAnalyte Profiling (xMAP) technology, previously known as FlowMetrix and LabMAP (Elshal and McCoy, 2006), is a multiplex bead-based flow cytometric assay that is gaining recognition as a method for analyte quantitation. This technology utilizes 5.6-micron polystyrene beads that are internally dyed with different intensities of red and infrared fluorophores. Currently there are 100 beads, each with a unique spectral make up which allows the mixing of several bead sets and, in theory, enabling the detection of up to 100 different analytes per assay (Vignali, D. A. A., *J Immunol Methods*, 243:243-255 (2000)).

The beads can be bound by various capture reagents such as antibodies, oligonucleotides, and peptides, therefore facilitating the quantification of various proteins, ligands, DNA and RNA (Fulton, R. J. et al., *Clin Chem*, 43:1749-1756 (1997); Kingsmore, S. F., *Nat Rev Drug Discov*, 5:310-321 (2006); Nolan, J. P. and Mandy, F., *Cytometry Part A*, 69A: 318-325 (2006)). The assays are run on a 96-well plate format, followed by detection on a Luminex 100 instrument. As the beads run through the instrument, the internal dyes are excited by a laser which results in the classification of each bead. Another laser excites the reporter dye which is directly proportional to the amount of analyte bound to each bead (Vignali, D. A. A., *J Immunol Methods*, 243:243-255 (2000); Ray, C. A. et al., *J Pharma Biomed Anal*, 36:1037-1044 (2005)).

The resulting fluorescence is recorded by the instrument which then provides the median fluorescence unit obtained from measuring 100 beads. Luminex xMAP technology has many applications including protein expression profiling, gene expression profiling, genotyping, immunodiagnostics, and genetic disease diagnostics.

Although single-plex bead-based assays have been available for a long time; technological developments have enhanced the development of multiplex bead-based assays enabling the utilization of this method for quantitation of a panel of protein markers simultaneously (Linkov, F. et al., *Cancer Epidemiol Biomarkers Prev*, 16:102-107 (2007); Prabhakar, U. et al., *J Immunol Methods*, 260:207-218 (2002)). The advantage of Luminex xMAP technology lies in its high sensitivity, throughput and efficiency (Vignali, D. A. A., *J Immunol Methods*, 243:243-255 (2000); DuPont, N. C. et al., *J Reprod Immunol*, 66:175-191 (2005)). Significant reduction in time and costs results from multiplexing when compared to ELISA. ELISA is more expensive and time-consuming to perform when many proteins are to be measured using many single-plex protein specific assays (de Jager, W. and Rijkers, G. T., *Methods*, 38:294-303 (2006)).

On the contrary, many protein analytes can be measured by the multiplexed bead-based assay with a single plate. This is extremely important for clinical studies where sample volumes are limited (Liu, M. Y. et al., *Clin Chem*, 51:1102-1109

(2005)). Bead-based assay is more accurate because the median fluorescence is obtained from the readout of at least 50 to 100 beads. Thus each bead is functioning as a duplicate, making this assay more reliable (Vignali, D. A. A., *J Immunol Methods*, 243:243-255 (2000); Kettman, J. R. et al., *Cytometry*, 33:234-243 (1998)).

The presumptive disadvantage of xMAP technology is the possible cross-reactivity between antibodies. Sensitivity may also be compromised due to the increasing number of beads per well. In addition, the performance in the multiplex assays can be variable as a result of the multipurpose diluent which may not optimize each analyte to the same extent as in the case with single analyte measurements by ELISA (Carson, R. T. and Vignali, D. A. A., *J Immunol Methods*, 227:41-52 (1999)). Although Luminex multiplex bead-based assay kits have been optimized to measure protein levels in serum and cell lines, the current invention demonstrates that this technique can also be used to measure protein levels, such as interleukin-8 (IL-8) and interleukin-1β (IL-1β, in the saliva of patients suffering from OSCC, periodontal disease, matched healthy control subjects, and the like.

In a particular embodiment, the present invention provides a method of diagnosing or providing a prognosis for a disease in an individual, the method comprising the steps of: (a) contacting a salivary biological sample from said individual with a reagent that specifically binds to more than one protein biomarker; and (b) determining in a multiplex assay whether or not said more than one protein biomarkers are differentially expressed in the sample, thereby diagnosing or providing a prognosis for said disease. In particular embodiments, the disease is a cancer or an oral cancer, an oral disease, periodontal disease, a genetic disease, or a systemic disease. In a specific embodiment, the disease is oral cancer, such as OSCC, or periodontal disease. In one embodiment, the oral biomarkers are proteins or nucleic acids that are differentially expressed in the saliva of patients suffering from oral cancer or periodontal disease. In a particular embodiment, the biomarkers are selected from IL-8, IL-1β, and those found in Tables 1, 4, 5, and 6. In yet other embodiments, the biomarkers further comprise at least one of IL-1α, IL-2, IL-3, IL-4, IL-5, IL-6, IL-10, NF-κB dependent cytokines, GM-CSF, VEGF, a gene found in the SECT, or a gene differentially expressed in the saliva of patients suffering from oral cancer or periodontal disease. In one particular embodiment, the biomarkers comprise an oral cancer transcriptome or subset thereof.

In one embodiment, the invention provides a method of diagnosing or providing a prognosis for oral cancer in an individual, the method comprising the steps of (a) contacting a salivary biological sample from said individual with a reagent that specifically binds to more than one oral cancer biomarker; and (b) determining in a multiplex assay whether or not said more than one oral cancer biomarkers are differentially expressed in the sample, thereby diagnosing or providing a prognosis for oral cancer, wherein said more than one protein biomarkers are selected from the group consisting of TL-6, IL-8, TNF-α, IL-1β, and those found in Tables 1, 4, 5, and 6. In a particular embodiment, said multiplex assay is bead-based.

In another embodiment, the present invention provides methods of differentiating between oral cancer and periodontal disease in an individual. In one embodiment, the method comprises the determination of the level of at least one oral cancer biomarker. In a particular embodiment, the biomarker is selected from IL-8, IL-1β, and those found in Tables 1, 4, 5, and 6. In yet other embodiments, the biomarkers further comprise at least one of IL-1α, IL-2, IL-3, IL-4, IL-5, IL-6, IL-10, NF-κB dependent cytokines, GM-CSF, VEGF, or other genes differentially expressed in the saliva of patients suffering from OSCC or periodontal disease.

In a particular embodiment, the invention provides a method of diagnosing or providing a prognosis for either periodontal disease or oral cancer in an individual, the method comprising the steps of (a) contacting a salivary biological sample from an individual with a reagent that specifically binds to more than one oral cancer biomarker; (b) determining in a multiplex assay the level of expression of said more than one oral cancer biomarker; and (c) classifying the level of expression as either a first, second, or third level; wherein, said first level corresponds to a diagnosis of no periodontal disease or oral cancer, said second level corresponds to a diagnosis of periodontal disease, and said third level corresponds to a diagnosis of oral cancer.

In one embodiment, the invention provides a method of diagnosing or providing a prognosis for oral cancer in an individual, the method comprising the steps of (a) detecting an oral cancer biomarker selected from those found in any one of Tables 1, 4, 5, or 6 in a biological sample from an individual; and (b) determining whether or not said biomarker is differentially expressed in the sample, thereby diagnosing or providing a prognosis for oral cancer.

In another embodiment, the method comprises the steps of (a) comparing the expression profile of at least one biomarker from a patient to the expression profiles from individuals suffering from oral cancer, individuals suffering from periodontal disease, and control individuals, and (b) determining which expression profile best matches the expression profile from said patient, thereby diagnosing the patient as having oral cancer, periodontal disease, or neither.

In a particular embodiment, the step of classifying the level of expression comprises comparing the expression profile of said oral protein biomarkers to at least a first reference expression profile. A reference profile may comprise, for example, the levels of biomarkers in a salivary sample from one or more individuals not suffering from an oral disease, from one or more individuals suffering from oral cancer, or from one or more individuals suffering from periodontal disease.

In certain embodiments, the methods of the invention comprise the detection of an epitope from a biomarker identified by the present invention. In some embodiments, these epitopes include those that are found in the saliva of patients suffering from oral cancer, but not in the saliva of control individuals, such as those found in Table 4. In another embodiment, these epitopes include those that are found in the saliva of control individuals, but not is the saliva of patients suffering from oral cancer, such as those found in Table 5. In yet another embodiment, these epitopes include those that are differentially expressed in the saliva of patients suffering from oral cancer as compared to the saliva of individuals not suffering from oral cancer, such as those found in Tables 1, 4, 5, and 6.

In certain embodiments, the epitopes of the invention may be detected by a method including, without limitation, an antibody based assay, ELISA, western blotting, mass spectrometry, microarray, protein microarray, flow cytometry, immunofluorescence, PCR, immunohistochemistry, and a multiplex detection assay. In a particular embodiment, an epitope of the invention may be detected by mass spectrometry or an immunoassay.

In yet another embodiment, the present invention provides a method of diagnosing or providing a prognosis for oral cancer or periodontal disease, the method comprising the steps of (a) generation a mass spectrometry profile from the saliva of an individual and (b) comparing said mass spectrometry profile to at least a first reference profile corresponding to a diagnosis of no oral cancer. In a second embodiment, the method further comprises comparing said mass spectrometry profile to a second reference profile corresponding to a diagnosis of oral cancer and determining which reference profile best corresponds to the salivary mass spectrometry profile of said individual.

Many correlation methodologies may be employed for the comparison of both individual gene expression levels and multigene expression profiles in the present invention. Non-limiting examples of these correlation methods include parametric and non-parametric methods as well as methodologies based on mutual information and non-linear approaches. Examples of parametric approaches include without limitation, Pearson correlation (or Pearson r, also referred to as linear or product-moment correlation) and cosine correlation. Non-limiting examples of non-parametric methods include Spearman's R (or rank-order) correlation, Kendall's Tau correlation, and the Gamma statistic. Each correlation methodology can be used to determine the level of correlation between the expressions of individual gene sequences in the data set. The correlation of all sequences with all other sequences is most readily considered as a matrix. Using Pearson's correlation as a non-limiting example, the correlation coefficient r in the method is used as the indicator of the level of correlation. When other correlation methods are used, the correlation coefficient analogous to r may be used, along with the recognition of equivalent levels of correlation corresponding to r being at or about 0.25 to being at or about 0.5. The correlation coefficient may be selected as desired to reduce the number of correlated gene sequences to various numbers. In particular embodiments of the invention using r, the selected coefficient value may be of about 0.25 or higher, about 0.3 or higher, about 0.35 or higher, about 0.4 or higher, about 0.45 or higher, or about 0.5 or higher. The selection of a coefficient value means that where expression between gene sequences in the data set is correlated at that value or higher, they are possibly not included in a subset of the invention. Thus in some embodiments, the method comprises excluding or removing (not using for classification) one or more gene sequences that are expressed in correlation, above a desired correlation coefficient, with another gene sequence in the tumor type data set. It is pointed out, however, that there can be situations of gene sequences that are not correlated with any other gene sequences, in which case they are not necessarily removed from use in classification.

In one embodiment, the present invention provides a method of diagnosing or providing a prognosis for periodontal disease in an individual, the method comprising the steps of (a) contacting a salivary biological sample from an individual with a reagent that specifically binds to at least one salivary biomarker; and (b) determining whether or not said at least one biomarker is differentially expressed in the sample, thereby diagnosing or providing a prognosis for periodontal disease.

In another embodiment, the present invention provides kits useful in the detection of salivary biomarkers. In some embodiments, the kits provided by the invention will find use in the diagnosis or for providing a prognosis for an oral disease, such as oral cancer or periodontal disease. In certain embodiments, the kits of the invention may comprise an oral cancer biomarker. In other embodiments, the kits of the invention may comprise a detection reagent that specifically binds to a salivay biomarker. In a specific embodiment, the kits of the invention may comprise a reagent that specifically binds to an oral cancer biomarker selected from IL-6, IL-8, TNF-α, IL-1β, and those found in Tables 1, 4, 5, and 6. In other embodiments, a kit provided by the present invention may be capable of binding to more than one oral cancer biomarker. As such, the kits provided by the present invention are particularly well suited for use in multiplex assays, for example bead-based assays.

In certain embodiments, the kits provided by the present invention comprises a multiplex reagent capable of binding to more than one oral cancer protein biomarker and a substrate for containing said multiplex reagent. In certain embodiments, the multiplex reagent comprise a plurality of beads coupled to detection reagents, such as antibodies, for use in a fluorescent-based assay. Non-limiting examples of suitable technologies include xMAP and xTAG (Luminex), Liqui-Chip (Qiagen), QuantiGene Plex (Panomics), Beadlyte (Millipore), and the like. The kits of the present invention may further comprise a secondary detection reagent, such as fluorescently-labeled antibody, for detection of the biomarkers. The kits of the present invention may further include dilution and wash buffers.

In yet another embodiment, the present invention provides an antibody generated against a salivary oral cancer biomarker. In certain embodiments of the invention, the antibodies are generated against a biomarker selected from those found in any one of Tables 1, 4, 5, or 6. In yet another embodiment, the invention provides an antibody generated against an epitope found in any one of Tables 4, 5, or 6.

DEFINITIONS

Oral cancer biomarkers or OSCC biomarkers recited herein, refer to polypeptides and nucleic acids, e.g., gene, pre-mRNA, mRNA, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 60% nucleotide sequence identity, 65%, 70%, 75%, 80%, 85%, 90%, preferably 91%, 92%, 93%, 94%, 95%, 96%, 97%, 98% or 99% or higher nucleotide sequence identity, preferably over a region of at least about 10, 15, 20, 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

Biomarkers of the invention may be identified by name, e.g., Mac-2 binding protein; gene symbol, e.g., Mac2BP; gene name, e.g. LGALS3BP; IPI accession number, e.g., IPI00023673; Genbank accession number, e.g., NM_005567 or NP_005558; or the like. It is understood that all of these reference the same biomarker and thus are equivalent. IPI accession numbers refer to the international protein index (Kersey et al., *Proteomics,* 4(7):1985-1988 (2004)).

The term "cancer" refers to human cancers and carcinomas, sarcomas, adenocarcinomas, lymphomas, leukemias, solid and lymphoid cancers, etc. Examples of different types of cancer include, but are not limited to, oral squamous cell carcinoma (OSCC), breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), pleural cancer, pancreatic cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, and acute myelocytic leukemia. Cancers embraced in the current application include both metastatic and non-metastatic cancers.

As used herein, "oral cancer" refers to a group of malignant or neoplastic cancers originating in the head or neck of an individual. Non-limiting examples of oral cancers include cancers of the lip, tongue, throat, tonsils, neck, buccal vestibule, hard or soft palate, gums (including gingival and alveolar carcinomas), nasopharyngeal cancer, esophageal cancer, lingual cancer, buccal mucosa carcinoma, head and neck squamous cell carcinoma, and the like.

"Head and neck squamous cell carcinoma" refers to group of cancers of epithelial cell origin originating in the head and neck, including the oral cavity and pharynx. These tumors arise from diverse anatomical locations, including the oral cavity, oropharynx, hypopharynx, larynx, and nasopharynx, but in some cases can have in common an etiological association with tobacco and/or alcohol exposure. The oral cavity is defined as the area extending from the vermilion border of the lips to a plane between the junction of the hard and soft palate superiorly and the circumvallate papillae of the tongue inferiorly. This region includes the buccal mucosa, upper and lower alveolar ridges, floor of the mouth, retromolar trigone, hard palate, and anterior two thirds of the tongue. The lips are the most common site of malignancy in the oral cavity and account for 12% of all head and neck cancers, excluding nonmelanoma skin cancers. Squamous cell carcinoma is the most common histologic type, with 98% involving the lower lip. Next most common sites in order of frequency are the tongue, floor of the mouth, mandibular gingiva, buccal mucosa, hard palate, and maxillary gingiva. The pharynx consists of the oropharynx, nasopharynx, and hypopharynx. The most common sites of cancer in the oropharynx are the tonsillar fossa, soft palate, and base of tongue, followed by the pharyngeal wall. The hypopharynx is divided into the pyriform sinus (most common site of tumor involvement), posterior pharyngeal wall, and postericoid region.

"Periodontal disease" refers to a group of diseases affecting the gums of an individual, including gingivitis, periodontitis, and the like. Periodontal diseases may be further classified as aggressive, chronic, or necrotizing. Periodontitis is generally characterized by inflammation of the periodontium tissues, including the gingiva, the cementum, the alveolar bone, and the periodontal ligaments.

"Therapeutic treatment" and "cancer therapies" refers to chemotherapy, hormonal therapy, radiotherapy, and immunotherapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms,* (vols. 1-3, 1992); Lloyd, *The Art, Science and Technology of Pharmaceutical Compounding* (1999); Pickar, *Dosage Calculations* (1999); and Remington, *The Science and Practice of Pharmacy,* $20^{th}$ ed., Gennaro, Ed., Lippincott, Williams & Wilkins (2003)).

"Metastasis" refers to spread of a cancer from the primary tumor or origin to other tissues and parts of the body, such as the lymph nodes.

"Saliva" refers to any watery discharge from the mouth, nose, or throat. For the purposes of this invention, saliva may include sputum and nasal or post nasal mucous.

"Providing a prognosis" refers to providing a prediction of the likelihood of metastasis, predictions of disease free and overall survival, the probable course and outcome of cancer therapy, or the likelihood of recovery from the cancer, in a subject.

"Diagnosis" refers to identification of a disease state, such as cancer or periodontal disease, in a subject. The methods of diagnosis provided by the present invention can be combined with other methods of diagnosis well known in the art. Non-limiting examples of other methods of diagnosis include, detection of known disease biomarkers in saliva samples, oral radiography, co-axial tomography (CAT) scans, positron emission tomography (PET), radionuclide scanning, oral biopsy, and the like.

The terms "oral cancer biomarker," or "OSCC biomarker," or "periodontal disease biomarker", or "biomarker," interchangeably refer to a gene, mRNA or protein, that is present in a biological sample, e.g. saliva, from a subject with a disease, such as oral cancer, periodontal disease, a systemic disease, or a genetically predisposed disease, at a different level or concentration in comparison to a biological sample from a subject without the disease, and which is useful for the diagnosis of the disease, for providing a prognosis, or for preferential targeting of a pharmacological agent to an affected cell or tissue.

The term "differentially expressed" or "differentially regulated" refers generally to a protein or nucleic acid that is overexpressed (upregulated) or underexpressed (downregulated) in one biological sample compared to at least one other sample, generally in saliva from a subject with cancer or a cancer cell, in comparison to saliva from a subject without cancer or a non-cancer cell, or in saliva from a subject with periodontal disease as compared to the saliva from an individual not suffering from periodontal disease, in the context of the present invention.

The terms "overexpress", "overexpression", "overexpressed", "up-regulate", or "up-regulated" interchangeably refer to a biomarker that is present at a detectably greater level in a biological sample, e.g. saliva or cancer cell, from a patient with cancer, in comparison to a biological sample from a patient without cancer. The term includes overexpression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer. Overexpression can be detected using conventional techniques for detecting mRNA (i.e., RT-PCR, PCR, hybridization) or proteins (i.e., ELISA, immunohistochemical techniques, mass spectroscopy, Luminex® xMAP technology). Overexpression can be 10%, 20%, 30%, 40%, 50%, 60%, 70%, 80%, 90% or more in comparison to a sample from a patient without cancer. In certain instances, overexpression is 1-fold, 2-fold, 3-fold, 4-fold 5, 6, 7, 8, 9, 10, or 15-fold or more higher levels of transcription or translation in comparison to a sample from a patient without cancer.

The terms "underexpress," "underexpression", "underexpressed" or "downregulated" interchangeably refer to a biomarker, usually a protein or nucleic acid, that is present at a detectably lower level in a biological sample, e.g. saliva or cancer cell, in comparison to a biological sample from a subject without cancer. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques, Luminex® xMAP technology). Underexpression can be 10%, 20%, 30%, 40%, 50%, 60%, 70%, 80%, 90% or less in comparison to a sample from a subject without cancer. In certain instances, underexpression is 1-fold, 2-fold, 3-fold, 4-fold or more lower levels of transcription or translation in comparison to a control.

The terms "cancer-associated antigen", or "tumor-specific marker", or "tumor marker", or "biomarker" interchangeably refer to a molecule (typically nucleic acid, protein, carbohydrate or lipid) that is present in a biological sample, e.g. saliva, from a subject with cancer, expressed in a cancer cell, expressed on the surface of a cancer cell, or secreted by a cancer cell differentially in comparison to a biological sample from a subject without cancer or a non-cancer cell, and which is useful for the diagnosis of cancer, for providing a prognosis, or for preferential targeting of a pharmacological agent to the cancer cell. Oftentimes, a cancer-associated antigen is a molecule that is overexpressed in a biological sample from a subject with cancer or a cancer cell in comparison to a biological sample from a subject without cancer or a non-cancer cell, for instance, 1-fold over expression, 2-fold overexpression, 3-fold overexpression or more in comparison. Oftentimes, a cancer-associated antigen is a molecule that is inappropriately synthesized in a cancer cell or present in a biological sample from a subject with cancer, for instance, a molecule that contains deletions, additions or mutations in comparison to the molecule expressed in a biological sample from a subject without cancer or in a non-cancer cell.

It will be understood by the skilled artisan that markers may be used singly or in combination with other markers for any of the uses, e.g., diagnosis or prognosis of oral cancer or periodontal disease.

"Disease transcriptome" or "salivary oral cancer transcriptome" refers to a set of genes differentially expressed in a biological sample from an individual or group of individuals suffering from a given disease. Disease transcriptomes may be derived from a particular biological sample, i.e. saliva as in the scope of the present invention. Many disease transcriptomes are known in the art, as are methods of determining a disease transcriptome (see, e.g., U.S. Pat. Nos. 7,229,774, 7,378,239, 7,378,236, 6,833,247, and 7,171,311).

As used herein, an "expression profile" refers to the quantitative or qualitative level of a biomarker found in a transcriptome, such as a control or salivary oral cancer transcriptome, or periodontal transcriptome. A salivary oral cancer expression profile may comprise, for example, the quantitative or qualitative level of nucleic acid or protein biomarkers that are differentially expressed in the saliva of an individual suffering from oral cancer.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, e.g., in Kasper et al., *Harrison's Principles of Internal Medicine*, eds., 16$^{th}$ ed., Chapter 70 and throughout Part V (2005).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J. Mol. Biol.*, 48:443 (1970), by the search for similarity method of Pearson & Lipman, *Proc. Nat'l. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA*, 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (Academic Press, Inc., N.Y., 1990).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H 1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature*, 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Luminex® xMAP technology is particularly well suited for the present invention.

Diagnostic and Prognostic Methods

The present invention provides methods of diagnosing a cancer, an oral disease, or a systemic or genetic disease, by examining antigens (either the protein or the RNA encoding the protein) including cytokines, such as IL-8, IL-1β, IL-1α, IL-2, IL-3, IL-4, IL-5, IL-6, IL-10, the Salivary Exon Core Transcriptome (SECT) (Hu et al, *Clin Chem* 54(5):824-32 (2008)), the genes listed in Table 1, a combination thereof in biological samples, including wild-type, truncated or alternatively spliced forms, and any other genes that are differentially expressed in the saliva of patients suffering from an oral disease. Diagnosis involves determining the level of a polynucleotide or polypeptide of the invention in a patient and then comparing the level to a baseline or range. Typically, the baseline value is representative of a polynucleotide or polypeptide of the invention in a healthy person not suffering from an oral disease, such as cancer or periodontal disease, as measured using biological sample such as saliva or a tissue sample (e.g., tongue or lymph tissue), serum, or blood. Variation of levels of a polynucleotide or polypeptide of the invention from the baseline range (either up or down) indicates that the patient has an oral disease, such as cancer or periodontal disease, or is at risk of developing an oral disease, such as cancer or periodontal disease or metastatic cancer to the lymph nodes, or extracapsular spread. The present invention also provides methods of diagnosing or providing a prognosis for periodontal disease using oral cancer biomarkers.

PCR assays such as Taqman allelic discrimination assay available from Applied Biosystems can be used to identify RNA. In another embodiment, mass spectroscopy can be used to detect either nucleic acid or protein. Any antibody-based technique for determining a level of expression of a protein of interest can be used. For example, immunoassays such as ELISA, Western blotting, flow cytometry, immunofluorescence, and immunohistochemistry can be used to detect protein in patient samples. Combinations of the above methods, such as those employed in the Luminex® xMAP technology can also be used in the present invention.

Analysis of a protein or nucleic acid can be achieved, for example, by high pressure liquid chromatography (HPLC), alone or in combination with mass spectrometry (e.g., MALDI/MS, MALDI-TOF/MS, tandem MS, etc.).

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (ETA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis,* 18:2184-93 (1997); Bao, *J. Chromatogr. B. Biomed. Sci.,* 699:463-80 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.,* 27:261-276 (1989)).

Specific immunological binding of the antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from a direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as polystyrene beads, magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.,* 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

Analysis of the level of a biomarker can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Compositions, Kits and Integrated Systems

The invention provides compositions, kits and integrated systems for practicing the assays described herein using polynucleotides and polypeptides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the diagnostic assays of the invention. The kits typically include a probe that comprises an antibody or nucleic acid sequence that specifically binds to polypeptides or polynucleotides of the invention, and a label for detecting the presence of the probe. The kits may include several antibodies specific for, or polynucleotide sequences encoding, the polypeptides of the invention.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

EXAMPLES

Example 1

In this Example C4 liquid chromatography, LC/quadrupole time of flight (QqTOF) MS was used to compare the proteins found in the saliva of OSCC samples versus control samples. The purpose of this example was to discover differentially expressed proteins that could serve as potential biomarkers for OSCC detection. Through western blotting and ELISA five protein markers were successfully validated: profilin, MRP14, Mac2BP, catalase and CD59, which provide about 90% sensitivity and specificity for oral cancer detection.

Patient Selection, Sample Collection, and Processing:

All the OSCC patients involved in this example had not received any prior treatment in the form of chemotherapy, radiotherapy, surgery, or alternative remedies prior to sample collection. An equal number of age- and gender-matched subjects with comparable smoking histories were selected as a control group. Among the two subject groups, there were no significant differences in terms of mean age, gender or smoking history. No subjects had a history of prior malignancy, immunodeficiency, autoimmune disorders, hepatitis, or HIV infection. All of the subjects signed the institutional review board-approved consent form. Unstimulated whole saliva samples were collected between 9 a.m. and 10 a.m. with prior mouth rinsing with water. The donors were asked to abstain from eating, drinking, smoking, or using oral hygiene products for at least one hour prior to collection. A well-defined and standardized protocol was used for collection, storage, and processing of oral fluid specimens. Saliva samples were centrifuged at 2,600 g for 15 minutes at 4° C. to remove debris and cells. The supernatant was removed from the pellet and protease inhibitors were included in the collected samples to ensure preservation of the protein integrity (Sigma, 2 mL per mL oral fluid). The samples were carefully aliquoted and stored at −80° C. None of the thawed samples was frozen again for reuse.

C4-HPLC of Whole Saliva Proteins from OSCC and Matched Control Subjects:

The total protein concentration in each saliva samples was measured using 2-D Quant Kit (Amersham). For the proteomic discovery study, equal amounts of whole saliva proteins were pooled from 16 OSCC patients or 16 control subjects, respectively, for the comparative analysis. Shotgun proteomics based on C4 RP-LC prefractionation (HP-1100, Agilent Technologies) of intact proteins and subsequent LC-MS/MS analysis was utilized for profiling of proteins in whole saliva samples pooled from either 16 OSCCs or 16 matched control subjects. Using a C4 column (Vydac), 35 fractions were collected from each pooled saliva samples and subjected to in-solution digestion by trypsin. The resulting peptides were then analyzed individually using capillary LC-QqTOF MS. Protein identification was realized using Mascot database searching against the HUPO IPI protein database.

LC-MS/MS Analysis and Database Searching:

LC-MS/MS analysis of peptides was performed using a LC Packings nano-LC system (Sunnyvale, Calif., USA) with a nanoelectrospray interface (Protana, Odense, Denmark) and quadrupole time-of-flight (Q-TOF) mass spectrometer (Applied Biosystems, QSTAR XL, Foster City, Calif., USA). A New Objective (Woburn, Mass., USA) PicoTip tip (I.D., 8 mm) was used for spraying with the voltage at 1850 V for online MS and MS/MS analyses. The samples were first loaded onto a home-packed C18 precolumn (300 μm×1 mm; particle size 5 μm) and then injected onto a LC Packings PepMap C18 column (75 μm×150 mm; particle size 5 μm) for nano-LC separation at a flow rate of 250 nL/min. The eluents used for the LC were (A) 0.1% formic acid (FA) and (B) 95% ACN/0.1% FA and a 1%/min gradient was used for the separation. The acquired MS/MS data were searched against the IPI human protein database using Mascot (Matrix Science) database searching engine. Positive protein identification was based on standard Mascot criteria for statistical analysis of LC-MS/MS data.

Salivary Protein Biomarker Identification:

Subtractive proteomics was used for initial discovery of potential salivary candidate biomarkers for OSCC. In this approach, two pooled saliva samples were prepared from either 16 OSCCs or 16 matched (age, gender and ethnicity) control subjects. The intact proteins from both pooled samples were pre-fractionated by Reverse phase LC using a C4 column (FIG. 1A). In total, 35 fractions were collected from each pooled samples and subjected to in-solution tryptic digestion. The resulting peptides from each LC fraction were then analyzed individually using nanoLC-QTOF MS and the acquired MS/MS data were searched against the IPI human protein database using Mascot search engine. The number of proteins identified from each fractions of oral cancer saliva sample is shown in FIG. 1B. Many proteins were repeatedly identified from different fractions, and after removing the redundant protein IDS, 429 non-redundant proteins were found from the pooled cancer sample whereas 413 proteins were identified from the pooled control sample. A majority of proteins (n=382) overlapped between two pooled samples. However, 47 proteins were only found in the OSCC patients whereas 31 proteins were only found in the control subjects (FIG. 1C).

Table 1 provides a list of the proteins that were found only in the saliva of OSCC patients by the proteomic approach, many of which are regulatory proteins. The salivary protein found to be overexpressed in OSCC patients include Myc binding protein 2, angiomotin like 2, Ras-related protein Rab-7, Mac-2-binding protein, Rho GDP-dissociation inhibitor 2, CD59 glycoprotein precursor, involucrin, KRAB box family protein, hematopoietic lineage cell specific protein, peroxisome biogenesis factor 1, nuclear mitotic apparatus protein 1, swiprosin-2, PHD finger protein 3, histone H1.2, histone H1.3, calgranulin C, moesin, prothymosin alpha, TRIMS-like protein TNL, catalase, etc. Many of the discovered proteins are regulatory proteins or glycoproteins that may be useful for oral cancer diagnostics and therapeutics. Additional biomarkers that were found to be present in the saliva of oral cancer patients but not in the saliva of control individuals can be found in Table 4 (FIGS. 9A-9N). Additional biomarkers that were found to be present in the saliva of individuals not suffering from oral cancer patients but not in the saliva of individuals suffering from oral cancer can be found in Table 5 (FIGS. 10A-10H). Additional biomarkers that were found to be differentially expressed in the saliva of oral cancer patients as compared to the saliva of control individuals can be found in Table 5 (FIGS. 10A-10H).

TABLE 1

| Accession/Protein Name | Accession/Protein Name |
|---|---|
| IPI00003817 Rho GDP-dissociation inhibitor 2 | IPIOO178083 29 kDa protein |
| 1P100006196 Nuclear mitotic apparatus protein 1 | 1P100217466 Histone H1.3 |
| IPIOOO11302 CD59 glycoprotein | IPI00217471 Epsilon globin |
| IPI00289776 Myc binding protein 2 | IPI00218059 MRDSI protein |
| IPIOOO11692 Involucrin | IPI00218131 Calgranulin |
| IPI00013397 KRAB box family protein | IPI00218836 Acyl-CoA-binding protein |
| IPI00016342 Ras-related protein Rab-7 | IPI00219365 Moesin |
| IPI00021338 Pyruvate dehydrogenase complex E2 subunit | IPI00027462 MRP14 (calganulin B) |
| TPT00021812 Neuroblast differentiation associated protein AHNAK | IPI00220828 Thymosin beta-4 |
| IPI00022058 Development and differentiation enhancing factor 2 | IPI00248359 Similar to POTE2A protein |
| IPI00022465 Splice isoform of citron Rho-interacting kinase | IPI00298853 Vitamin D-binding protein |
| IPI00023673 Mac-2 binding protein | IPI00299024 Brain acid soluble protein 1 |
| IPI00025318 SH3 domain-binding glutamic acid-rich-like protein | 1P100334432 16 kDa protein |
| IPI00025363 Glial fibrillary acidic protein | IPI00334610 41 kDa protein |
| IPI00026156 Hematopoietic lineage cell specific protein | IPI00337654 Prothymosin alpha |
| IPI00032134 Serpin B8 | IPI00376164 5 kDa protein |
| IPI00032236 Angiomotin like 2 | IPI00376165 Thymosin-like 4 |
| IPI00045223 HEJI | IPI00376219 Amyloid beta |
| IPI00060181 Swiprosin-2 | IPI00216691 Profilin |
| IPI00170770 PHD finger protein 3 | IPI00411291 Peroxisome biogenesis factor |
| IPI00175649 Leucine-rich repeat kinase 2 | IPI00412365 43 kDa protein |
| IPI00217465 Histone H1.2 | IPI00418471 Vimentin |
| IPI00465436 Catalase | IPI00455477 TRIM9 |
| | IPI00479902 57 kDa protein |

Enzyme-Linked Immunosorbent Assay (ELISA):

Of particular note is the identification of Mac-2 binding protein (M2BP), which is a tumor antigen [44]. The level of M2BP was further validated in a second cohort of oral cancer and control subjects (OSCC, n=48; matched controls, n=48) using ELISA.

An ELISA was performed to determine the s90K/Mac-2 binding protein levels in saliva samples of 48 oral cancer patients and 48 control patients, ages 24 to 65. Samples were diluted 1:100 in sample diluent and 100 µl was added, in duplicate, onto a 96 Microwell Plate coated with murine monoclonal antibody to human 90K/Mac-2 BP. Five 90K/Mac-2 BP Standards with concentrations of 12.5, 25, 50, 100, and 200 ng/ml were used and 100 µl of each was added, in duplicate, to the first 10 wells. To the blank wells, 100 µl of sample diluent was added. After all of the standards and the 40 samples were aliquoted, the Microwell Plate was covered with a plate cover and incubated at 37° C. for 45 minutes on a rotator set at 100 rpm. After incubation, the microwell strips were washed four times with 300 µl of wash buffer, making sure no residuals were left, followed by the addition of 100 µl of HRP-Conjugate, anti-90K/Mac-2 BP murine monoclonal antibody, to all wells. The plate was incubated again at 37° C. for 45 minutes on a rotator set at 100 rpm, followed by four washes with wash buffer as stated previously. Subsequently, 100 µl of TMB Substrate solution was added to all wells and incubated, in the dark, for 10 minutes at room temperature on a rotator. Finally, 100 µl of stop solution was added to each well and the absorbance was measured by an ELISA plate reader at an absorbance of 450 nm and 620 nm.

Figure 2:
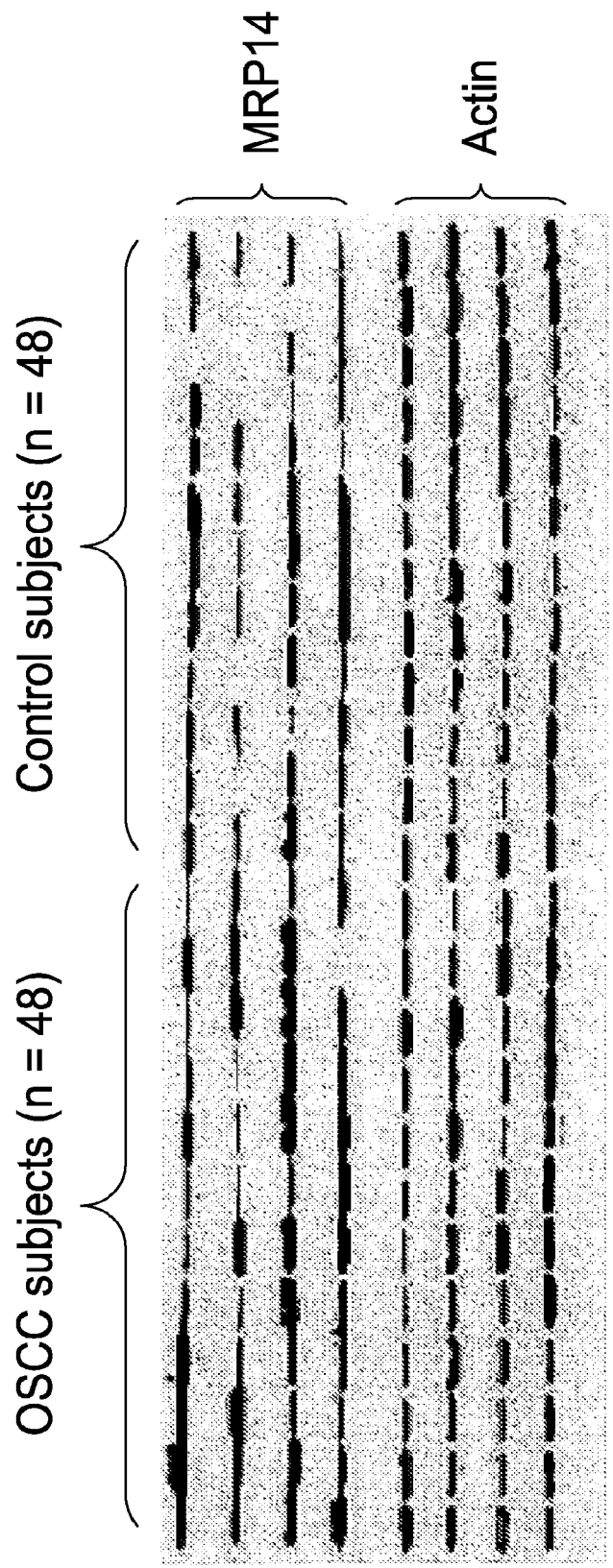
FIG. 2. Immunoblotting of saliva profilin and actin in 48 OSCC and 48 matched control subjects.
Figure 3:
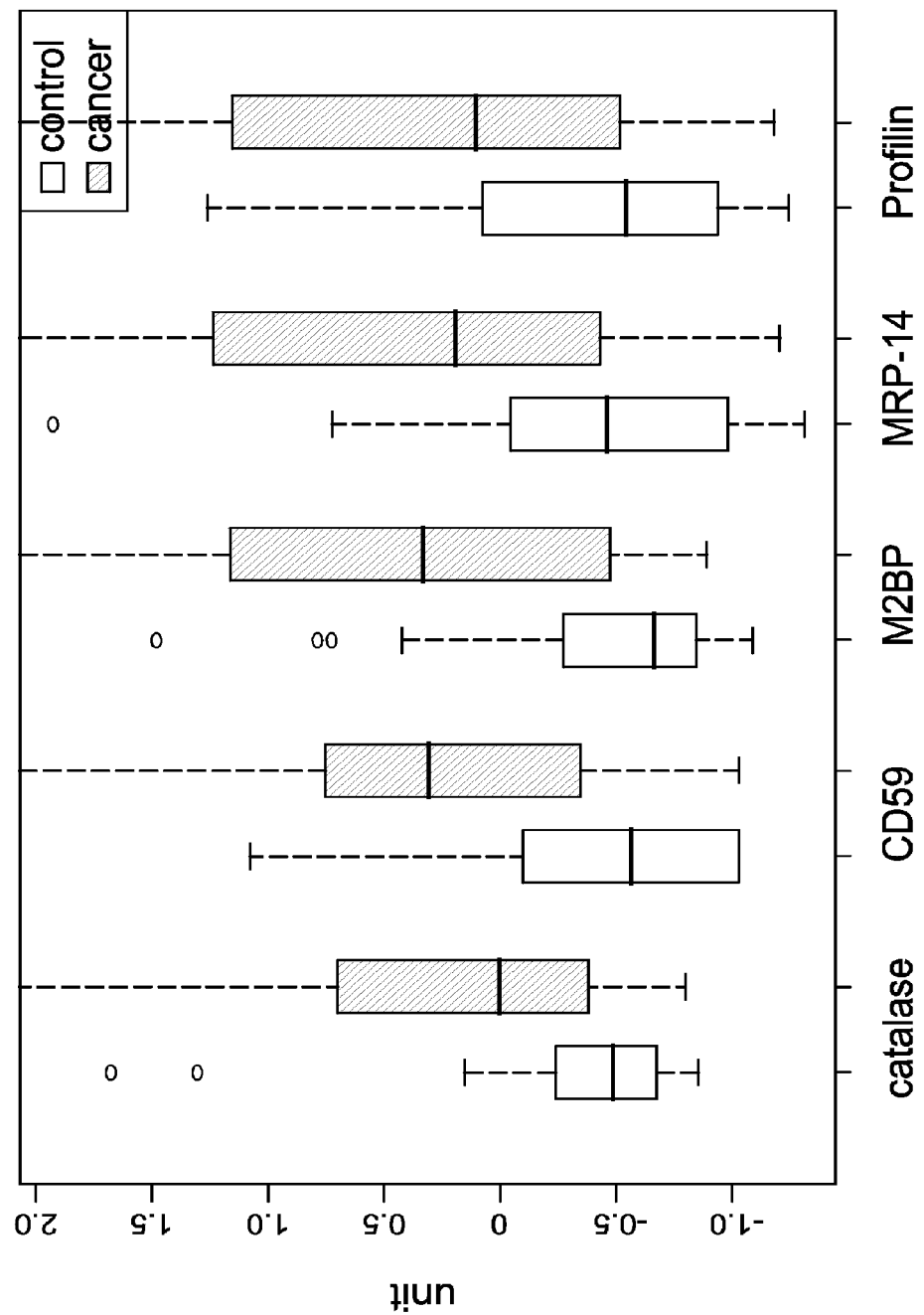
FIG. 3. The levels of 5 candidate protein markers, including catalase, CD59, M2BP, MRP14, and profilin in 48 OSCC and 48 matched control subjects.
Figure 4:
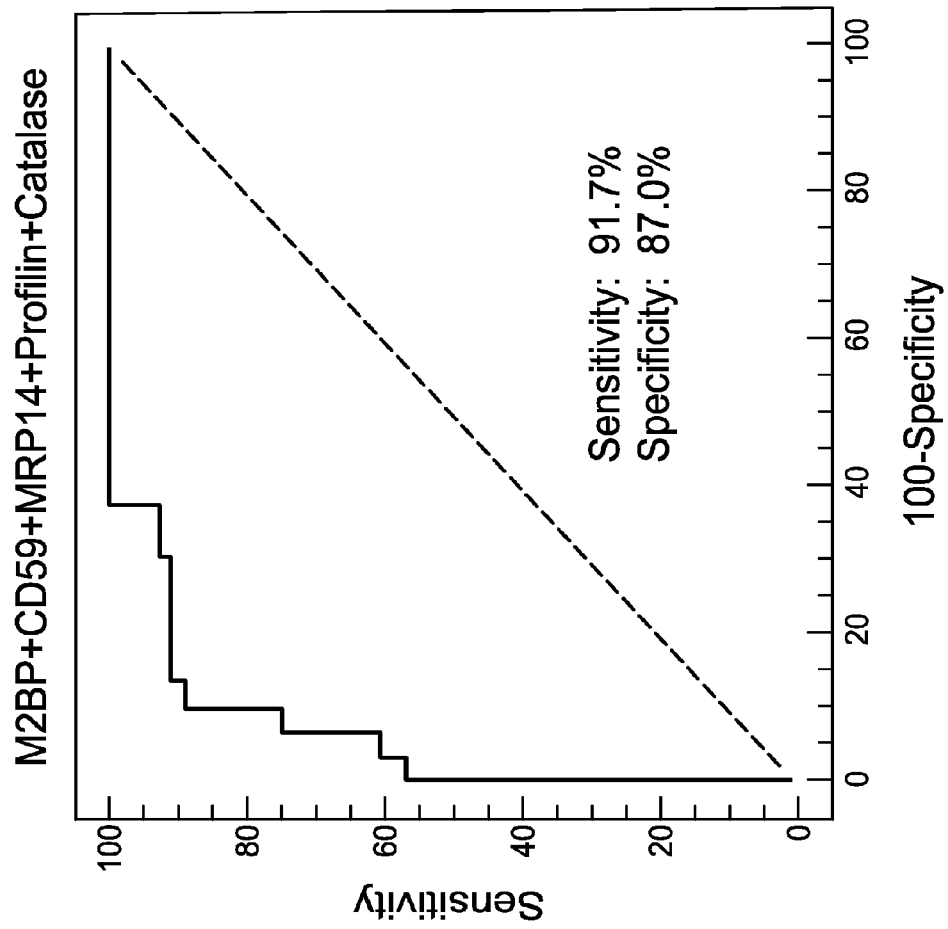
FIG. 4. Receiver operating characteristic analysis suggests the five validated protein markers provide a sensitivity of 91.7% and specificity of 87.0% for OSCC detection. AUC stands for area under the ROC curve (ROC value).

The protein levels of four additional candidate proteins, including CD59, MRP14, catalase, and profiling, were confirmed with the use of the second set of oral cancer and control subject cohorts (48 OSCC, 48 controls) using immunoblotting. FIG. 2 presents the immunoblotting analysis of salivary profilin and actin in 48 oral cancer and 48 matched control subjects. Actin was measured for the purpose of normalizing protein levels of CD59, MRP14, catalase, and profilin between cancer and matched control groups. After normalization, these five candidate markers were found at significantly up-regulated levels as compared to the matched controls (FIG. 3). Receiver operating characteristic (ROC) analysis indicates that these five proteins, including M2BP, CD59, MRP14, catalase, and profilin each have diagnostic value for OSCC detection. As a combination, the five biomarkers provide a high sensitivity of 91.7% and a specificity of 87.0% for OSCC, suggesting that these fluid biomarkers are promising for diagnosis and prognosis of oral cancer (FIG. 4).

Immunoblotting:

The proteins in each of the saliva samples were separated on a NuPAGE gel. After electrophoresis at 150 V for about 1 hr, the proteins were transferred to a PVDF membrane using iBLOT (Invitrogen). The membrane was then saturated with 5% milk in TBST solution overnight at 4° C. Afterwards, the blots were incubated with primary monoclonal or polyclonal antibodies, followed by horseradish peroxidase conjugated anti-mouse or anti-rabbit IgG secondary antibodies (Amersham). Primary antibodies were diluted 1:1000 in 5% milk/TBST and incubated at room temperature for 2 h. Secondary antibody was diluted 1:1000 in 5% milk/TBST and incubated for 1 hr. After washing, bands were visualized by enhanced chemiluminescence (Amersham).

Example 2

Patient Selection

All participants in this study signed the University of California-Los Angeles Institutional Review Board-approved consent form agreeing to donate saliva for experiments. All patients received diagnoses of OSCC and had no prior treatment in the form of chemotherapy, radiotherapy, surgery, or alternative medicine. Healthy control subjects were also recruited and matched for gender, age, smoking history and ethnicity. No patients had a history of prior malignancy, immunodeficiency, autoimmune disorders, hepatitis or HIV infection.

Saliva Collection

Unstimulated whole saliva samples were collected between 9 a.m. and 10 a.m. Patients were asked to refrain from eating, drinking, smoking, and oral hygiene procedures for at least 1 hour before saliva collection. Protease inhibitor cocktail (1 µl/ml aprotonin, 10 mg/ml PMSF, 400 mM sodium orthovanadate, Sigma-Aldrich, St. Louis, Mo., USA) were added immediately after sample collection in order to minimize protein degradation. Briefly, 5 ml of clear whole saliva was obtained from patients after centrifugation at 2600×g for 15 minutes to remove cell pellets and debris. The samples were then divided into 1 ml aliquots and stored at −80° C.

Bead-Based Assay

Human IL-8 and IL-1β Fluorokine MultiAnalyte Profiling systems (Fluorokine MAP) were performed according to R&D systems protocol (R&D systems, Minneapolis, Minn., USA). Saliva samples were diluted five times with calibrator diluent for the IL-1β assay and eight times for the IL-8 assay. Initially the filter bottom and 96-well plate were pre-wet. 50 µl of diluted microparticle solution and 50 µl of sample was added to each well in duplicate. Next the plate was incubated for 3 hours and washed three times with wash buffer. Afterwards, 50 µl of diluted Biotin antibody was added to each well and incubated for 1 hour.

The plate was then washed as described above and 50 µl of diluted Streptavidin-PE was added to each well and incubated for 30 minutes. All incubations were performed at room temperature on an orbital shaker set at 200 rpm. Finally, the plate was washed again with 100 µl of wash buffer. The median relative fluorescence units were measured using the Luminex 100 analyzer (Luminex, Austin, Tex., USA). For the multiplexed assays the same procedure was followed except that the IL-8 and IL-1β microparticles were pooled and then subsequently added to each well.

ELISA

Enzyme-linked immunosorbent assay (ELISA) (Pierce, Rockford, Ill., USA) was performed to determine the IL-8 levels in the saliva samples of OSCC (n=40) and control patients (n=42). Samples were diluted 1:8 in sample diluent and 50 µl was loaded, in duplicate, onto a 96 microwell Plate coated with anti-human IL-8 antibodies. Similarly, the IL-1β ELISA assay (Pierce, Rockford, Ill., USA) was performed in the saliva samples of OSCC (n=36) and control patients (n=42) with a dilution factor of 1:5. After incubation for 1 hour on a rotator (80 rpm), the microwell strips were washed three times with approximately 300 µl of washing buffer, followed by the addition of 50 µl of biotinylated antibody reagent to each well. The plate was incubated again for 1 hour followed by a wash (3×) with the washing buffer. Subsequently, 100 µl of streptavidin-HRP solution was added to all wells and incubated for 30 minutes. After another wash (3×), 100 µA of premixed TMB substrate solution was added to each well and incubated, in the dark, for 30 minutes. Finally, stop solution (100 µl) was added to each well and the absorbance was measured.

Statistical Analysis

Mann-Whitney U test was employed for the comparison of single-plex and multiplex data and the critical alpha level of 0.05 was defined for statistical significance. The Spearman's rank correlation coefficient of single-plex and multiplex data were calculated and represented by $R^2$ values. Using this set of data, we conducted receiver operating characteristic (ROC) curve analyses to evaluate overall performance of the predictive power of each of the biomarkers. The optimal cut-point was determined for each biomarker by searching for those that yielded the maximum corresponding sensitivity and specificity. ROC curves were then plotted on the basis of the set of optimal sensitivity and specificity values. Area under the curve (AUC) was computed via numerical integration of the ROC curves. All statistical data analysis was performed by the statistical software packages R 2.5.0 and Bioconductor.

Results

This example demonstrates that both single-plex and multiplex assays can be used to determine salivary IL-8 and IL-1β levels using xMAP. IL-1β level in saliva was found to be statistically higher in OSCC patients than in control subjects. The boxplot in FIG. 5A shows the distribution of IL-1β levels in OSCC and control subjects. The average level of IL-1β from the single-plex assay was determined as 945.2+/−1134.8 pg/ml for OSCC subjects (n=20) and 314.2+/−444.8 pg/ml for matched control subjects (n=20). ROC analysis resulted in an ROC value of 0.77 with a sensitivity of 75% and specificity of 80%, respectively.

The IL-8 concentration in saliva was also statistically higher in OSCC than in control (FIG. 2A). The average level of IL-8 from the single-plex assay was 3313.2+/−3759.8 pg/ml for OSCC (n=20) and 1061.7+/−1978.8 pg/ml for controls (n=20). The ROC analysis showed an ROC value of 0.80 with a sensitivity of 75% and specificity of 80%, respectively. These results confirmed the use of IL-8 and IL-1β as biomarkers for OSCC detection (St. John et al., *Arch Otolaryngol Head Neck Surg;* 130:929-35 (2004)).

Similar results were obtained for both IL-1β and IL-8 from the multiplexed assays (FIGS. 4B & 5B). The average levels of IL-1β were 1013.5+/−1221.1 pg/ml in OSCC subjects (n=20) and 376.3+/−576.3 pg/ml in control subjects (n=20). The ROC analysis resulted in an ROC value of 0.74 with a sensitivity of 80% and a specificity of 65%, respectively. The average levels of IL-8 were 2834.9+/−3385.6 pg/ml in OSCC subjects (n=20) and 947.3+/−2036.8 pg/ml in control subjects (n=20). The ROC analysis revealed an ROC value of 0.81 with a sensitivity of 75% and specificity of 80%, respectively. These results are summarized in Table 2.

TABLE 2

Comparison of single-plex and multiplex assays for the measurement of IL-8 and IL-1β proteins in saliva of OSCC and matched control subjects.

| Protein | Mean Level (pg/ml) | | p-value | ROC | Sensitivity | Specificity |
|---|---|---|---|---|---|---|
| | OSCC (n = 20) | Control (n = 20) | | | | |
| IL-8 (single-plex) | 3313.2 +/− 3759.8 | 1061.7 +/− 1978.8 | 0.001 | 0.8 | 75% | 80% |
| IL-8 (multiplex) | 2834.9 +/− 3385.6 | 947.3 +/− 2036.8 | 0.0008 | 0.81 | 75% | 80% |
| IL-1β (single-plex) | 945.2 +/− 1134.8 | 314.2 +/− 444.8 | 0.0035 | 0.77 | 75% | 80% |
| IL-1β (multiplex) | 1013.5 +/− 1221.1 | 376.3 +/− 576.3 | 0.0095 | 0.74 | 80% | 65% |

Figure 7:
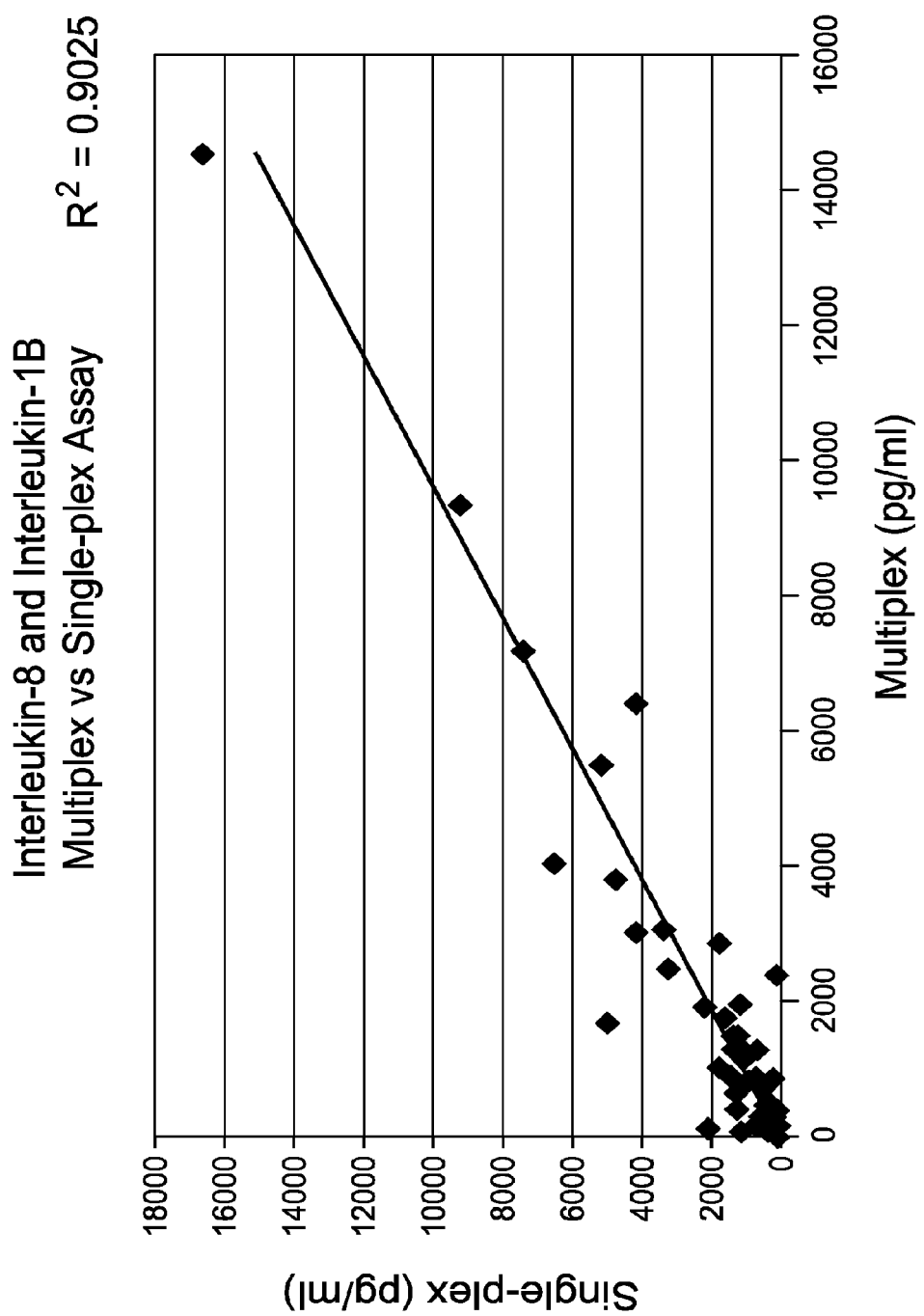
FIG. 7. Correlation between the multiplex and single-plex assays of IL-8 and IL-1β. The $R^2$ value is 0.9025.
Figure 8:
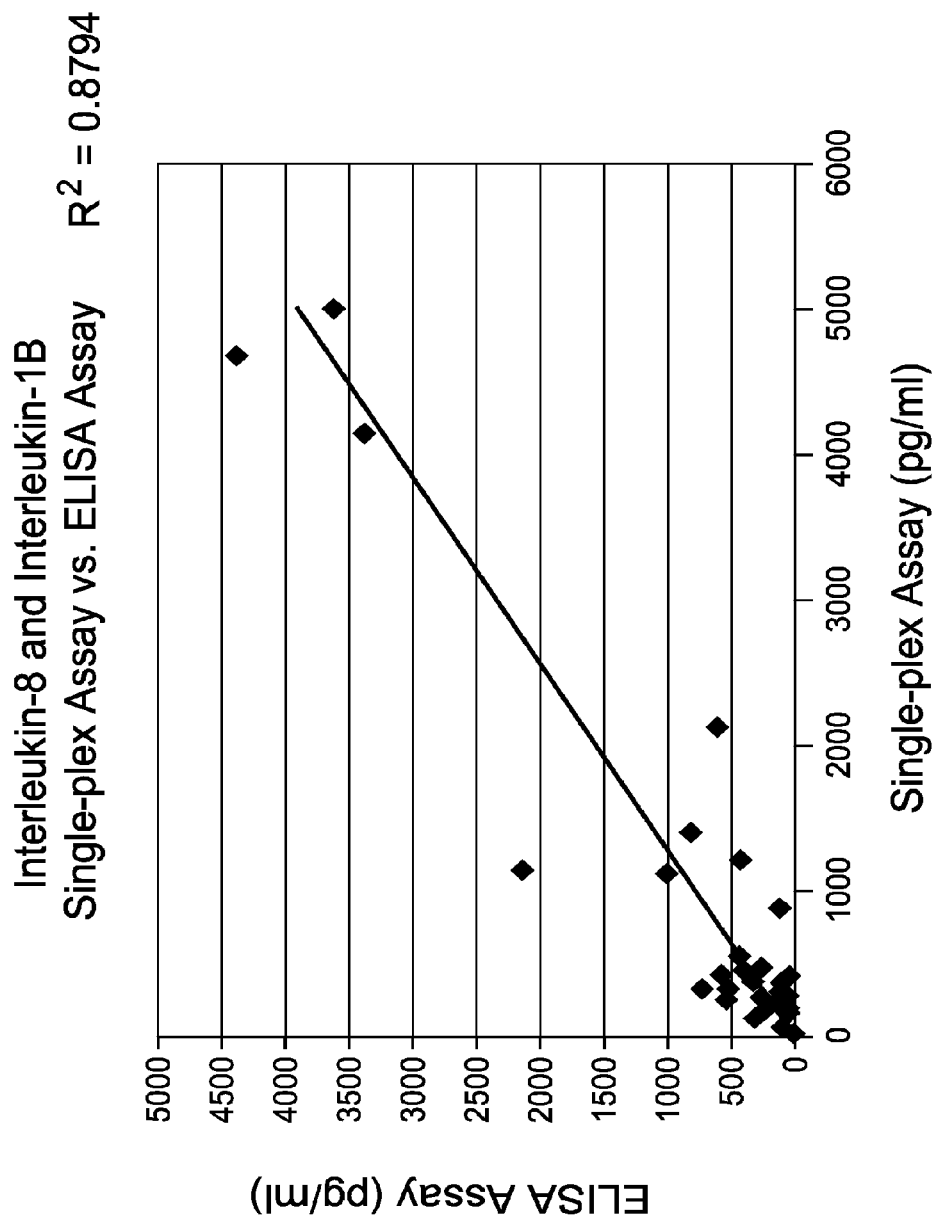
FIG. 8. Correlation between the single-plea and ELISA assays of IL-8 and IL-β. The $R^2$ value is 0.8794.

The multiplex and single-plex Luminex assays show a high correlation coefficient of $R^2=0.9025$ (FIG. 7). We also measured salivary IL-8 and IL-1β levels in the same patients with OSCC and control subjects using ELISA. The average levels of IL-8 using the ELISA assay were 3347.7+/−2929 (OSCC, n=40) and 759.4+/−563 pg/ml (control, n=42). The ROC analysis indicated an ROC value of 0.82 and a sensitivity and specificity of 87.5% and 64.3%, respectively. The average levels of IL-1β were 591.5+/−618.7 pg/ml (OSCC, n=36) and 79.6+/−57.8 pg/ml (control, n=42). The ROC analysis indicated an ROC value of 0.84 and a sensitivity and specificity of 63.9% and 100%, respectively. Luminex assay and ELISA gave highly correlated results. The correlation coefficient ($R^2$) was 0.91 for IL-8 (n=19) and 0.84 for IL-1 β (n=19). FIG. 8 shows the correlation coefficient between the single-plea Luminex assay and ELISA for TL-8 and IL-1β combined, is $R^2=0.8794$.

Discussion

The results of this study indicate that the Luminex xMAP technology is a useful platform for validation of salivary protein biomarkers with both single-plex and multiplex assays. Previous studies have reported achievable results using the multiplex bead-based assay for serum, plasma and cell culture supernatant samples (Allen, C. et al., *Clin Cancer Res*, 13:3182-3190 (2007); Brailo, V. et al., *Oral Oncol*, 42:370-373 (2006); de Jager, W. and Rijkers, G. T., *Methods*, 38:294-303 (2003); Kellar, K. L. et al., *Cytometry*, 45:27-36 (2001); Linkov, F, et al., *Cancer Epidemiol Biomarkers Prev*, 16:102-107 (2007); Oliver, K. G. et al., *Clin Chem*, 44:2057-2060 (1998)). Carson and Vignali reported that the multiplex assay performed as well as the single-plex assay for cytokines but provided better sensitivity than ELISA (Carson, R. T. and Vignali, D. A. A., *J Immunol Methods*, 227:41-52 (1999)). A recent study also found a high correlation between bead-based assays and ELISA (DuPont, N. C. et al., *J Reprod Immunol*, 66:175-191 (2005)). Therefore, multiplex bead-based assays may substitute the ELISA method when a large number of protein analytes need to be validated.

The measured levels of IL-8 in the saliva of OSCC subjects from this study are also comparable to those measured by ELISA from another group of researchers (Rhodus, N. L. et al., *Cancer Detect Prev*, 29:42-45 (2004)). We also demonstrated that there was a high correlation between the Luminex assay data and the ELISA data, and the multiplex assays were found as effective as the single-plex assays for measuring salivary proteins. The average level of IL-1β in OSCC patients obtained from the single-plex assay differed from the multiplexed assay by 7.0% whereas the measurements in control subjects differed by 18.0% between the two assays. As for the measurements for IL-8, the average level of IL-8 in OSCC patients differed by 15.6% between the single-plex and multiplex assays whereas the difference between these two assays for IL-8 in control subjects was 11.4%. A previous study comparing bovine plasma IL-1β levels using single-plex and multiplex assays also reported a difference of 6.4% between the assays (Dernfalk, J. et al., *Vet Immunol Immunopathol*, 118:40-49 (2007)).

In the present example, the IL-8 levels and the IL-1β levels obtained with the single-plex and multiplex assay are comparable to the levels obtained using ELISA. The high correlation between the Luminex assay and ELISA for IL-8 and IL-1β shows the effectiveness of the Luminex assays for detecting protein levels in saliva. Furthermore, the similar results obtained with the single-plex and multiplex assays, confirm the benefits of multiplexing by Luminex xMAP technology without compromising the accuracy.

There has been concern for using inflammatory proteins such as IL-8 and IL-1β as biomarkers although previous studies have firmly shown significantly higher levels of these proteins among OSCC patients than control subjects (Hoffman, T. K. et al., *Head & Neck*, 29:472-478 (2007)). Cytokines are intercellular signaling proteins which play a role in regulating growth, cellular proliferation, angiogenesis and tissue repair. They also function in immune responses to infection, injury and inflammation (de Jager, W. et al., *Clin Diagn Lab Immunol*, 10:133-139 (2006); Ray, C. A. et al., *J Pharma Biomed Anal*, 36:1037-1044 (2005)). Therefore an immunological disease control (e.g., periodontal disease) may need to be included for further validation of IL-8 and IL-1β as truly discriminatory markers for OSCC.

We have recently assayed salivary IL-8 levels in patients with severe periodontal diseases and found that while they have elevated IL-8 in saliva, patients with oral cancer have significantly higher saliva levels of IL-8. It should be noted that cytokines are one of the most low-abundant proteins in human saliva. Therefore, this validation platform should be applicable to most of salivary proteins. In summary, we have demonstrated that Luminex xMAP technology can be used to validate and quantitate protein levels in saliva.

The high correlation between the Luminex assays and ELISA confirms that Luminex xMAP technology is a reliable method for quantification of salivary proteins. We have also showed that the multiplex assay provided comparable results to the single-plex assays therefore demonstrating the efficacy of this technology. Our results suggest that saliva can be a promising and valuable diagnostic fluid because it contains measurable proteins, such as IL-8 and Il-1β, at differential levels that can discriminate disease process. Future validation studies may need to be performed using a larger patient cohort, including periodontal disease group should be included in order to firmly validate IL-8 and IL-1β as protein biomarkers for OSCC. The ability to engage a high throughput platform such as the Luminex xMAP for multiplex protein biomarkers detection in saliva is a significant technology advancement towards the eventual utilization of saliva as a clinical diagnostic fluid.

Example 3

This example demonstrates that the differential expression of IL-8 in saliva is diagnostic of both OSCC and advanced periodontitis. Further, this example shows that the level of IL-8 or IL-8 mRNA can discriminate between OSCC and advanced periodontitis.

To date, two salivary proteins, IL8 and thioredoxin, are known to discriminate between the saliva from patients with oral cancer and the saliva from control subjects. IL8 was discovered through our previous tissue based expression profiling effort. IL8 is significantly elevated in saliva of oral cancer patients and is highly discriminatory of detecting oral cancer in saliva (n=64) with an ROC (receiver operator characteristic) value of 0.95, sensitivity 86% and specificity 97% at cutoff of 600 pg/ml (Alevizos et al., *Oncogene*, 20(43): 6196-204 (2001); St. John et al., *Arch Otolaryngol Head Neck Surg;* 130:929-35 (2004)). Of interest, both IL8 protein and RNA are concordantly increased (St. John et al., *Arch Otolaryngol Head Neck Surg;* 130:929-35 (2004)).

The concentration of IL8 protein in saliva of oral cancer patient and control subjects are 750±45 pg/mL and 250±36 pg/mL respectively. For salivary IL8 mRNA concentration, oral cancer patients are at 200±42 fM while control subjects are at 20±8 fM. Due to the frequent inflammation association of this cytokine, we have tested whether the saliva elevation of IL8 protein and mRNA is specific for oral cancer. Table 3 shows the testing results of IL8 protein and mRNA levels in 50 oral cancer, 50 advanced periodontitis patients and 50 control subjects.

TABLE 3

Salivary IL8 levels in control, oral cancer and advanced periodontitis patients

| Mean | IL8 in Saliva | | |
|---|---|---|---|
| | Control | Oral Cancer | Advanced Periodontitis |
| Protein (pg/ml) | 589.24  p = 0.0001* | p = 0.098  1165.99 | 818.85  p = 0.0044* |
| RNA (fM) | 2.46  p = 0.014* | p = 0.86  16.02 | 2.28  p = 0.012* |

These results demonstrate that salivary IL-8 protein and mRNA levels in oral cancer patients are elevated significantly above those of control patients as well as advanced periodontitis patients, supporting the use of salivary IL-8 as a biomarker for oral cancer detection. Further, IL-8 protein levels are elevated in the saliva of patients with advanced periodontal disease as compared to control individuals.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of diagnosing oral cancer in an individual, the method comprising the steps of:
 (a) detecting the level of a set of oral cancer biomarkers in a salivary sample from an individual, wherein detecting comprises contacting the salivary sample with a set of reagents, wherein the set of reagents specifically binds a set of oral cancer biomarkers, wherein the set of oral cancer biomarkers comprises IL-8, IL-1β, M2BP, Catalase, Calgranulin B, Profilin and CD59;
 (b) determining that the level of at least one of the set of oral cancer biomarkers is elevated in the sample; and
 (c) using the determined elevated level to diagnose oral cancer in the individual.

2. The method claim 1, wherein the method comprises determining the level of at least one of the set of oral cancer biomarkers by a method selected from the group consisting of an antibody based assay, ELISA, western blotting, mass spectrometry, micro array, protein microarray, flow cytometry, immunofluorescence, PCR, immunohistochemistry, and a multiplex detection assay.

3. The method of claim 2, wherein the level of at least one of the set of oral cancer biomarkers is determined by ELISA.

4. The method of claim 2, wherein the level of at least one of the set of oral cancer biomarkers is determined by mass spectroscopy.

5. The method of claim 2, wherein the level of at least one of the set of oral cancer biomarkers is determined by a multiplex assay.

6. The method of claim 5, wherein said multiplex assay is bead-based.

7. The method of claim 6, wherein said assay is a Luminex® xMAP detection assay.

8. The method of claim 1, wherein the step of determining whether the level of one or more biomarkers is elevated comprises the steps of:
 (a) determining the level of said one or more biomarkers in the sample from the individual; and
 (b) comparing said level to at least a first reference level from an individual not suffering from oral cancer.

9. The method of claim 1, wherein the oral cancer is oral squamous cell carcinoma (OSCC).

* * * * *